United States Patent
Usuda et al.

(10) Patent No.: US 6,911,332 B2
(45) Date of Patent: Jun. 28, 2005

(54) ISOLATED POLYNUCLEOTIDES ENCODING D-ARABINO-3-HEXULOSE-6-PHOSPHATE SYNTHASES FROM *METHYLOPHILUS METHYLOTROPHUS*

(75) Inventors: Yoshihiro Usuda, Kanagawa (JP); Yousuke Nishio, Kanagawa (JP); Hisashi Yasueda, Kanagawa (JP); Shinichi Sugimoto, Kanagawa (JP)

(73) Assignee: Ajinomoto Co., Inc., Tokyo (JP)

( * ) Notice: Subject to any disclaimer, the term of this patent is extended or adjusted under 35 U.S.C. 154(b) by 113 days.

(21) Appl. No.: 10/166,653

(22) Filed: Jun. 12, 2002

(65) Prior Publication Data

US 2003/0232338 A1 Dec. 18, 2003

(51) Int. Cl.[7] .............................. C12N 9/10; C12N 9/00; C12N 1/20; C12N 15/00; C07H 21/04
(52) U.S. Cl. .................... 435/193; 435/183; 435/252.3; 435/320.1; 435/69.1; 536/23.2; 536/23.7
(58) Field of Search ............................... 435/69.1, 183, 435/193, 252.3, 320.1; 536/23.2, 23.7

(56) References Cited

FOREIGN PATENT DOCUMENTS

| EP | 0035831 | 9/1981 | ........... C12N/15/00 |
|----|---------|--------|-----------------------|
| EP | 0037273 | 10/1981 | ........... C12N/15/00 |
| EP | 0066994 | 12/1982 | ........... C12N/15/00 |
| EP | 1188822 | 3/2002 | ........... C12N/1/21 |
| WO | WO 02/38777 | 5/2002 | ........... C12N/15/60 |

OTHER PUBLICATIONS

U.S. Appl. No. 10/166,653, filed Jun. 12, 2002, Usuda et al.
U.S. Appl. No. 10/375,266, filed Feb. 28, 2003, Usuda et al.
U.S. Appl. No. 10/375,039, filed Feb. 28, 2003, Usuda et al.
U.S. Appl. No. 10/375,010, filed Feb. 28, 2003, Usuda et al.
U.S. Appl. No. 10/416,021, filed May 12, 2003, Iomantas et al.
U.S. Appl. No. 09/926,299, filed Oct. 9, 2001, Gunji et al.

*Primary Examiner*—Manjunath N. Rao
*Assistant Examiner*—Christian L. Fronda
(74) *Attorney, Agent, or Firm*—Shelly Guest Cermak

(57) ABSTRACT

The present invention provides polypeptides and polynucleotides involved in C1 assimilation in *Methylophilus methylotrophus* and methods of producing amino acids in microorganisms having enhanced or attenuated expression of these polypeptides and/or polynucleotides.

20 Claims, No Drawings

ISOLATED POLYNUCLEOTIDES ENCODING D-ARABINO-3-HEXULOSE-6-PHOSPHATE SYNTHASES FROM *METHYLOPHILUS METHYLOTROPHUS*

BACKGROUND OF THE INVENTION

1. Field of the Invention

The present invention relates to novel polynucleotides encoding proteins involved in one-carbon compounds metabolism, derived from microorganisms belonging to methylotrophic bacteria and fragments thereof, polypeptides encoded by the polynucleotides and fragments thereof, polynucleotide arrays comprising the polynucleotides and fragments thereof

2. Discussion of the Background

Amino acids such as L-lysine, L-glutamic acid, L-threonine, L-leucine, L-isoleucine, L-valine and L-phenylalanine are industrially produced by fermentation by using microorganisms that belong to the genus *Brevibacterium, Corynebacterium, Bacillus, Escherichia, Streptomyces, Pseudomonas, Arthrobacter, Serratia, Penicillium, Candida* or the like. In order to improve the productivity of amino acids, strains isolated from nature or artificial mutants thereof have been used as these microorganisms, various techniques have been disclosed for enhancing activities of L-amino acid biosynthetic enzymes by using recombinant DNA techniques, to increase the L-amino acid-producing ability.

Productivity of L-amino acids has been considerably increased by breeding of microorganisms such as those mentioned above and the improvement of production methods. However, in order to meet further increase in the demand in future, development of methods for more efficiently producing L-amino acids at lower cost have still been desired.

As methods for producing amino acids by fermentation of methanol which is a fermentation raw material available in a large amount at a low cost, there have conventionally known methods using *Achromobacter* or *Pseudomonas* microorganisms (Japanese Patent Publication (Kokoku) No. 45-25273/1970), *Protaminobacter* microorganisms (Japanese Patent Application Laid-open (Kokai) No. 49-125590/1974), *Protaminobacter* or *Methanomonas* microorganisms (Japanese Patent Application Laid-open (Kokai) No. 50-25790/1975), *Microcyclus* microorganisms (Japanese Patent Application Laid-open (Kokai) No. 52-18886/1977), *Methylobacillus* microorganisms (Japanese Patent Application Laid-open (Kokai) No. 4-91793/1992), *Bacillus* microorganisms (Japanese Patent Application Laid-open (Kokai) No. 3-505284/1991) and others.

However, no methods have been described for producing L-amino acids using *Methylophilus* bacteria. Although methods described in EP 0 035 831 A, EP 0 037 273 A and EP 0 066 994 A have been described as methods for transforming *Methylophilus* bacteria using recombinant DNA, applying recombinant DNA techniques to improvement of amino acid productivity of *Methylophilus* bacteria has not been described.

Therefore, prior to the present invention genes isolated from *Methylophilus* bacteria that are involved in C1 assimilation and which can be used to improve the yield of amino acids in cultured microorganisms were not described.

SUMMARY OF THE INVENTION

An object of the present invention is to provide novel measures for the improved production of amino acids or an amino acid, where these amino acids include asparagine, threonine, serine, glutamate, glycine, alanine, cysteine, valine, methionine, isoleucine, leucine, tyrosine, phenylalanine, histidine, lysine, tryptophan, arginine and the salts thereof. In a preferred embodiment the amino acids are L-amino acids.

Such a process includes bacteria, which express a protein comprising an amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, and SEQ ID NO:40. In one embodiment the polypeptides are encoded by a polynucleotide selected from the group consisting of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, and SEQ ID NO:39. In another embodiment the polypeptides are encoded by other polynucleotides which have substantial identity to the herein described polynucleotides or those which hybridize under stringent conditions.

Another object of the invention is to provide polynucleotide sequences selected from the group consisting of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, and SEQ ID NO:39; as well as those polynucleotides that have substantial identity to these nucleotide sequences, preferably at least 95% identity.

Another object of the invention is to provide isolated polypeptides having a sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, and SEQ ID NO:40; as well as those polypeptides that have substantial identity to these amino acid sequences, preferably at least 95% identity.

A further object of the invention is a method for producing a protein or proteins by culturing host cells containing the herein described polynucleotides under conditions and for a time suitable for expression of the protein and collecting the protein produce.

Another object is the use of host cells having the polynucleotides described herein to produce amino acids, as well as use of such isolated polypeptides in the production of amino acids.

Other objects of the invention include methods of detecting nucleic acid sequences homologous to at least one of: SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, and SEQ ID NO:39, particularly nucleic acid sequences encoding polypeptides that herein described proteins or polypeptides and methods of making nucleic acids encoding such polypeptides.

The above objects highlight certain aspects of the invention. Additional objects, aspects and embodiments of the invention are found in the following detailed description of the invention.

DETAILED DESCRIPTION OF THE INVENTION

Unless otherwise defined, all technical and scientific terms used herein have the same meaning as commonly understood by one of ordinary skill in the art of molecular biology. Although methods and materials similar or equivalent to those described herein can be used in the practice or testing of the present invention, suitable methods and materials are described herein. All publications, patent applications, patents, and other references mentioned herein are incorporated by reference in their entirety. In addition, the materials, methods, and examples are illustrative only and are not intended to be limiting.

Reference is made to standard textbooks of molecular biology that contain definitions and methods and means for carrying out basic techniques, encompassed by the present invention. See, for example, Sambrook et al., Molecular Cloning: A Laboratory Manual, Third Edition, Cold Spring Harbor Laboratory Press, New York (2001), Current Protocols in Molecular Biology, Ausebel et al (eds.), John Wiley & Sons, New York (2001) and the various references cited therein.

*Methylophilus methylotrophus* (*M. methylotrophus*) is a gram negative ribulose monophosphate cycle methanol-utilizer, which can be used for the large-scale production of a variety of fine chemicals including amino acids, nucleic acids, vitamins, saccharides, and so on. The polynucleotides of this invention, therefore, can be used to identify microorganisms, which can be used to produce fine chemicals, for example, by fermentative processes. Modulation of the expression of the polynucleotides in the metabolism of one-carbon compounds of the present invention, can be used to modulate the production of one or more fine chemicals from a microorganism (e.g., to improve the yield of production of one or more fine chemicals from *Methylophilus* or *Methylbacillus* species).

The proteins encoded by the polynucleotides of the present invention are capable of, for example, performing a function involved in the metabolism of one-carbon compounds in *M. methylotrophus*, such as methanol, formaldehyde, formate, or methylamine. Given the availability of cloning vectors used in *M. methylotrophus*, such as those disclosed in Methane and Methanol Utilizers, Plenum Press, New York (1992) edited by J. Colin Murrell and Howard Dalton, the nucleic acid molecules of the present invention may be used in the genetic engineering of this organism to make it better or more efficient producer of one or more fine chemicals.

There are a number of mechanisms by which the alteration of a protein of the present invention may affect the yield, production, and/or efficiency of production of a fine chemical from *M. methylotrophus* bacteria, which have the altered protein incorporated. Improving the ability of the cell to utilize formaldehyde (e.g., by manipulating the genes encoding enzymes involved in the incorporation and conversion of the compound into sugar compounds, such as fructose-6-phosphate), one may increase the yield or productivity of desired fine chemicals. Furthermore, by suppressing the activity of enzymes involved in the wasteful pathway such as the conversion of formaldehyde to carbon dioxide, one may also increase the yield or productivity of desired fine chemicals.

"L-amino acids" or "amino acids" as used herein means one or more amino acids, including their salts, preferably chosen from the following: L-asparagine, L-threonine, L-serine, L-glutamate, L-glycine, L-alanine, L-cysteine, L-valine, L-methionine, L-isoleucine, L-leucine, L-tyrosine, L-phenylalanine, L-histidine, L-lysine, L-tryptophan and L-arginine.

"Isolated" as used herein means separated out of its natural environment.

"Polynucleotide" as used herein relates to polyribonucleotides and polydeoxyribonucleotides, it being possible for these to be non-modified RNA or DNA or modified RNA or DNA.

"Polypeptides" as used herein are understood to mean peptides or proteins which comprise two or more amino acids bonded via peptide bonds. In particular, the term refers to polypeptides which are at least 70%, preferably at least 80% and more preferably at least 90% to 95% identical to the polypeptides according to the present invention. Included within the scope of the present invention are polypeptide fragments of SEQ ID NO: 12 and SEQ ID NO: 14 or those which are identical as described Polynucleotides which encode the polypeptides of the invention as used herein is understood to mean the sequences exemplified in this application as well as those sequences which have substantial identity to SEQ ID NO: 11 and SEQ ID NO: 13 and which encode a molecule having one or more of the bioactivities of the associated gene products. Preferably, such polynucleotides are those which are at least 70%, preferably at least 80% and more preferably at least 90% to 95% identical to SEQ ID NO: 11 and SEQ ID NO: 13.

Polynucleotides according to the invention may be employed as probes to isolate and/or identify RNA, cDNA and DNA molecules, e.g., full-length genes or polynucleotides which code for the polypeptides described herein. Likewise, the probes can be employed to isolate nucleic acids, polynucleotides or genes which have a high sequence similarity or identity with the polynucleotides of the invention.

Polynucleotides of the invention may also be used to design primers useful for the polymerase chain reaction to amplify, identify and/or isolate full-length DNA, RNA or other polynucleotides with high sequence homology or identity to the polynucleotides of the invention, as well as, polynucleotides that encode the polypeptides of the invention. Preferably, probes or primers are at least 15, 16, 17, 18, 19, 20, 21, 22, 23, 24, 25, 26, 27, 28, 29 or 30 nucleotides in length. Oligonucleotides with a length of at least 35, 40, 45, 50, 100, 150, 200, 250 or 300 nucleotides may also be used.

Additionally, methods employing DNA chips, microarrays or similar recombinant DNA technology that enables high throughput screening of DNA and polynucleotides that encode the herein described proteins or polynucleotides with high sequence homology or identity to the polynucleotides described herein. Such methods are known in the art and are described, for example, in Current Protocols in Molecular Biology, Ausebel et al (eds), John Wiley and Sons, Inc. New York (2000).

The polynucleotides and polypeptides of the present invention are involved in C1 assimilation in *M. methylotrophus* and include:

1. Phosphohexuloisomerse enzyme comprises the amino acid sequence of SEQ ID NO:2 and is encoded by the phi gene which comprises the polynucleotide SEQ ID NO:1;
2. Methylene tetrahydromethanopterin tetrahydrofolate dehydrogenase enzyme comprises the amino acid sequence of SEQ ID NO:4 and is encoded by a mtdA gene which comprises the polynucleotide SEQ ID NO:3;

3. Methenyl H4MPT cyclohydrolase enzyme comprises the amino acid sequence of SEQ ID NO:6 and is encoded by a mch gene which comprises the polynucleotide SEQ ID NO:5;
4. The D-arabino-3-hexulose 6-phosphate synthase enzymes: the hps2B enzyme comprises the amino acid sequence of SEQ ID NO:8 and is encoded by a hps2B gene comprising SEQ ID NO:7; the hps2A enzyme comprises the amino acid sequence of SEQ ID NO:10 and is encoded by a hps2A gene comprising SEQ ID NO:9; the hps1B enzyme comprises the amino acid sequence of SEQ ID NO:12 and is encoded by a hps1B gene comprising SEQ ID NO:11; and the hps1A enzyme comprises the amino acid sequence of SEQ ID NO:14 and is encoded by a hps1A gene comprising SEQ ID NO:13;
5. The formylmethanofran dehydrogenase, chain C enzyme comprises the amino acid sequence of SEQ ID NO:16 and is encoded by a fwdC gene comprising SEQ ID NO:15;
6. The formylmethanofran dehydrogenase, chain B enzyme comprises the amino acid sequence of SEQ ID NO:18 and is encoded by a fwdB gene comprising SEQ ID NO:17;
7. The formylmethanofran dehydrogenase, chain A enzyme comprises the amino acid sequence of SEQ ID NO:20 and is encoded by a fwdA gene comprising SEQ ID NO:19;
8. The methylenetetrahydrofolate dehydrogenase/methylenyl-tetrahydrofolate cyclohydrolase enzyme comprises the amino acid sequence of SEQ ID NO:22 and is encoded by a folD gene comprising SEQ ID NO:21;
9. The formyltetrahydrofolate synthetase enzyme comprises the amino acid sequence of SEQ ID NO:24 and is encoded by a fhs gene comprising SEQ ID NO:23;
10. The formylmethanofuran-tetrahydromethanopterin formyltransferase enzyme comprises the amino acid sequence of SEQ ID NO:26 and is encoded by a ffsA gene comprising SEQ ID NO:25;
11. The NAD-dependent formate dehydrogenase γ enzyme comprises the amino acid sequence of SEQ ID NO:28 and is encoded by a fdhB gene comprising SEQ ID NO:27;
12. The NAD-dependent formate dehydrogenase δ enzyme comprises the amino acid sequence of SEQ ID NO:30 and is encoded by a fdhD gene comprising SEQ ID NO:29;
13. The FdhC protein modulates the activity of formate dehydrogenase and comprises the amino acid sequence of SEQ ID NO:32 and is encoded by a polynucleotide comprising SEQ ID NO:31;
14. The NAD-dependent formate dehydrogenase β enzyme comprises the amino acid sequence of SEQ ID NO:34 and is encoded by a fdhB gene comprising SEQ ID NO:33;
15. The NAD-dependent formate dehydrogenase a enzyme comprises the amino acid sequence of SEQ ID NO:36 and is encoded by a fdhA gene comprising SEQ ID NO:35;
16. The formaldehyde activated protein comprises the amino acid sequence of SEQ ID NO:38 and is encoded by a fap gene comprising SEQ ID NO:37;
17. The glutathione-dependent formaldehyde enzyme comprises the amino acid sequence of SEQ ID NO:40 and is encoded by a fad gene comprising SEQ ID NO:39;

The terms "stringent conditions" or "stringent hybridization conditions" includes reference to conditions under which a polynucleotide will hybridize to its target sequence, to a detectably greater degree than other sequences (e.g., at least 2-fold over background). Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing).

Typically, stringent conditions will be those in which the salt concentration is less than approximately 1.5 M Na ion, typically about 0.01 to 1.0 M Na ion (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions also may be achieved with the addition of destabilizing agents such as formamide. Exemplary low stringency conditions include hybridization with a buffer solution of 30 to 35% formamide, 1 M NaCl, 1% SDS (w/v; sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. For DNA—DNA hybrids, the Tm can be approximated from the equation of Meinkoth and Wahl (Anal. Biochem., 138:267–284, 1984): Tm=81.5° C.+16.6 (log M)+0.41 (% GC)—0.61 (% form)—500/L; where M is the molarity of monovalent cations, % GC is the percentage of guanosine and cytosine nucleotides in the DNA, % form is the percentage of formamide in the hybridization solution, and L is the length of the hybrid in base pairs. The Tm is the temperature (under defined ionic strength and pH) at which 50% of a complementary target sequence hybridizes to a perfectly matched probe. Tm is reduced by about 1° C. for each 1% of mismatching; thus, Tm, hybridization and/or wash conditions can be adjusted to hybridize to sequences of the desired identity. For example, if sequences with approximately 90% identity are sought, the Tm can be decreased 10° C.

Generally, stringent conditions are selected to be about 5° C. lower than the thermal melting point (Tm) for the specific sequence and its complement at a defined ionic strength and pH. However, severely stringent conditions can utilize hybridization and/or wash at 1, 2, 3, or 4° C. lower than the thermal melting point (Tm); moderately stringent conditions can utilize a hybridization and/or wash at 6, 7, 8, 9, or 10° C. lower than the thermal melting point (Tm); low stringency conditions can utilize a hybridization and/or wash at 11, 12, 13, 14, 15, or 20° C. lower than the thermal melting point (Tm). Using the equation, hybridization and wash compositions, and desired Tm, those of ordinary skill will understand that variations in the stringency of hybridization and/or wash solutions are inherently described. If the desired degree of mismatching results in a Tm of less than 45° C. (aqueous solution) or 32° C. (formamide solution), it is preferred to increase the SSC concentration so that a higher temperature can be used. An extensive guide to the hybridization of nucleic acids is found in Tijssen, Laboratory Techniques in Biochemistry and Molecular Biology—Hybridization with Nucleic Acid Probes, Part I, Chapter 2 "Overview of principles of hybridization and the strategy of nucleic acid probe assays", Elsevier, New York (1993); and Current Protocols in Molecular Biology, Chapter 2, Ausubel, et al., Eds., Greene Publishing and Wiley-Interscience, New York (1995).

Stringent hybridization conditions are understood to mean those conditions where hybridization, either in solution or on a solid support, occur between two polynucleotide molecules which are 70% to 100% homologous in nucleotide sequence which include 75%, 80%, 85%, 90%, 95%, 98% and all values and subranges therebetween.

Homology, sequence similarity or sequence identity of nucleotide or amino acid sequences may be determined conventionally by using known software or computer programs. To find the best segment of identity or similarity of sequences, BLAST (Altschul et al (1990) J. Mol. Biol. 215:403–410 and Lipman et al (1990) J. Mol. Biol. 215:403–410), FASTA (Lipman et al (1985) Science 227:1435–1441), or Smith and Waterman (Smith and Waterman (1981) J. Mol. Biol. 147:195–197) homology search programs can be used. To perform global alignments, sequence alignment programs such as the CLUSTAL W (Thompson et al (1994) Nucleic Acids Research 22:4673–4680) can be used.

The present invention also provides processes for preparing amino acids using bacteria that comprise at least one polynucleotide whose expression is enhanced or attenuated. Likewise, the invention also provides processes for preparing amino acids using bacteria that comprise at least on polypeptide whose activity is enhanced or attenuated. Preferably, a bacterial cell with enhanced or attenuated expression of one or more of the polypeptides and/or polynucleotides described herein will improve amino acid yield at least 1% compared to a bacterial strain not having the enhanced or attenuated expression. For the production of amino acids the *M. methylotrophus* polynucleotides described herein may be used to target expression, either by disruption to turn off or increase or enhance the expression or relative activity of the polypeptide enzymes encoded therein.

The term "enhancement" as used herein means increasing intracellular activity of one or more polypeptides in the bacterial cell, which in turn are encoded by the corresponding polynucleotides described herein. To facilitate such an increase, the copy number of the genes corresponding to the polynucleotides described herein may be increased. Alternatively, a strong and/or inducible promoter may be used to direct the expression of the polynucleotide, the polynucleotide being expressed either as a transient expression vehicle or homologously or heterologously incorporated into the bacterial genome. In another embodiment, the promoter, regulatory region and/or the ribosome binding site upstream of the gene can be altered to achieve the overexpression. The expression may also be enhanced by increasing the relative half-life of the messenger RNA.

In another embodiment, the enzymatic activity of the polypeptide itself may be increased by employing one or more mutations in the polypeptide amino acid sequence, which increases the activity. For example, altering the relative Km of the polypeptide with its corresponding substrate will result in enhanced activity. Likewise, the relative half-life of the polypeptide may be increased.

In either scenario, that being enhanced gene expression or enhanced enzymatic activity, the enhancement may be achieved by altering the composition of the cell culture media and/or methods used for culturing.

"Enhanced expression" or "enhanced activity" as used herein means an increase of at least 10%, 25%, 50%, 75%, 100%, 150%, 200%, 300%, 400% or 500% compared to a wild-type protein, polynucleotide, gene; or the activity and/or the concentration of the protein present before the polynucleotides or polypeptides are enhanced.

The term "attenuation" as used herein means a reduction or elimination of the intracellular activity of the polypeptides in a bacterial cell that are encoded by the corresponding polynucleotide. To facilitate such an reduction or elimination, the copy number of the genes corresponding to the polynucleotides described herein may be decreased or removed. Alternatively, a weak and/or inducible promoter may used to direct the expression of the polynucleotide, the polynucleotide being expressed either as a transient expression vehicle or homologously or heterologously incorporated into the bacterial genome. For example, the endogenous promoter or regulatory region of the gene corresponding to the isolated polynucleotides described herein may be replaced with the aforementioned weak and/or inducible promoter. Alternatively, the promoter or regulatory region may be removed. The expression may also be attenuated by decreasing the relative half-life of the messenger RNA.

In another embodiment, the enzymatic activity of the polypeptide itself may be decreased or deleted by employing one or more mutations in the polypeptide amino acid sequence, which decreases the activity or removes any detectable activity. For example, altering the relative Kd of the polypeptide with its corresponding substrate will result in attenuated activity. Likewise, a decrease in the relative half-life of the polypeptide will result in attenuated activity.

By attenuation measures, the activity or concentration of the corresponding protein is in general reduced to 0 to 75%, 0 to 50%, 0 to 25%, 0 to 10% or 0 to 5% of the activity or concentration of the wild-type protein or of the activity or concentration of the protein in the starting microorganism.

Suitable vectors for carrying *M. methylotrophus* polynucleotides include those vectors which can direct expression of the gene in bacterial cells as known in the art. One embodiment of the present invention is whereby the vectors contain an inducible or otherwise regulated expression system whereby the *M. methylotrophus* polynucleotides may be expressed under certain conditions and not expressed under other conditions. Furthermore, in another embodiment of the invention, the *M. methylotrophus* polynucleotides can be constitutively expressed. Examples of such vectors and suitable cells in which they can be introduced are described in Sambrook et al., Molecular Cloning: A Laboratory Manual, 3rd Ed., Cold Spring Harbor Laboratory Press, Cold Spring Harbor, N.Y. (2001) and Current Protocols in Molecular Biology, Ausebel et al, (Eds.), John Wiley and Sons, Inc., New York, 2000.

Methods of introducing *M. methylotrophus* polynucleotides or vectors containing the *M. methylotrophus* polynucleotides include electroporation, conjugation, calcium-mediated transfection, infection with bacteriophage and other methods known in the art. These and other methods are described in Sambrook et al., Molecular Cloning: A Laboratory Manual, 3rd Ed., Cold Spring Harbor Laboratory Press, Cold Spring Harbor, N.Y. (2001) and Current Protocols in Molecular Biology, Ausebel et al, (Eds.), John Wiley and Sons, Inc., New York (2000).

The microorganisms that can be used in the present invention should have the ability to produce amino acids, preferably L-amino acids, from a suitable carbon source, preferably carbon sources such as glucose, sucrose, lactose, fructose, maltose, molasses, starch, cellulose or from glycerol and ethanol. The microorganisms can be *Methylophilus* bacteria, preferably *Methylophilus methylotrophus*, *Escherichia* bacteria, preferably *Escherichia coli*, *Corynebacterium*, preferably *Corynebacterium glutamicum*.

Suitable culture conditions for the growth and/or production of *M. methylotrophus* polynucleotides are dependent on the cell type used. Likewise, culturing cells that contain attenuated or enhanced expression of the *M. methylotrophus* polynucleotides or polypeptides, as described herein, may be cultured in accordance with methods known in the art. Examples of culture conditions for various cells is described in Sambrook et al., Molecular Cloning: A Laboratory Manual, 3rd Ed., Cold Spring Harbor Laboratory Press, Cold Spring Harbor, N.Y. (2001); Current Protocols in Molecular Biology, Ausebel et al, (Eds.), John Wiley and Sons, Inc., 2000; and Cells: A Laboratory Manual (Vols. 1–3), Spector et al, (Eds.), Cold Spring Harbor Laboratory Press, Cold Spring Harbor, N.Y., (1988).

Following culturing the polypeptide or protein products, which are encoded by the *M. methylotrophus* polynucleotides, may be purified using known methods of protein purification. These methods include high performance liquid chromatography (HPLC), ion-exchange chromatography, size exclusion chromatography; affinity separations using materials such as beads with exposed heparin, metals, or lipids; or other approaches known to those skilled in the art. These and other methods of protein purification are disclosed in Sambrook et al., Molecular Cloning: A Laboratory Manual, 3rd Ed., Cold Spring Harbor Laboratory Press, Cold Spring Harbor, N.Y. (2001); Current Protocols in Molecular Biology, Ausebel et al, eds., John Wiley and Sons, Inc., 2000 and Protein Purification, Scopes and Cantor, (Eds.), Springer-Verlag, (1994). Likewise, the amino acids produced may be purified by methods known in the art using similar chromatography devices.

The invention also provide antibodies that bind to the polypeptides of the present invention. Antibodies binding to the polypeptides can be either monoclonal or polyclonal, preferably the antibodies are monoclonal. Methods for obtaining antibodies that bind to the polypeptides are known in the art and are described, for example, in Harlow and Lane, Antibodies: A Laboratory Manual, Cold Spring Harbor Laboratory Press, Cold Spring Harbor, N.Y. (1988).

Having generally described this invention, a further understanding can be obtained by reference to certain specific examples which are provided herein for purposes of illustration only, and are not intended to be limiting unless otherwise specified.

EXAMPLES

Whole genome sequencing using random shotgun method is described in Fleischman R. D. et. al. (1995) Science, 269: 496–512.

Example 1

Construction of Genomic Libraries of *Methylophilus methylotrophus*

*M. methylotrophus* AS1 was cultured at 30° C. in the 121 medium described in the Catalogue of Strains (The National Collections of Industrial and Marine Bacteria Ltd., 1994). Cells were collected by centrifugation. Genomic DNA was isolated using the Genome-tip system (Qiagen K.K., Tokyo, Japan). The genomic DNA was sheared and fragmentized by sonication. The resultant fragments in the 1- to 2-kb size range were purified by gel electrophoresis through 1% low-melting agarose gel, followed by recovery using the Wizard DNA purification kit (Promega KK, Tokyo, Japan). The recovered fragments were ligated to the high-copy number vector pUC118 treated by HincII and bacterial alkaline phosphatase (Takara Shuzo, Kyoto, Japan), and this was designated pUC118 library.

For larger fragments (9- to 11-kb in size), the genomic DNA was partially digested by restriction endonuclease Sau3AI, followed by 0.6% agarose gel electrophoresis. The DNA fragments corresponding 9-kb to 11-kb in size were excised from gel and were recovered using the DNACELL (Daiichi Pure Chemicals, Tokyo, Japan). The recovered fragments were ligated into the low-coy number vector pMW118 (Nippon Gene, Toyama, Japan), which is a derivative of the pSC101 (Bernaidi, A. and Bernardi, F. (1984) Nucleic Acids Res. 12, 9415–9426). This library composed of large DNA fragments was designated pMW118 library.

General DNA manipulation was performed according to previously described methods (Sambrook et. al. (1989) "Molecular Cloning: A Laboratory Manual/Second Edition", Cold Spring Harbor Laboratory Press).

Example 2

DNA Sequencing and Sequence Assembly

The pUC118 library were transformed into *Escherichia coli* DH5a and plated on Luria-Bertani medium containing 100 μg/ml ampicillin and 40 μg/ml 5-bromo-4-chloro-3-indolyl-β-D-galactoside (X-Gal). The white colonies were picked up and cultured in Luria-Bertani medium containing 100 μg/ml ampicillin. The individual colony was cultured in the well of the 96 deep-well plates, and the plasmids were isolated using QIAprep Turbo Kit (Qiagen). The DNA fragments inserted into pUC18 were sequenced using a M13 reverse primer. The shotgun sequencing was performed with the BigDye terminators and 3700 DNA analyzer (Applied Biosystems Japan, Tokyo, Japan). Approximately 50,000 samples from pUC18 library corresponding to coverage of approximately 8-fold to the genome size were analyzed and the sequences were assembled by Phred/Phrap software (CodonCode, MA, USA). This assembly treatment yielded 60 contigs with more than 5 kb in size.

As for pMW library, 2,000 clones corresponding to coverage of approximately 5-fold were sequenced using both M13 forward and reverse primers. The end-sequence data were analyzed and the linking clones between contigs were selected from pMW118 library. The inserted fragments of selected clones were amplified by the polymerase chain reaction (PCR) using LA Taq polymerase (Takara Shuzo) and *M. methylotrophus* genomic DNA as a template. These products of PCR were entirely sequenced as described in Example 1, and the gap DNA sequences between contigs were determined. By the additional sequence information, the Phrap assembly software reduced the number of contigs with more than 5 kb in size to 24. Then the 48 DNA primers with sequences complementary to the end-sequences of the 24 contigs were prepared. All possible pairwise combination of the primers were tested by PCR to amplify the DNA fragments of *M. methylotrophus* genomic DNA. The amplified products were sequenced directly. In several cases, the additional primers complementary to different sequences at the end of the contig were used. This strategy could close all of the remaining physical gaps and resulted in a single circular contig. Several regions that had been sequenced in only one direction and had postulated secondary structure were confirmed. By this research, the genome of *M. methylotrophus* was found to be a single circular with the size of 2,869,603 bases and GC content of 49.6%.

Example 3

Sequence Analysis and Annotation

Sequence analysis and annotation was managed using the Genome Gambler software (Sakiyama, T. et. al. (2000)

Biosci. Biotechnol. Biochem. 64: 670–673). All open reading frames of more than 150 bp in length were extracted and the translated amino acid sequences were searched against non-redundant protein sequences in GenBank using the BLAST program (Altschul, S. F. et. al. (1990) J. Mol. Biol. 215, 403–410). Of putative polynucleotide encoding sequences with significant similarities to the sequences in public databases (BLASTP scores of more than 100), the genes involved in methanol metabolism were selected. Start codons (AUG or GUG) were putatively identified by similarity of the genes and their proximity to the ribosome binding sequences (Shine, J. and Dalgamo, L. (1975) Eur. J. Biochem. 57: 221–230). Careful assignment of gene function resulted in the identification of the formaldehyde dehydrogenase gene (fadH), the formate dehydrogenase complex genes (fdhGBACD). The two key enzymes of the ribulose monophosphate pathway, D-arabino-3-hexulose 6-phosphate synthase (hps1A) and phosphohexuloisomerase (phi) were found probably in operon, however, three other hps-like genes (hps1B, hps2A, and hps2B) were identified independently. The one-carbon unit (C1) transfer enzymes found in *Methylobacterium extorquens*, formaldehyde-activating enzyme (fap) (Vorholt, J. A. (2000) J. Bacteriol. 182, 6645–6650), methylene tetrahydromethanopterin dehydrogenase (mtdA), methenyl tetrahydromethanopterin cyclohydrolase gene (mch), formylmethanofuran-tetrahydromethanopterin N-formyltransferase gene (ffsA), and formylmethanofran dehydrogenase subunit genes A, B, and C (fwdBA and fwdC) (Chistoserdova L, et. al. (1998) Science 281, 99–102) were identified in this organism. The bifunctional enzyme, methylenetetrahydrofolate dehydrogenase/methenyltetrahydrofolate cyclohydrolase gene (folD) involved in C1 transfer via tetrahydrofolate was also identified.

Obviously, numerous modifications and variations on the present invention are possible in light of the above teachings. It is therefore to be understood that within the scope of the appended claims, the invention may be practiced otherwise than as specifically described herein.

What is claimed is:

1. An isolated polynucleotide, which encodes a protein comprising the amino acid sequence selected from the group consisting of SEQ ID NO:12 and SEQ ID NO:14.

2. A vector comprising at least one isolated polynucleotide of claim 1.

3. A host cell transformed with at least one isolated polynucleotide of claim 1.

4. The host cell of claim 3, which is a *Methylophilus* bacterium.

5. The host cell of claim 4, which is a *Methylophilus methylotrophus* bacterium.

6. A method of making a protein comprising:
   culturing the host cell of claim 3 for a time and under conditions suitable for expression of said protein; and collecting said protein.

7. An isolated polynucleotide, which comprises a nucleotide sequence selected from the group consisting of SEQ ID NO:11 and SEQ ID NO:13.

8. A vector comprising at least one isolated polynucleotide of claim 7.

9. A host cell transformed with the at least one isolated polynucleotide of claim 7.

10. The host cell of claim 9, which is a *Methylophilus* bacterium.

11. The host cell of claim 10, which is a *Methylophilus methylotrophus* bacterium.

12. A method of making a protein comprising:
    culturing the host cell of claim 9 for a time and under conditions suitable for the expression of the polynucleotide to produce a protein; and collecting said protein.

13. An isolated polynucleotide, which hybridizes under high stringent conditions to at least one of the isolated polynucleotides of claim 7, wherein said polynucleotide encodes a protein having the activity of D-arabino-3-hexulose 6-phosphate synthase.

14. A vector comprising the isolated polynucleotide of claim 13.

15. A host cell transformed with the isolated polynucleotide of claim 13.

16. A method of making a protein comprising:
culturing the host cell of claim 15 for a time and under conditions suitable for the expression of the polynucleotide to produce a protein; and
collecting said protein.

17. An isolated polynucleotide, which is at least 95% identical to the polynucleotide of claim 7, and wherein said polynucleotide encodes a protein having the activity of D-arabino-3-hexulose 6-phosphate synthase.

18. A vector comprising the isolated polynucleotide of claim 17.

19. A host cell transformed with the isolated polynucleotide of claim 17.

20. A method of making a protein comprising:
culturing the host cell of claim 19 for a time and under conditions suitable for the expression of the polynucleotide to produce a protein; and
collecting said protein.

* * * * *

SEQUENCE LISTING

<160> NUMBER OF SEQ ID NOS: 40

<210> SEQ ID NO 1
<211> LENGTH: 537
<212> TYPE: DNA
<213> ORGANISM: Methylophilus methylotrophus
<220> FEATURE:
<221> NAME/KEY: CDS
<222> LOCATION: (1)..(537)
<223> OTHER INFORMATION:

<400> SEQUENCE: 1

```
atg gat cat caa caa ttt att ctg gat aac ctg aag cgt att ctg gat        48
Met Asp His Gln Gln Phe Ile Leu Asp Asn Leu Lys Arg Ile Leu Asp
1               5                   10                  15 gtg act gat aaa tca aaa gcc gct gaa ttg ctg aag ctg gtt gac gaa        96
Val Thr Asp Lys Ser Lys Ala Ala Glu Leu Leu Lys Leu Val Asp Glu
            20                  25                  30 gcc ggt tcc aca ttt atc ggt ggt gca ggc cgt tct ttg ctg gtt tca       144
Ala Gly Ser Thr Phe Ile Gly Gly Ala Gly Arg Ser Leu Leu Val Ser
        35                  40                  45 cgt ttc ttc gcg atg cgt ttg gtg cat tct ggc tac agc gtt tac atg       192
Arg Phe Phe Ala Met Arg Leu Val His Ser Gly Tyr Ser Val Tyr Met
    50                  55                  60 att ggc gaa gtg gtg act cca gcc atc aaa aaa ggt gac ttg ctg atc       240
Ile Gly Glu Val Val Thr Pro Ala Ile Lys Lys Gly Asp Leu Leu Ile
65                  70                  75                  80 ttg gtt tct ggc tct ggt ggt act gca acc ttg ttg cca ttt gtg aaa       288
Leu Val Ser Gly Ser Gly Gly Thr Ala Thr Leu Leu Pro Phe Val Lys
                85                  90                  95 aaa gcc aaa gaa gtg ggc gct aaa cta gtt gtt atc tcc atg aag aaa       336
Lys Ala Lys Glu Val Gly Ala Lys Leu Val Val Ile Ser Met Lys Lys
            100                 105                 110 act tct gcc atg gca gat gtg gct gac ctg gtg atc cag att ggt cag       384
Thr Ser Ala Met Ala Asp Val Ala Asp Leu Val Ile Gln Ile Gly Gln
        115                 120                 125 gat gac agc ttc cca ttg gtc aaa ggc atg cct atg ggc ggt caa ttt       432
Asp Asp Ser Phe Pro Leu Val Lys Gly Met Pro Met Gly Gly Gln Phe
    130                 135                 140 gaa ttg tcc acc ttg gtc ttc ctg gag ggt gcc att tct gag ctg atc       480
Glu Leu Ser Thr Leu Val Phe Leu Glu Gly Ala Ile Ser Glu Leu Ile
```

-continued

| | | | | | | | | | | | | | | | | |
|---|---|---|---|---|---|---|---|---|---|---|---|---|---|---|---|---|
|Glu|Leu|Ser|Thr|Leu|Val|Phe|Leu|Glu|Gly|Ala|Ile|Ser|Glu|Leu|Ile| |
|145| | | | |150| | | | |155| | | | |160| |

```
cac gca aaa ggc ctg act gaa gaa ggt atg cgc gcg ttg cac gct aac    528
His Ala Lys Gly Leu Thr Glu Glu Gly Met Arg Ala Leu His Ala Asn
                165                 170                 175 ttg gaa taa                                                        537
Leu Glu
```

<210> SEQ ID NO 2
<211> LENGTH: 178
<212> TYPE: PRT
<213> ORGANISM: Methylophilus methylotrophus

<400> SEQUENCE: 2

Met Asp His Gln Gln Phe Ile Leu Asp Asn Leu Lys Arg Ile Leu Asp
1               5                   10                  15

Val Thr Asp Lys Ser Lys Ala Ala Glu Leu Leu Lys Leu Val Asp Glu
            20                  25                  30

Ala Gly Ser Thr Phe Ile Gly Gly Ala Gly Arg Ser Leu Leu Val Ser
        35                  40                  45

Arg Phe Phe Ala Met Arg Leu Val His Ser Gly Tyr Ser Val Tyr Met
50                  55                  60

Ile Gly Glu Val Val Thr Pro Ala Ile Lys Lys Gly Asp Leu Leu Ile
65                  70                  75                  80

Leu Val Ser Gly Ser Gly Gly Thr Ala Thr Leu Leu Pro Phe Val Lys
                85                  90                  95

Lys Ala Lys Glu Val Gly Ala Lys Leu Val Val Ile Ser Met Lys Lys
            100                 105                 110

Thr Ser Ala Met Ala Asp Val Ala Asp Leu Val Ile Gln Ile Gly Gln
        115                 120                 125

Asp Asp Ser Phe Pro Leu Val Lys Gly Met Pro Met Gly Gly Gln Phe
    130                 135                 140

Glu Leu Ser Thr Leu Val Phe Leu Glu Gly Ala Ile Ser Glu Leu Ile
145                 150                 155                 160

His Ala Lys Gly Leu Thr Glu Glu Gly Met Arg Ala Leu His Ala Asn
                165                 170                 175

Leu Glu

<210> SEQ ID NO 3
<211> LENGTH: 894
<212> TYPE: DNA
<213> ORGANISM: Methylophilus methylotrophus
<220> FEATURE:
<221> NAME/KEY: CDS
<222> LOCATION: (1)..(894)
<223> OTHER INFORMATION:

<400> SEQUENCE: 3

```
atg aaa aaa acc agt att atg cat ttg ttc act gct gcc aag aat gcc    48
Met Lys Lys Thr Ser Ile Met His Leu Phe Thr Ala Ala Lys Asn Ala
1               5                   10                  15 agt cca ttt gat gtg aat atg gcc ttt gat gct ggc tat gag aaa att    96
Ser Pro Phe Asp Val Asn Met Ala Phe Asp Ala Gly Tyr Glu Lys Ile
            20                  25                  30 att tct tac acc gat gtg act ttg aat gaa atc gtc gcg ttg acg cag   144
Ile Ser Tyr Thr Asp Val Thr Leu Asn Glu Ile Val Ala Leu Thr Gln
        35                  40                  45 gat gcc att ttt tca cgc agc ccg agt gga tta aag cag caa gcc tta   192
Asp Ala Ile Phe Ser Arg Ser Pro Ser Gly Leu Lys Gln Gln Ala Leu
```

|     |     |     |     |     |     |     |     |     |     |     |     |     |     |     |     |
|---|---|---|---|---|---|---|---|---|---|---|---|---|---|---|---|
| ttt | ttt | ggc | ggc | cgc | gat | atc | cag | gtg | gcg | ctg | gaa | atg | cag | aag | cag | 240 |
| Phe | Phe | Gly | Gly | Arg | Asp | Ile | Gln | Val | Ala | Leu | Glu | Met | Gln | Lys | Gln |
| 65 |  |  |  | 70 |  |  |  | 75 |  |  |  | 80 |  |  |  |

(positions 50, 55, 60 header)

```
                  50                   55                   60 ttt ttt ggc ggc cgc gat atc cag gtg gcg ctg gaa atg cag aag cag       240
Phe Phe Gly Gly Arg Asp Ile Gln Val Ala Leu Glu Met Gln Lys Gln
 65              70                  75                  80 gcg cgc agt gcc atg ttc aag cca ttt gaa tgc cat act ttt tct gat       288
Ala Arg Ser Ala Met Phe Lys Pro Phe Glu Cys His Thr Phe Ser Asp
                 85                  90                  95 ccg tcc ggt gcc ttt acc acg gca gca gcc atg ctg gcc aaa gtc gat       336
Pro Ser Gly Ala Phe Thr Thr Ala Ala Ala Met Leu Ala Lys Val Asp
             100                 105                 110 ttt tat ttg cag aaa tct ggt agt ggt ttg ggc aag gaa aaa gtc gct       384
Phe Tyr Leu Gln Lys Ser Gly Ser Gly Leu Gly Lys Glu Lys Val Ala
         115                 120                 125 att ttt ggt gcc agt ggt acc gtg ggc tcg aca gca gca ctc atc gca       432
Ile Phe Gly Ala Ser Gly Thr Val Gly Ser Thr Ala Ala Leu Ile Ala
 130                 135                 140 gct cgc cag gga gcc act gta ttg atg gtg gcg cac tcg gat gtt gcc       480
Ala Arg Gln Gly Ala Thr Val Leu Met Val Ala His Ser Asp Val Ala
145                 150                 155                 160 agt atg cag gcg tat gtt gat aag ctt tct agc aat tat gat gtc agc       528
Ser Met Gln Ala Tyr Val Asp Lys Leu Ser Ser Asn Tyr Asp Val Ser
                 165                 170                 175 ctc aaa gta gtg gat ggc agt aca gag gct gcc aaa gtg gct gtg ttg       576
Leu Lys Val Val Asp Gly Ser Thr Glu Ala Ala Lys Val Ala Val Leu
             180                 185                 190 aat gaa gcg aca gta gcc ttg tgt gca aca cca gct ggg att cgc gtc       624
Asn Glu Ala Thr Val Ala Leu Cys Ala Thr Pro Ala Gly Ile Arg Val
         195                 200                 205 ctt gaa atc aag caa ttc gcc aac tcc aaa tca ctg aaa gtg gtg gca       672
Leu Glu Ile Lys Gln Phe Ala Asn Ser Lys Ser Leu Lys Val Val Ala
 210                 215                 220 gac gta aac gca gtc cct cct tct ggc att gag ggc gta gac aca ttc       720
Asp Val Asn Ala Val Pro Pro Ser Gly Ile Glu Gly Val Asp Thr Phe
225                 230                 235                 240 tct gat ggt ggc gtg att gaa ggc aca caa gtg gcc ggt ttt ggc gcc       768
Ser Asp Gly Gly Val Ile Glu Gly Thr Gln Val Ala Gly Phe Gly Ala
                 245                 250                 255 ttg gcg att ggc cag ttg aaa tat gtc acc caa aac aag cta ctg gag       816
Leu Ala Ile Gly Gln Leu Lys Tyr Val Thr Gln Asn Lys Leu Leu Glu
             260                 265                 270 caa atg ctg caa agc gaa agc ccc atg cac att gat tac cat gag gca       864
Gln Met Leu Gln Ser Glu Ser Pro Met His Ile Asp Tyr His Glu Ala
         275                 280                 285 tat gag tat gcc tgt gca cac gtg gag taa                               894
Tyr Glu Tyr Ala Cys Ala His Val Glu
 290                 295
```

<210> SEQ ID NO 4
<211> LENGTH: 297
<212> TYPE: PRT
<213> ORGANISM: Methylophilus methylotrophus

<400> SEQUENCE: 4

```
Met Lys Lys Thr Ser Ile Met His Leu Phe Thr Ala Ala Lys Asn Ala
 1               5                   10                  15

Ser Pro Phe Asp Val Asn Met Ala Phe Asp Ala Gly Tyr Glu Lys Ile
             20                  25                  30

Ile Ser Tyr Thr Asp Val Thr Leu Asn Glu Ile Val Ala Leu Thr Gln
         35                  40                  45
```

```
Asp Ala Ile Phe Ser Arg Ser Pro Ser Gly Leu Lys Gln Gln Ala Leu
 50                  55                  60

Phe Phe Gly Gly Arg Asp Ile Gln Val Ala Leu Glu Met Gln Lys Gln
 65                  70                  75                  80

Ala Arg Ser Ala Met Phe Lys Pro Phe Glu Cys His Thr Phe Ser Asp
                 85                  90                  95

Pro Ser Gly Ala Phe Thr Thr Ala Ala Met Leu Ala Lys Val Asp
                100                 105                 110

Phe Tyr Leu Gln Lys Ser Gly Ser Gly Leu Gly Lys Glu Lys Val Ala
            115                 120                 125

Ile Phe Gly Ala Ser Gly Thr Val Gly Ser Thr Ala Ala Leu Ile Ala
        130                 135                 140

Ala Arg Gln Gly Ala Thr Val Leu Met Val Ala His Ser Asp Val Ala
145                 150                 155                 160

Ser Met Gln Ala Tyr Val Asp Lys Leu Ser Ser Asn Tyr Asp Val Ser
                165                 170                 175

Leu Lys Val Val Asp Gly Ser Thr Glu Ala Ala Lys Val Ala Val Leu
                180                 185                 190

Asn Glu Ala Thr Val Ala Leu Cys Ala Thr Pro Ala Gly Ile Arg Val
            195                 200                 205

Leu Glu Ile Lys Gln Phe Ala Asn Ser Lys Ser Leu Lys Val Val Ala
210                 215                 220

Asp Val Asn Ala Val Pro Pro Ser Gly Ile Glu Gly Val Asp Thr Phe
225                 230                 235                 240

Ser Asp Gly Gly Val Ile Glu Gly Thr Gln Val Ala Gly Phe Gly Ala
                245                 250                 255

Leu Ala Ile Gly Gln Leu Lys Tyr Val Thr Gln Asn Lys Leu Leu Glu
                260                 265                 270

Gln Met Leu Gln Ser Glu Ser Pro Met His Ile Asp Tyr His Glu Ala
            275                 280                 285

Tyr Glu Tyr Ala Cys Ala His Val Glu
290                 295

<210> SEQ ID NO 5
<211> LENGTH: 975
<212> TYPE: DNA
<213> ORGANISM: Methylophilus methylotrophus
<220> FEATURE:
<221> NAME/KEY: CDS
<222> LOCATION: (1)..(975)
<223> OTHER INFORMATION:

<400> SEQUENCE: 5 atg tct gta acc gca tcg aat tca aca tcc att agc gtt caa caa tat      48
Met Ser Val Thr Ala Ser Asn Ser Thr Ser Ile Ser Val Gln Gln Tyr
 1               5                  10                  15 agc gca cca ctg gtg gcg cat ctg atg gcc aat gcc cca gct tta ggc      96
Ser Ala Pro Leu Val Ala His Leu Met Ala Asn Ala Pro Ala Leu Gly
                 20                  25                  30 tgc gca gtg gca acg cat gaa aca ggc gcc acg att gtg gat gca ggt     144
Cys Ala Val Ala Thr His Glu Thr Gly Ala Thr Ile Val Asp Ala Gly
            35                  40                  45 att caa gca act ggc ggc ctg gaa gca ggg cgc atc atc gcc gaa att     192
Ile Gln Ala Thr Gly Gly Leu Glu Ala Gly Arg Ile Ile Ala Glu Ile
        50                  55                  60 tgc atg ggt ggt tta ggt aga gtg tcg ttg cag caa gtg ccg caa ttt     240
Cys Met Gly Gly Leu Gly Arg Val Ser Leu Gln Gln Val Pro Gln Phe
65                  70                  75                  80
```

```
gcc cac tgg cct ctc agt gtc gtg gtg aca gct acc caa ccg gtg att        288
Ala His Trp Pro Leu Ser Val Val Val Thr Ala Thr Gln Pro Val Ile
                85                  90                  95 gcc tgc ctt ggc agt cag tat gcc ggc tgg gcc ttg tca cac gaa aaa        336
Ala Cys Leu Gly Ser Gln Tyr Ala Gly Trp Ala Leu Ser His Glu Lys
            100                 105                 110 ttc ttc tca ctg ggc agt ggc ccg gca cgc tca att gca cag cgt gaa        384
Phe Phe Ser Leu Gly Ser Gly Pro Ala Arg Ser Ile Ala Gln Arg Glu
        115                 120                 125 gaa gtc ttc aaa gat att aat tac agt gat aaa ggc gag caa acg gtt        432
Glu Val Phe Lys Asp Ile Asn Tyr Ser Asp Lys Gly Glu Gln Thr Val
    130                 135                 140 ttg gtg ctg gaa acc gac aag gtg cct cct gtg cag gtg att gaa aaa        480
Leu Val Leu Glu Thr Asp Lys Val Pro Pro Val Gln Val Ile Glu Lys
145                 150                 155                 160 gtg gcc aga gat act ggc ctg cca gcc aat aag ctg aca ttt atc ctg        528
Val Ala Arg Asp Thr Gly Leu Pro Ala Asn Lys Leu Thr Phe Ile Leu
                165                 170                 175 acc cca acc cgc agt gtg gcc ggt tcc ttg caa gtg act gca cgt gtg        576
Thr Pro Thr Arg Ser Val Ala Gly Ser Leu Gln Val Thr Ala Arg Val
            180                 185                 190 ctc gaa gtt gca ctg cat aaa tgc cat gcc ttg cat ttt gac ctg aat        624
Leu Glu Val Ala Leu His Lys Cys His Ala Leu His Phe Asp Leu Asn
        195                 200                 205 gcc att gtc gat ggt tat ggt gtc gcg cca gta ccg gcg ccc tcg cca        672
Ala Ile Val Asp Gly Tyr Gly Val Ala Pro Val Pro Ala Pro Ser Pro
    210                 215                 220 gac ttt atc gtc ggc atg ggc cgt acc aat gat gcg atc ctg ttt ggc        720
Asp Phe Ile Val Gly Met Gly Arg Thr Asn Asp Ala Ile Leu Phe Gly
225                 230                 235                 240 ggc ttt gtg cag ttg ttt gtg aat acc gat gat gct gca gcg gaa caa        768
Gly Phe Val Gln Leu Phe Val Asn Thr Asp Asp Ala Ala Ala Glu Gln
                245                 250                 255 ctc gcc cag caa cta cct tcc tct tca tcc aaa gat tac ggc cgc cca        816
Leu Ala Gln Gln Leu Pro Ser Ser Ser Ser Lys Asp Tyr Gly Arg Pro
            260                 265                 270 ttc gca cag gtg ttc aaa gcc gtt aat atg gac ttt tac cag att gac        864
Phe Ala Gln Val Phe Lys Ala Val Asn Met Asp Phe Tyr Gln Ile Asp
        275                 280                 285 ccc atg ttg ttc tct cca gcc aaa gtc agt gtg act aac ctc aag tcc        912
Pro Met Leu Phe Ser Pro Ala Lys Val Ser Val Thr Asn Leu Lys Ser
    290                 295                 300 ggc aag act ttc ttt ggc ggc cag ttt aat gaa acc ctt ctg aat caa        960
Gly Lys Thr Phe Phe Gly Gly Gln Phe Asn Glu Thr Leu Leu Asn Gln
305                 310                 315                 320 tca ttt gga agt taa                                                    975
Ser Phe Gly Ser <210> SEQ ID NO 6
<211> LENGTH: 324
<212> TYPE: PRT
<213> ORGANISM: Methylophilus methylotrophus

<400> SEQUENCE: 6

Met Ser Val Thr Ala Ser Asn Ser Thr Ser Ile Ser Val Gln Gln Tyr
1               5                   10                  15

Ser Ala Pro Leu Val Ala His Leu Met Ala Asn Ala Pro Ala Leu Gly
            20                  25                  30

Cys Ala Val Ala Thr His Glu Thr Gly Ala Thr Ile Val Asp Ala Gly
```

-continued

```
                35                  40                  45
Ile Gln Ala Thr Gly Gly Leu Glu Ala Gly Arg Ile Ile Ala Glu Ile
     50                  55                  60
Cys Met Gly Gly Leu Gly Arg Val Ser Leu Gln Gln Val Pro Gln Phe
 65                  70                  75                  80
Ala His Trp Pro Leu Ser Val Val Thr Ala Thr Gln Pro Val Ile
                 85                  90                  95
Ala Cys Leu Gly Ser Gln Tyr Ala Gly Trp Ala Leu Ser His Glu Lys
                100                 105                 110
Phe Phe Ser Leu Gly Ser Gly Pro Ala Arg Ser Ile Ala Gln Arg Glu
                115                 120                 125
Glu Val Phe Lys Asp Ile Asn Tyr Ser Asp Lys Gly Glu Gln Thr Val
            130                 135                 140
Leu Val Leu Glu Thr Asp Lys Val Pro Pro Val Gln Val Ile Glu Lys
145                 150                 155                 160
Val Ala Arg Asp Thr Gly Leu Pro Ala Asn Lys Leu Thr Phe Ile Leu
                165                 170                 175
Thr Pro Thr Arg Ser Val Ala Gly Ser Leu Gln Val Thr Ala Arg Val
                180                 185                 190
Leu Glu Val Ala Leu His Lys Cys His Ala Leu His Phe Asp Leu Asn
                195                 200                 205
Ala Ile Val Asp Gly Tyr Gly Val Ala Pro Val Pro Ala Pro Ser Pro
            210                 215                 220
Asp Phe Ile Val Gly Met Gly Arg Thr Asn Asp Ala Ile Leu Phe Gly
225                 230                 235                 240
Gly Phe Val Gln Leu Phe Val Asn Thr Asp Asp Ala Ala Ala Glu Gln
                245                 250                 255
Leu Ala Gln Gln Leu Pro Ser Ser Ser Lys Asp Tyr Gly Arg Pro
            260                 265                 270
Phe Ala Gln Val Phe Lys Ala Val Asn Met Asp Phe Tyr Gln Ile Asp
                275                 280                 285
Pro Met Leu Phe Ser Pro Ala Lys Val Ser Val Thr Asn Leu Lys Ser
            290                 295                 300
Gly Lys Thr Phe Phe Gly Gly Gln Phe Asn Glu Thr Leu Leu Asn Gln
305                 310                 315                 320
Ser Phe Gly Ser

<210> SEQ ID NO 7
<211> LENGTH: 552
<212> TYPE: DNA
<213> ORGANISM: Methylophilus methylotrophus
<220> FEATURE:
<221> NAME/KEY: CDS
<222> LOCATION: (1)..(552)
<223> OTHER INFORMATION:

<400> SEQUENCE: 7 atg tct gac gat aga atc att atg cgt gtg ggt gaa gcc ctg gtg gct     48
Met Ser Asp Asp Arg Ile Ile Met Arg Val Gly Glu Ala Leu Val Ala
 1               5                  10                  15 ggc ggc cct ccc ggt aca gcc gct gaa ccc gaa gtc gca att ggc gaa     96
Gly Gly Pro Pro Gly Thr Ala Ala Glu Pro Glu Val Ala Ile Gly Glu
                20                  25                  30 atg aac ggc ccg atg ggc acc gca ttt gcc aac ttg ctg ggt gac cag    144
Met Asn Gly Pro Met Gly Thr Ala Phe Ala Asn Leu Leu Gly Asp Gln
            35                  40                  45
```

```
gtg aaa ggc cat acc cgt gta ctg gcg att atg aac acc gat atc atg      192
Val Lys Gly His Thr Arg Val Leu Ala Ile Met Asn Thr Asp Ile Met
     50                  55                  60 gtg cgc cct gcc aca ttg atg gtg agc aag gtg acg gtg aaa gac cca      240
Val Arg Pro Ala Thr Leu Met Val Ser Lys Val Thr Val Lys Asp Pro
 65                  70                  75                  80 cgt tat acc aat atc ttg atg ggc acg gtg caa ggg gcg att gcc aac      288
Arg Tyr Thr Asn Ile Leu Met Gly Thr Val Gln Gly Ala Ile Ala Asn
                 85                  90                  95 ggc gtg ctc gat gcc gtg cgt agc ggc gat atc ccg aaa gaa aaa gcc      336
Gly Val Leu Asp Ala Val Arg Ser Gly Asp Ile Pro Lys Glu Lys Ala
            100                 105                 110 aat gac ttg ggc att att gtg tca gtt tgg ctg agc ccg gcg att ctg      384
Asn Asp Leu Gly Ile Ile Val Ser Val Trp Leu Ser Pro Ala Ile Leu
        115                 120                 125 gaa caa gag aag att gac cac aaa gca ctg ttt gat att cac cgt gag      432
Glu Gln Glu Lys Ile Asp His Lys Ala Leu Phe Asp Ile His Arg Glu
    130                 135                 140 gcg act ttc aag gcg att caa aaa gcc ttg cgc aat gag cct agc ata      480
Ala Thr Phe Lys Ala Ile Gln Lys Ala Leu Arg Asn Glu Pro Ser Ile
145                 150                 155                 160 gac tgg ctg ctg gaa aac cag gag aag att gtg cat aag tat tac cag      528
Asp Trp Leu Leu Glu Asn Gln Glu Lys Ile Val His Lys Tyr Tyr Gln
                165                 170                 175 atg ggc ctt gat ggg aag att taa                                      552
Met Gly Leu Asp Gly Lys Ile
            180
```

<210> SEQ ID NO 8
<211> LENGTH: 183
<212> TYPE: PRT
<213> ORGANISM: Methylophilus methylotrophus

<400> SEQUENCE: 8

```
Met Ser Asp Asp Arg Ile Ile Met Arg Val Gly Glu Ala Leu Val Ala
 1               5                  10                  15

Gly Gly Pro Pro Gly Thr Ala Ala Glu Pro Glu Val Ala Ile Gly Glu
            20                  25                  30

Met Asn Gly Pro Met Gly Thr Ala Phe Ala Asn Leu Leu Gly Asp Gln
        35                  40                  45

Val Lys Gly His Thr Arg Val Leu Ala Ile Met Asn Thr Asp Ile Met
    50                  55                  60

Val Arg Pro Ala Thr Leu Met Val Ser Lys Val Thr Val Lys Asp Pro
 65                  70                  75                  80

Arg Tyr Thr Asn Ile Leu Met Gly Thr Val Gln Gly Ala Ile Ala Asn
                 85                  90                  95

Gly Val Leu Asp Ala Val Arg Ser Gly Asp Ile Pro Lys Glu Lys Ala
            100                 105                 110

Asn Asp Leu Gly Ile Ile Val Ser Val Trp Leu Ser Pro Ala Ile Leu
        115                 120                 125

Glu Gln Glu Lys Ile Asp His Lys Ala Leu Phe Asp Ile His Arg Glu
    130                 135                 140

Ala Thr Phe Lys Ala Ile Gln Lys Ala Leu Arg Asn Glu Pro Ser Ile
145                 150                 155                 160

Asp Trp Leu Leu Glu Asn Gln Glu Lys Ile Val His Lys Tyr Tyr Gln
                165                 170                 175

Met Gly Leu Asp Gly Lys Ile
            180
```

<210> SEQ ID NO 9
<211> LENGTH: 543
<212> TYPE: DNA
<213> ORGANISM: Methylophilus methylotrophus
<220> FEATURE:
<221> NAME/KEY: CDS
<222> LOCATION: (1)..(543)
<223> OTHER INFORMATION:

<400> SEQUENCE: 9

```
atg tca aaa atc gta atg aaa gcc ggt gaa gcg acc gta ttt tcc gaa      48
Met Ser Lys Ile Val Met Lys Ala Gly Glu Ala Thr Val Phe Ser Glu
1               5                   10                  15 ggc aaa gat gtg act gca gcc atg ccg gaa atc gtc atc ggc tcc gta      96
Gly Lys Asp Val Thr Ala Ala Met Pro Glu Ile Val Ile Gly Ser Val
            20                  25                  30 gat ggc cca gtc ggc act gct ttt gcc aac atg atg gcg caa acc aaa     144
Asp Gly Pro Val Gly Thr Ala Phe Ala Asn Met Met Ala Gln Thr Lys
        35                  40                  45 ggc cac aca gcc atg ttt gcc gtg cgt gac atc aac cag atg gtg cgc     192
Gly His Thr Ala Met Phe Ala Val Arg Asp Ile Asn Gln Met Val Arg
    50                  55                  60 cct gcc acc atg atg gtg cca aaa gtc acc ttg aaa gac tca ctg aac     240
Pro Ala Thr Met Met Val Pro Lys Val Thr Leu Lys Asp Ser Leu Asn
65                  70                  75                  80 atc gaa ctg ttt ggt ggc gtg gta caa gcg ggc gtg gct gac ggc atc     288
Ile Glu Leu Phe Gly Gly Val Val Gln Ala Gly Val Ala Asp Gly Ile
                85                  90                  95 acc gat gcc gtg att gaa ggc att atc cct aaa gag ctg gtg aat gac     336
Thr Asp Ala Val Ile Glu Gly Ile Ile Pro Lys Glu Leu Val Asn Asp
            100                 105                 110 ctg tgc atc gtt gca ttg ctg tgg att gat ccg ggc tgt gcc aaa gaa     384
Leu Cys Ile Val Ala Leu Leu Trp Ile Asp Pro Gly Cys Ala Lys Glu
        115                 120                 125 gca aac ctg gac aag gct gac ctg tac aaa aac aac tac gaa gcg atc     432
Ala Asn Leu Asp Lys Ala Asp Leu Tyr Lys Asn Asn Tyr Glu Ala Ile
    130                 135                 140 aag ctg gcc ttg aaa cgc gcc ttg aac gac gag cct agc att gat gaa     480
Lys Leu Ala Leu Lys Arg Ala Leu Asn Asp Glu Pro Ser Ile Asp Glu
145                 150                 155                 160 atc atc gct aac cgt cac aaa atc aag cac tgt atg tgg gaa gac agc     528
Ile Ile Ala Asn Arg His Lys Ile Lys His Cys Met Trp Glu Asp Ser
                165                 170                 175 tgg gat cag aaa taa                                                  543
Trp Asp Gln Lys
            180
```

<210> SEQ ID NO 10
<211> LENGTH: 180
<212> TYPE: PRT
<213> ORGANISM: Methylophilus methylotrophus

<400> SEQUENCE: 10

```
Met Ser Lys Ile Val Met Lys Ala Gly Glu Ala Thr Val Phe Ser Glu
1               5                   10                  15

Gly Lys Asp Val Thr Ala Ala Met Pro Glu Ile Val Ile Gly Ser Val
            20                  25                  30

Asp Gly Pro Val Gly Thr Ala Phe Ala Asn Met Met Ala Gln Thr Lys
        35                  40                  45

Gly His Thr Ala Met Phe Ala Val Arg Asp Ile Asn Gln Met Val Arg
```

```
                50                  55                  60
Pro Ala Thr Met Met Val Pro Lys Val Thr Leu Lys Asp Ser Leu Asn
65                  70                  75                  80

Ile Glu Leu Phe Gly Gly Val Val Gln Ala Gly Val Ala Asp Gly Ile
                85                  90                  95

Thr Asp Ala Val Ile Glu Gly Ile Ile Pro Lys Glu Leu Val Asn Asp
            100                 105                 110

Leu Cys Ile Val Ala Leu Leu Trp Ile Asp Pro Gly Cys Ala Lys Glu
        115                 120                 125

Ala Asn Leu Asp Lys Ala Asp Leu Tyr Lys Asn Asn Tyr Glu Ala Ile
    130                 135                 140

Lys Leu Ala Leu Lys Arg Ala Leu Asn Asp Glu Pro Ser Ile Asp Glu
145                 150                 155                 160

Ile Ile Ala Asn Arg His Lys Ile Lys His Cys Met Trp Glu Asp Ser
                165                 170                 175

Trp Asp Gln Lys
            180

<210> SEQ ID NO 11
<211> LENGTH: 882
<212> TYPE: DNA
<213> ORGANISM: Methylophilus methylotrophus
<220> FEATURE:
<221> NAME/KEY: CDS
<222> LOCATION: (1)..(882)
<223> OTHER INFORMATION:

<400> SEQUENCE: 11 atg gca caa acc cag atg gca ttg gat tca ttg gat ttt gac gca acg      48
Met Ala Gln Thr Gln Met Ala Leu Asp Ser Leu Asp Phe Asp Ala Thr
1               5                   10                  15 atc gct ttg gca gct aaa gta gcg cca cac gta gat atc ttg gaa att      96
Ile Ala Leu Ala Ala Lys Val Ala Pro His Val Asp Ile Leu Glu Ile
                20                  25                  30 ggt aca cct tgt atc aag cac aac ggt atc gaa ctg ttg aaa gca ttg     144
Gly Thr Pro Cys Ile Lys His Asn Gly Ile Glu Leu Leu Lys Ala Leu
            35                  40                  45 cgt tcc aaa ttc cct aac aac aag att ttg gtt gac ctg aaa acc atg     192
Arg Ser Lys Phe Pro Asn Asn Lys Ile Leu Val Asp Leu Lys Thr Met
        50                  55                  60 gat gct ggc ttc tac gaa gct gag cca ttc tac aaa gca ggt gct gac     240
Asp Ala Gly Phe Tyr Glu Ala Glu Pro Phe Tyr Lys Ala Gly Ala Asp
65                  70                  75                  80 att tgt acc gtg ttg ggt aca gct gat atc ggt acg atc aaa ggt gtg     288
Ile Cys Thr Val Leu Gly Thr Ala Asp Ile Gly Thr Ile Lys Gly Val
                85                  90                  95 atc gac gct gcc aat aaa tat ggc aaa gaa gcg caa att gac ctg atc     336
Ile Asp Ala Ala Asn Lys Tyr Gly Lys Glu Ala Gln Ile Asp Leu Ile
            100                 105                 110 aac gtg aaa gac aaa aaa gcc cgt acc ctg gaa gtg gta aaa ctg ggt     384
Asn Val Lys Asp Lys Lys Ala Arg Thr Leu Glu Val Val Lys Leu Gly
        115                 120                 125 gca cac att atc ggt gtt cac act ggt ttg gac caa caa gca gct ggt     432
Ala His Ile Ile Gly Val His Thr Gly Leu Asp Gln Gln Ala Ala Gly
    130                 135                 140 caa aca cct ttt gct gac ctg ggt ctg gta tcc ggt ttg aaa aca ggc     480
Gln Thr Pro Phe Ala Asp Leu Gly Leu Val Ser Gly Leu Lys Thr Gly
145                 150                 155                 160 gct aaa gta tct gtt gct ggc ggt gtt aaa gcg gca aca acc aag caa     528
```

```
Ala Lys Val Ser Val Ala Gly Val Lys Ala Ala Thr Thr Lys Gln
            165                 170                 175 gtg gta gat gca ggt gct gat atc gtg gtt gct ggt gca gcg atc tac      576
Val Val Asp Ala Gly Ala Asp Ile Val Val Ala Gly Ala Ala Ile Tyr
        180                 185                 190 ggt gct gct gat cca gcg gcg gct gca aac gaa atc acc aaa att gct      624
Gly Ala Ala Asp Pro Ala Ala Ala Ala Asn Glu Ile Thr Lys Ile Ala
        195                 200                 205 cac ggt tct ggc gct gct gct aaa ggt ggc aac aag ttg ctg cca tgg      672
His Gly Ser Gly Ala Ala Ala Lys Gly Gly Asn Lys Leu Leu Pro Trp
        210                 215                 220 atc atc gct gcg gtt gct gca gta ttg gta ttt tca ctg ttg ggt aaa      720
Ile Ile Ala Ala Val Ala Ala Val Leu Val Phe Ser Leu Leu Gly Lys
225                 230                 235                 240 aaa tct gaa gaa gct gct cct gct gcc gag gca cca gca gct gaa gaa      768
Lys Ser Glu Glu Ala Ala Pro Ala Ala Glu Ala Pro Ala Ala Glu Glu
                245                 250                 255 gct gca cct gct gaa gct gcg cct gcc gca gaa gca cca gcg gct gaa      816
Ala Ala Pro Ala Glu Ala Ala Pro Ala Ala Glu Ala Pro Ala Ala Glu
            260                 265                 270 gag gct gca cct gct gaa gct gcg cct gct gaa gaa gct gcg cca gca      864
Glu Ala Ala Pro Ala Glu Ala Ala Pro Ala Glu Glu Ala Ala Pro Ala
        275                 280                 285 act gaa ggt gct aac taa                                              882
Thr Glu Gly Ala Asn
        290
```

<210> SEQ ID NO 12
<211> LENGTH: 293
<212> TYPE: PRT
<213> ORGANISM: Methylophilus methylotrophus

<400> SEQUENCE: 12

```
Met Ala Gln Thr Gln Met Ala Leu Asp Ser Leu Asp Phe Asp Ala Thr
1               5                   10                  15

Ile Ala Leu Ala Ala Lys Val Ala Pro His Val Asp Ile Leu Glu Ile
            20                  25                  30

Gly Thr Pro Cys Ile Lys His Asn Gly Ile Glu Leu Leu Lys Ala Leu
        35                  40                  45

Arg Ser Lys Phe Pro Asn Asn Lys Ile Leu Val Asp Leu Lys Thr Met
    50                  55                  60

Asp Ala Gly Phe Tyr Glu Ala Glu Pro Phe Tyr Lys Ala Gly Ala Asp
65                  70                  75                  80

Ile Cys Thr Val Leu Gly Thr Ala Asp Ile Gly Thr Ile Lys Gly Val
                85                  90                  95

Ile Asp Ala Ala Asn Lys Tyr Gly Lys Glu Ala Gln Ile Asp Leu Ile
            100                 105                 110

Asn Val Lys Asp Lys Lys Ala Arg Thr Leu Glu Val Val Lys Leu Gly
        115                 120                 125

Ala His Ile Ile Gly Val His Thr Gly Leu Asp Gln Gln Ala Ala Gly
    130                 135                 140

Gln Thr Pro Phe Ala Asp Leu Gly Leu Val Ser Gly Leu Lys Thr Gly
145                 150                 155                 160

Ala Lys Val Ser Val Ala Gly Gly Val Lys Ala Ala Thr Thr Lys Gln
                165                 170                 175

Val Val Asp Ala Gly Ala Asp Ile Val Val Ala Gly Ala Ala Ile Tyr
            180                 185                 190
```

```
Gly Ala Ala Asp Pro Ala Ala Ala Asn Glu Ile Thr Lys Ile Ala
            195                 200                 205

His Gly Ser Gly Ala Ala Ala Lys Gly Gly Asn Lys Leu Leu Pro Trp
    210                 215                 220

Ile Ile Ala Ala Val Ala Ala Val Leu Val Phe Ser Leu Leu Gly Lys
225                 230                 235                 240

Lys Ser Glu Glu Ala Ala Pro Ala Ala Glu Ala Pro Ala Ala Glu Glu
                245                 250                 255

Ala Ala Pro Ala Glu Ala Ala Pro Ala Ala Glu Ala Pro Ala Ala Glu
            260                 265                 270

Glu Ala Ala Pro Ala Glu Ala Ala Pro Ala Glu Glu Ala Ala Pro Ala
        275                 280                 285

Thr Glu Gly Ala Asn
        290

<210> SEQ ID NO 13
<211> LENGTH: 480
<212> TYPE: DNA
<213> ORGANISM: Methylophilus methylotrophus
<220> FEATURE:
<221> NAME/KEY: CDS
<222> LOCATION: (1)..(480)
<223> OTHER INFORMATION:

<400> SEQUENCE: 13 atg gca tta aca caa atg gca tta gac tca ttg gat ttt gac gca act      48
Met Ala Leu Thr Gln Met Ala Leu Asp Ser Leu Asp Phe Asp Ala Thr
1               5                   10                  15 atc gct ttg gca gaa aaa gtt gct cca cac gtt gac atc ctg gaa atc      96
Ile Ala Leu Ala Glu Lys Val Ala Pro His Val Asp Ile Leu Glu Ile
                20                  25                  30 ggt aca cca tgc atc aag cac aac ggt atc aaa ttg ctg gaa act ctg     144
Gly Thr Pro Cys Ile Lys His Asn Gly Ile Lys Leu Leu Glu Thr Leu
            35                  40                  45 cgc gct aag ttc cca aac aac aag atc ctg gtt gac ctg aaa act atg     192
Arg Ala Lys Phe Pro Asn Asn Lys Ile Leu Val Asp Leu Lys Thr Met
        50                  55                  60 gac gct ggt gag tac gag tct gag cca ttc tac aaa gcc ggt gct gac     240
Asp Ala Gly Glu Tyr Glu Ser Glu Pro Phe Tyr Lys Ala Gly Ala Asp
65                  70                  75                  80 atc tgc gta gta ttg ggc gta tcc gac atc ggt aca atc aaa ggc gta     288
Ile Cys Val Val Leu Gly Val Ser Asp Ile Gly Thr Ile Lys Gly Val
                85                  90                  95 atc aaa gca gct aac aaa tac ggc aaa aaa gct caa gtt gac ctg atc     336
Ile Lys Ala Ala Asn Lys Tyr Gly Lys Lys Ala Gln Val Asp Leu Ile
                100                 105                 110 agc gtt gaa gac aaa gtt gct cgt act aaa gaa gtt gct gct gct ggt     384
Ser Val Glu Asp Lys Val Ala Arg Thr Lys Glu Val Ala Ala Ala Gly
            115                 120                 125 gct cac atc atc ggt atc cac act ggt ttg gac caa caa gct gct ggt     432
Ala His Ile Ile Gly Ile His Thr Gly Leu Asp Gln Gln Ala Ala Gly
        130                 135                 140 caa act cca ttt gct gac ctg gct gct gtt gcc cgt ttg aac ctg tga     480
Gln Thr Pro Phe Ala Asp Leu Ala Ala Val Ala Arg Leu Asn Leu
145                 150                 155

<210> SEQ ID NO 14
<211> LENGTH: 159
<212> TYPE: PRT
<213> ORGANISM: Methylophilus methylotrophus
```

```
<400> SEQUENCE: 14

Met Ala Leu Thr Gln Met Ala Leu Asp Ser Leu Asp Phe Asp Ala Thr
1               5                   10                  15

Ile Ala Leu Ala Glu Lys Val Ala Pro His Val Asp Ile Leu Glu Ile
                20                  25                  30

Gly Thr Pro Cys Ile Lys His Asn Gly Ile Lys Leu Leu Glu Thr Leu
            35                  40                  45

Arg Ala Lys Phe Pro Asn Asn Lys Ile Leu Val Asp Leu Lys Thr Met
        50                  55                  60

Asp Ala Gly Glu Tyr Glu Ser Glu Pro Phe Tyr Lys Ala Gly Ala Asp
65                  70                  75                  80

Ile Cys Val Val Leu Gly Val Ser Asp Ile Gly Thr Ile Lys Gly Val
                85                  90                  95

Ile Lys Ala Ala Asn Lys Tyr Gly Lys Lys Ala Gln Val Asp Leu Ile
                100                 105                 110

Ser Val Glu Asp Lys Val Ala Arg Thr Lys Glu Val Ala Ala Ala Gly
            115                 120                 125

Ala His Ile Ile Gly Ile His Thr Gly Leu Asp Gln Gln Ala Ala Gly
130                 135                 140

Gln Thr Pro Phe Ala Asp Leu Ala Ala Val Ala Arg Leu Asn Leu
145                 150                 155

<210> SEQ ID NO 15
<211> LENGTH: 672
<212> TYPE: DNA
<213> ORGANISM: Methylophilus methylotrophus
<220> FEATURE:
<221> NAME/KEY: CDS
<222> LOCATION: (1)..(672)
<223> OTHER INFORMATION:

<400> SEQUENCE: 15 atg agc cat att gtt tta acc gcc aaa cca gtc tct cgc aca gtc gat      48
Met Ser His Ile Val Leu Thr Ala Lys Pro Val Ser Arg Thr Val Asp
1               5                   10                  15 tgc cgt gcc ttg ttg ccg ctg gcc tta cag ggt aag act gtc gcc gaa      96
Cys Arg Ala Leu Leu Pro Leu Ala Leu Gln Gly Lys Thr Val Ala Glu
                20                  25                  30 ata gca gcg atc aaa ttg gcc gct aac ctg agt gtc tcg gat gca ttt     144
Ile Ala Ala Ile Lys Leu Ala Ala Asn Leu Ser Val Ser Asp Ala Phe
            35                  40                  45 gag gtc agt cta gac tca gcc aca gag gca ctt aag ctg act ttt aaa     192
Glu Val Ser Leu Asp Ser Ala Thr Glu Ala Leu Lys Leu Thr Phe Lys
        50                  55                  60 aac acg act tct tcg cac caa tat atc ggt ttc ggc atg acg act ggt     240
Asn Thr Thr Ser Ser His Gln Tyr Ile Gly Phe Gly Met Thr Thr Gly
65                  70                  75                  80 cag ctg gtg gtg gaa ggg gat gtg ggt gac ttt tta ggt gcg caa ctg     288
Gln Leu Val Val Glu Gly Asp Val Gly Asp Phe Leu Gly Ala Gln Leu
                85                  90                  95 caa aat ggc gtg ctg atc tgc aag ggc aac gcc ggt gcg cga gcg ggc     336
Gln Asn Gly Val Leu Ile Cys Lys Gly Asn Ala Gly Ala Arg Ala Gly
                100                 105                 110 gac cgt atg cgc aga ggc atg cta ctg att gaa ggc aat gca ggt gat     384
Asp Arg Met Arg Arg Gly Met Leu Leu Ile Glu Gly Asn Ala Gly Asp
            115                 120                 125 tat tgt ggc tct gac atg atg gcg ggt acg ctg ggt gtg cta ggc agc     432
Tyr Cys Gly Ser Asp Met Met Ala Gly Thr Leu Gly Val Leu Gly Ser
        130                 135                 140
```

```
aca ggt gca cac ctg ggt tat ggc atg aag cgc ggg acg cta tta ttg      480
Thr Gly Ala His Leu Gly Tyr Gly Met Lys Arg Gly Thr Leu Leu Leu
145                 150                 155                 160 gcc cag aca cct gcg cca caa gcg acc tgg ata gac tgc ggt ttc cac      528
Ala Gln Thr Pro Ala Pro Gln Ala Thr Trp Ile Asp Cys Gly Phe His
                165                 170                 175 aaa ctg cct ttc ctc aat att ttg tat aaa tcc ttc aag ctg ctc gat      576
Lys Leu Pro Phe Leu Asn Ile Leu Tyr Lys Ser Phe Lys Leu Leu Asp
        180                 185                 190 agc cgc ttt gcg cag atc agc agc cag cgt gtg caa cgc tgg atg ggc      624
Ser Arg Phe Ala Gln Ile Ser Ser Gln Arg Val Gln Arg Trp Met Gly
    195                 200                 205 gat atg ggc ggc ctg ggc aaa gct gaa atc ctg gtc atc cag tct tag      672
Asp Met Gly Gly Leu Gly Lys Ala Glu Ile Leu Val Ile Gln Ser
210                 215                 220

<210> SEQ ID NO 16
<211> LENGTH: 223
<212> TYPE: PRT
<213> ORGANISM: Methylophilus methylotrophus

<400> SEQUENCE: 16

Met Ser His Ile Val Leu Thr Ala Lys Pro Val Ser Arg Thr Val Asp
1               5                   10                  15

Cys Arg Ala Leu Leu Pro Leu Ala Leu Gln Gly Lys Thr Val Ala Glu
            20                  25                  30

Ile Ala Ala Ile Lys Leu Ala Ala Asn Leu Ser Val Ser Asp Ala Phe
        35                  40                  45

Glu Val Ser Leu Asp Ser Ala Thr Glu Ala Leu Lys Leu Thr Phe Lys
    50                  55                  60

Asn Thr Thr Ser Ser His Gln Tyr Ile Gly Phe Gly Met Thr Thr Gly
65                  70                  75                  80

Gln Leu Val Val Glu Gly Asp Val Gly Asp Phe Leu Gly Ala Gln Leu
                85                  90                  95

Gln Asn Gly Val Leu Ile Cys Lys Gly Asn Ala Gly Ala Arg Ala Gly
            100                 105                 110

Asp Arg Met Arg Gly Met Leu Leu Ile Glu Gly Asn Ala Gly Asp
        115                 120                 125

Tyr Cys Gly Ser Asp Met Met Ala Gly Thr Leu Gly Val Leu Gly Ser
    130                 135                 140

Thr Gly Ala His Leu Gly Tyr Gly Met Lys Arg Gly Thr Leu Leu Leu
145                 150                 155                 160

Ala Gln Thr Pro Ala Pro Gln Ala Thr Trp Ile Asp Cys Gly Phe His
                165                 170                 175

Lys Leu Pro Phe Leu Asn Ile Leu Tyr Lys Ser Phe Lys Leu Leu Asp
            180                 185                 190

Ser Arg Phe Ala Gln Ile Ser Ser Gln Arg Val Gln Arg Trp Met Gly
        195                 200                 205

Asp Met Gly Gly Leu Gly Lys Ala Glu Ile Leu Val Ile Gln Ser
    210                 215                 220

<210> SEQ ID NO 17
<211> LENGTH: 1209
<212> TYPE: DNA
<213> ORGANISM: Methylophilus methylotrophus
<220> FEATURE:
<221> NAME/KEY: CDS
<222> LOCATION: (1)..(1209)
```

<223> OTHER INFORMATION:

<400> SEQUENCE: 17

```
atg act aat caa gaa cac atc atg cat act tgc ccg gcc tgc ggc ttg      48
Met Thr Asn Gln Glu His Ile Met His Thr Cys Pro Ala Cys Gly Leu
1               5                   10                  15 cta tgt gac gat atc acg ggg gaa gcc att gcc aag cag caa ttt tcc      96
Leu Cys Asp Asp Ile Thr Gly Glu Ala Ile Ala Lys Gln Gln Phe Ser
            20                  25                  30 tgt ggc aaa gcc gca aaa ttc tat gcg cgg acc aca agc ggt gcc caa     144
Cys Gly Lys Ala Ala Lys Phe Tyr Ala Arg Thr Thr Ser Gly Ala Gln
        35                  40                  45 ccc caa gta ggt ggc aag aat gtt ccg cta gag gat gcg gta aag gca     192
Pro Gln Val Gly Gly Lys Asn Val Pro Leu Glu Asp Ala Val Lys Ala
    50                  55                  60 gcc gcc ggg ttg ctc aat caa gcc gaa gca ccg ctg gtt gca ggg agt     240
Ala Ala Gly Leu Leu Asn Gln Ala Glu Ala Pro Leu Val Ala Gly Ser
65                  70                  75                  80 agt act gat gtg cac gga gca cgt gcc ctc gtg aac ctg gca cag cat     288
Ser Thr Asp Val His Gly Ala Arg Ala Leu Val Asn Leu Ala Gln His
                85                  90                  95 aca ggg gcg gcg atg aca cat ctg aat gct agc agc acc tta cgc aac     336
Thr Gly Ala Ala Met Thr His Leu Asn Ala Ser Ser Thr Leu Arg Asn
            100                 105                 110 atg aaa gtg ttg caa cat cgc ggc tgg cag acc acc aca ctg act gag     384
Met Lys Val Leu Gln His Arg Gly Trp Gln Thr Thr Thr Leu Thr Glu
        115                 120                 125 gtg cgg aac cgt gcg gat gtc atc ctc atg ata ggg acg gat gtc gtg     432
Val Arg Asn Arg Ala Asp Val Ile Leu Met Ile Gly Thr Asp Val Val
    130                 135                 140 acg cat aac gca cgt ttc ttt gag cgt gtg gta tgg gtc aat gac gcc     480
Thr His Asn Ala Arg Phe Phe Glu Arg Val Val Trp Val Asn Asp Ala
145                 150                 155                 160 atg ttt acc gag cct gct gcg cgt aag gtg att tat ctg ggc ggt gac     528
Met Phe Thr Glu Pro Ala Ala Arg Lys Val Ile Tyr Leu Gly Gly Asp
                165                 170                 175 aaa ctc aat acc aag cct ggt gtt gca cca gat gga cgt gca cct gaa     576
Lys Leu Asn Thr Lys Pro Gly Val Ala Pro Asp Gly Arg Ala Pro Glu
            180                 185                 190 gtc att gaa tgt gct tct gaa cat ttg cca gaa gtg atg gca acc ttg     624
Val Ile Glu Cys Ala Ser Glu His Leu Pro Glu Val Met Ala Thr Leu
        195                 200                 205 cgt gcc ctg gtg atg gga aaa cca gtc acg gcg gac acc gtt gct ggt     672
Arg Ala Leu Val Met Gly Lys Pro Val Thr Ala Asp Thr Val Ala Gly
    210                 215                 220 gtc gct gtg agt cgc ttg aaa gcc gtg gcc gag acg ttg aaa gcc gcc     720
Val Ala Val Ser Arg Leu Lys Ala Val Ala Glu Thr Leu Lys Ala Ala
225                 230                 235                 240 caa tat gcg acc ttg gtc tgg gtc tct aaa gat ttg cat tac gac cat     768
Gln Tyr Ala Thr Leu Val Trp Val Ser Lys Asp Leu His Tyr Asp His
                245                 250                 255 gct gaa ctc acc att gaa aat att act gaa acc gta gtc gcg cta aac     816
Ala Glu Leu Thr Ile Glu Asn Ile Thr Glu Thr Val Val Ala Leu Asn
            260                 265                 270 cag aaa agc cgt gcc atg ggc ttg tcg cta ggc ggt agt gac gga gat     864
Gln Lys Ser Arg Ala Met Gly Leu Ser Leu Gly Gly Ser Asp Gly Asp
        275                 280                 285 acc agt gtc aac tat gcg cat acc tgg ctt aat ggc gtg att atc gac     912
Thr Ser Val Asn Tyr Ala His Thr Trp Leu Asn Gly Val Ile Ile Asp
    290                 295                 300
```

-continued

```
gcg cca gaa tgg gaa agc cat gat gcg gtg gtg tgg gtc aat agt tac       960
Ala Pro Glu Trp Glu Ser His Asp Ala Val Val Trp Val Asn Ser Tyr
305                 310                 315                 320 agc cca gat gcc atg ccg cct gca ggt act tcg ccc gtg att ata ttg      1008
Ser Pro Asp Ala Met Pro Pro Ala Gly Thr Ser Pro Val Ile Ile Leu
            325                 330                 335 ggt gcg cct gat agc aag ttt gaa acc gcg ccc gcc gtg ttt atc ccg      1056
Gly Ala Pro Asp Ser Lys Phe Glu Thr Ala Pro Ala Val Phe Ile Pro
        340                 345                 350 gta gcc acg cca ggg ctg gat ggc aat ggc cag cag ttc cgt gtc gat      1104
Val Ala Thr Pro Gly Leu Asp Gly Asn Gly Gln Gln Phe Arg Val Asp
    355                 360                 365 ggt tcg gta acg cta ccg ttg att gcc gcc aaa cct tct gat tta cct      1152
Gly Ser Val Thr Leu Pro Leu Ile Ala Ala Lys Pro Ser Asp Leu Pro
370                 375                 380 acg ctg acg caa gtg gtg gcg atg ata caa gct caa cta caa gga gat      1200
Thr Leu Thr Gln Val Val Ala Met Ile Gln Ala Gln Leu Gln Gly Asp
385                 390                 395                 400 ttg gca tga                                                           1209
Leu Ala
```

<210> SEQ ID NO 18
<211> LENGTH: 402
<212> TYPE: PRT
<213> ORGANISM: Methylophilus methylotrophus

<400> SEQUENCE: 18

```
Met Thr Asn Gln Glu His Ile Met His Thr Cys Pro Ala Cys Gly Leu
1               5                   10                  15

Leu Cys Asp Asp Ile Thr Gly Glu Ala Ile Ala Lys Gln Gln Phe Ser
            20                  25                  30

Cys Gly Lys Ala Ala Lys Phe Tyr Ala Arg Thr Thr Ser Gly Ala Gln
        35                  40                  45

Pro Gln Val Gly Gly Lys Asn Val Pro Leu Glu Asp Ala Val Lys Ala
    50                  55                  60

Ala Ala Gly Leu Leu Asn Gln Ala Glu Ala Pro Leu Val Ala Gly Ser
65                  70                  75                  80

Ser Thr Asp Val His Gly Ala Arg Ala Leu Val Asn Leu Ala Gln His
                85                  90                  95

Thr Gly Ala Ala Met Thr His Leu Asn Ala Ser Ser Thr Leu Arg Asn
            100                 105                 110

Met Lys Val Leu Gln His Arg Gly Trp Gln Thr Thr Leu Thr Glu
        115                 120                 125

Val Arg Asn Arg Ala Asp Val Ile Leu Met Ile Gly Thr Asp Val Val
    130                 135                 140

Thr His Asn Ala Arg Phe Phe Glu Arg Val Val Trp Val Asn Asp Ala
145                 150                 155                 160

Met Phe Thr Glu Pro Ala Ala Arg Lys Val Ile Tyr Leu Gly Gly Asp
                165                 170                 175

Lys Leu Asn Thr Lys Pro Gly Val Ala Pro Asp Gly Arg Ala Pro Glu
            180                 185                 190

Val Ile Glu Cys Ala Ser Glu His Leu Pro Glu Val Met Ala Thr Leu
        195                 200                 205

Arg Ala Leu Val Met Gly Lys Pro Val Thr Ala Asp Thr Val Ala Gly
    210                 215                 220

Val Ala Val Ser Arg Leu Lys Ala Val Ala Glu Thr Leu Lys Ala Ala
```

```
                225                 230                 235                 240
    Gln Tyr Ala Thr Leu Val Trp Val Ser Lys Asp Leu His Tyr Asp His
                    245                 250                 255

Ala Glu Leu Thr Ile Glu Asn Ile Thr Glu Thr Val Val Ala Leu Asn
                    260                 265                 270

Gln Lys Ser Arg Ala Met Gly Leu Ser Leu Gly Gly Ser Asp Gly Asp
                    275                 280                 285

Thr Ser Val Asn Tyr Ala His Thr Trp Leu Asn Gly Val Ile Ile Asp
                    290                 295                 300

Ala Pro Glu Trp Glu Ser His Asp Ala Val Val Trp Val Asn Ser Tyr
    305                 310                 315                 320

Ser Pro Asp Ala Met Pro Pro Ala Gly Thr Ser Pro Val Ile Ile Leu
                    325                 330                 335

Gly Ala Pro Asp Ser Lys Phe Glu Thr Ala Pro Ala Val Phe Ile Pro
                    340                 345                 350

Val Ala Thr Pro Gly Leu Asp Gly Asn Gly Gln Gln Phe Arg Val Asp
                    355                 360                 365

Gly Ser Val Thr Leu Pro Leu Ile Ala Ala Lys Pro Ser Asp Leu Pro
    370                 375                 380

Thr Leu Thr Gln Val Val Ala Met Ile Gln Ala Gln Leu Gln Gly Asp
    385                 390                 395                 400

Leu Ala

<210> SEQ ID NO 19
<211> LENGTH: 1665
<212> TYPE: DNA
<213> ORGANISM: Methylophilus methylotrophus
<220> FEATURE:
<221> NAME/KEY: CDS
<222> LOCATION: (1)..(1665)
<223> OTHER INFORMATION:

<400> SEQUENCE: 19 atg att acg cta ctc aaa aat gcc aaa gtg ata gac ccc gcc cat aac      48
Met Ile Thr Leu Leu Lys Asn Ala Lys Val Ile Asp Pro Ala His Asn
1               5                   10                  15 aag gat ggc gtg gtg caa gat att tat atc cgt gat ggc cgc att att      96
Lys Asp Gly Val Val Gln Asp Ile Tyr Ile Arg Asp Gly Arg Ile Ile
                20                  25                  30 gct aaa cct gcc gac agt gag aaa atc ggt cag ata tat gac ctc aat     144
Ala Lys Pro Ala Asp Ser Glu Lys Ile Gly Gln Ile Tyr Asp Leu Asn
            35                  40                  45 ggc aaa atc gtg atg gcc ggt gcg att gat atg cat agc cat att ggt     192
Gly Lys Ile Val Met Ala Gly Ala Ile Asp Met His Ser His Ile Gly
        50                  55                  60 ggc ggt aaa gtg aat att gcg cgt atg ctg ttg ccg gaa tac cag gcc     240
Gly Gly Lys Val Asn Ile Ala Arg Met Leu Leu Pro Glu Tyr Gln Ala
65                  70                  75                  80 atg cgc aag ttg gag gag cca gaa gct cac atc tgc ggt gcc aat tgc     288
Met Arg Lys Leu Glu Glu Pro Glu Ala His Ile Cys Gly Ala Asn Cys
                85                  90                  95 agc cat cat gcc aca cca aat act acc gat acg ggt atg cgc tat atc     336
Ser His His Ala Thr Pro Asn Thr Thr Asp Thr Gly Met Arg Tyr Ile
                100                 105                 110 gag atg gga tat acc gcc gcc ttt gaa ccg gcc atc ctt gct gtc aat     384
Glu Met Gly Tyr Thr Ala Ala Phe Glu Pro Ala Ile Leu Ala Val Asn
            115                 120                 125 gcg cgt cag gcc cat atg gaa atg ggt gac acg ccc atg atc gac aaa     432
Ala Arg Gln Ala His Met Glu Met Gly Asp Thr Pro Met Ile Asp Lys
```

```
Ala Arg Gln Ala His Met Glu Met Gly Asp Thr Pro Met Ile Asp Lys
    130                 135                 140 ggc ggc tat gcc atg ttg ggt aat gat gat tac ctg cta cgt ttg cta       480
Gly Gly Tyr Ala Met Leu Gly Asn Asp Asp Tyr Leu Leu Arg Leu Leu
145                 150                 155                 160 agc cag aat gcc gac cag aaa acc att aat gac tat gtg gcc tgg aca       528
Ser Gln Asn Ala Asp Gln Lys Thr Ile Asn Asp Tyr Val Ala Trp Thr
                165                 170                 175 ctg cat gcc acg cag acc ata ggt atc aag gta gtg aat cca ggt ggc       576
Leu His Ala Thr Gln Thr Ile Gly Ile Lys Val Val Asn Pro Gly Gly
            180                 185                 190 att tct gcg ttt aaa ttc aac gag cgt cgc cag gat ctg gat caa ctg       624
Ile Ser Ala Phe Lys Phe Asn Glu Arg Arg Gln Asp Leu Asp Gln Leu
        195                 200                 205 cac agt tac tac aac atc acc cca cgc cgc att ttg cag gca ttg agc       672
His Ser Tyr Tyr Asn Ile Thr Pro Arg Arg Ile Leu Gln Ala Leu Ser
    210                 215                 220 cgg gcc gtg aat gaa att ggg att gcc aaa ccg tta cat gtg cac tgc       720
Arg Ala Val Asn Glu Ile Gly Ile Ala Lys Pro Leu His Val His Cys
225                 230                 235                 240 aac aat ctg ggt gtg gct ggt aac ttc cag acc acg ctg gat acc atg       768
Asn Asn Leu Gly Val Ala Gly Asn Phe Gln Thr Thr Leu Asp Thr Met
                245                 250                 255 ggc gcc agc gat ggc ttg ccc atg cat ttg acg cat atc cag ttt cat       816
Gly Ala Ser Asp Gly Leu Pro Met His Leu Thr His Ile Gln Phe His
            260                 265                 270 agc tac ggc acc gag ggc gat aag aag ttt tct tct gcc gcg gcc aat       864
Ser Tyr Gly Thr Glu Gly Asp Lys Lys Phe Ser Ser Ala Ala Ala Asn
        275                 280                 285 att gcc gag gcc atc aac aac aac aag cat atc act gcc gat gtc ggc       912
Ile Ala Glu Ala Ile Asn Asn Asn Lys His Ile Thr Ala Asp Val Gly
    290                 295                 300 cag att ctg ttc ggc cag acc gtg aca gct tcg ggc gat aac atg atg       960
Gln Ile Leu Phe Gly Gln Thr Val Thr Ala Ser Gly Asp Asn Met Met
305                 310                 315                 320 cag cat tta aat gcc aaa gtc gcc aac ccg aaa aag tcg gtg att atg      1008
Gln His Leu Asn Ala Lys Val Ala Asn Pro Lys Lys Ser Val Ile Met
                325                 330                 335 gac att gaa tgt gat gcc ggt tgt ggc gtg gtg cct ttc aaa tac cgc      1056
Asp Ile Glu Cys Asp Ala Gly Cys Gly Val Val Pro Phe Lys Tyr Arg
            340                 345                 350 gat gaa aat tac gtc aac gcc ttg caa tgg gcg att ggc ctg gaa gtg      1104
Asp Glu Asn Tyr Val Asn Ala Leu Gln Trp Ala Ile Gly Leu Glu Val
        355                 360                 365 ttc ttg agt gta gac gat cca tgg cgc gtg ttc ctg acc aca gac cat      1152
Phe Leu Ser Val Asp Asp Pro Trp Arg Val Phe Leu Thr Thr Asp His
    370                 375                 380 ccc aat ggg gca cca ttt acc agc tat ccg cac ctg atc cgt ttg ctg      1200
Pro Asn Gly Ala Pro Phe Thr Ser Tyr Pro His Leu Ile Arg Leu Leu
385                 390                 395                 400 atg gac aaa tct ttc cgt aat gat gca ttt gat aaa ttg aac ctg gat      1248
Met Asp Lys Ser Phe Arg Asn Asp Ala Phe Asp Lys Leu Asn Leu Asp
                405                 410                 415 gcg cag gcc atg agt aac ctg aag tca ctg gat cgc gaa tac agc ctg      1296
Ala Gln Ala Met Ser Asn Leu Lys Ser Leu Asp Arg Glu Tyr Ser Leu
            420                 425                 430 tat gag atc gtc acc atg act cgc tca gcg cca gca aaa ttg att ggc      1344
Tyr Glu Ile Val Thr Met Thr Arg Ser Ala Pro Ala Lys Leu Ile Gly
        435                 440                 445
```

-continued

```
ttg caa gac cgt ggt cac tta ggt gta ggc gca gct gca gat atc acc      1392
Leu Gln Asp Arg Gly His Leu Gly Val Gly Ala Ala Ala Asp Ile Thr
    450                 455                 460 gtt tac act gat cag gct gac aaa gag gcg atg ttt gcc aag cca gac      1440
Val Tyr Thr Asp Gln Ala Asp Lys Glu Ala Met Phe Ala Lys Pro Asp
465                 470                 475                 480 ttg gtg ttt aaa gat ggc gaa ctg gtc gtt aaa gaa ggc aag gtc gtg      1488
Leu Val Phe Lys Asp Gly Glu Leu Val Val Lys Glu Gly Lys Val Val
                485                 490                 495 aaa gtg gtg tgg ggc gca acc cat acg gcc aaa cct gcc ttt gat aac      1536
Lys Val Val Trp Gly Ala Thr His Thr Ala Lys Pro Ala Phe Asp Asn
            500                 505                 510 agt gtg gaa aaa gac atc aaa caa tat ttt gac cgc tac cac acc atg      1584
Ser Val Glu Lys Asp Ile Lys Gln Tyr Phe Asp Arg Tyr His Thr Met
        515                 520                 525 caa atg caa aac ttc aaa atc agc aat gac cat att gcg gaa gat ggc      1632
Gln Met Gln Asn Phe Lys Ile Ser Asn Asp His Ile Ala Glu Asp Gly
    530                 535                 540 cgc aat cat gtg att aat cat gcg cag gga taa                          1665
Arg Asn His Val Ile Asn His Ala Gln Gly
545                 550
```

<210> SEQ ID NO 20
<211> LENGTH: 554
<212> TYPE: PRT
<213> ORGANISM: Methylophilus methylotrophus

<400> SEQUENCE: 20

```
Met Ile Thr Leu Leu Lys Asn Ala Lys Val Ile Asp Pro Ala His Asn
1               5                   10                  15

Lys Asp Gly Val Val Gln Asp Ile Tyr Ile Arg Asp Gly Arg Ile Ile
                20                  25                  30

Ala Lys Pro Ala Asp Ser Glu Lys Ile Gly Gln Ile Tyr Asp Leu Asn
            35                  40                  45

Gly Lys Ile Val Met Ala Gly Ala Ile Asp Met His Ser His Ile Gly
        50                  55                  60

Gly Gly Lys Val Asn Ile Ala Arg Met Leu Pro Glu Tyr Gln Ala
65                  70                  75                  80

Met Arg Lys Leu Glu Glu Pro Glu Ala His Ile Cys Gly Ala Asn Cys
                85                  90                  95

Ser His His Ala Thr Pro Asn Thr Thr Asp Thr Gly Met Arg Tyr Ile
            100                 105                 110

Glu Met Gly Tyr Thr Ala Ala Phe Glu Pro Ala Ile Leu Ala Val Asn
        115                 120                 125

Ala Arg Gln Ala His Met Glu Met Gly Asp Thr Pro Met Ile Asp Lys
    130                 135                 140

Gly Gly Tyr Ala Met Leu Gly Asn Asp Asp Tyr Leu Leu Arg Leu Leu
145                 150                 155                 160

Ser Gln Asn Ala Asp Gln Lys Thr Ile Asn Asp Tyr Val Ala Trp Thr
                165                 170                 175

Leu His Ala Thr Gln Thr Ile Gly Ile Lys Val Val Asn Pro Gly Gly
            180                 185                 190

Ile Ser Ala Phe Lys Phe Asn Glu Arg Arg Gln Asp Leu Asp Gln Leu
        195                 200                 205

His Ser Tyr Tyr Asn Ile Thr Pro Arg Arg Ile Leu Gln Ala Leu Ser
    210                 215                 220

Arg Ala Val Asn Glu Ile Gly Ile Ala Lys Pro Leu His Val His Cys
```

```
                225                 230                 235                 240
Asn Asn Leu Gly Val Ala Gly Asn Phe Gln Thr Thr Leu Asp Thr Met
                245                 250                 255
Gly Ala Ser Asp Gly Leu Pro Met His Leu Thr His Ile Gln Phe His
                260                 265                 270
Ser Tyr Gly Thr Glu Gly Asp Lys Lys Phe Ser Ser Ala Ala Ala Asn
                275                 280                 285
Ile Ala Glu Ala Ile Asn Asn Asn Lys His Ile Thr Ala Asp Val Gly
                290                 295                 300
Gln Ile Leu Phe Gly Gln Thr Val Thr Ala Ser Gly Asp Asn Met Met
305                 310                 315                 320
Gln His Leu Asn Ala Lys Val Ala Asn Pro Lys Lys Ser Val Ile Met
                325                 330                 335
Asp Ile Glu Cys Asp Ala Gly Cys Gly Val Val Pro Phe Lys Tyr Arg
                340                 345                 350
Asp Glu Asn Tyr Val Asn Ala Leu Gln Trp Ala Ile Gly Leu Glu Val
                355                 360                 365
Phe Leu Ser Val Asp Asp Pro Trp Arg Val Phe Leu Thr Thr Asp His
                370                 375                 380
Pro Asn Gly Ala Pro Phe Thr Ser Tyr Pro His Leu Ile Arg Leu Leu
385                 390                 395                 400
Met Asp Lys Ser Phe Arg Asn Asp Ala Phe Asp Lys Leu Asn Leu Asp
                405                 410                 415
Ala Gln Ala Met Ser Asn Leu Lys Ser Leu Asp Arg Glu Tyr Ser Leu
                420                 425                 430
Tyr Glu Ile Val Thr Met Thr Arg Ser Ala Pro Ala Lys Leu Ile Gly
                435                 440                 445
Leu Gln Asp Arg Gly His Leu Gly Val Gly Ala Ala Asp Ile Thr
                450                 455                 460
Val Tyr Thr Asp Gln Ala Asp Lys Glu Ala Met Phe Ala Lys Pro Asp
465                 470                 475                 480
Leu Val Phe Lys Asp Gly Glu Leu Val Val Lys Glu Gly Lys Val Val
                485                 490                 495
Lys Val Val Trp Gly Ala Thr His Thr Ala Lys Pro Ala Phe Asp Asn
                500                 505                 510
Ser Val Glu Lys Asp Ile Lys Gln Tyr Phe Asp Arg Tyr His Thr Met
                515                 520                 525
Gln Met Gln Asn Phe Lys Ile Ser Asn Asp His Ile Ala Glu Asp Gly
                530                 535                 540
Arg Asn His Val Ile Asn His Ala Gln Gly
545                 550
```

<210> SEQ ID NO 21
<211> LENGTH: 858
<212> TYPE: DNA
<213> ORGANISM: Methylophilus methylotrophus
<220> FEATURE:
<221> NAME/KEY: CDS
<222> LOCATION: (1)..(858)
<223> OTHER INFORMATION:

<400> SEQUENCE: 21

```
atg agc gct caa att att gat ggc aaa cag att gcc aat caa ctg tta      48
Met Ser Ala Gln Ile Ile Asp Gly Lys Gln Ile Ala Asn Gln Leu Leu
1               5                   10                  15 gaa gaa atc aaa gtc aag att gac caa cgc ctg caa gca ggg aaa cgt      96
```

-continued

| | | |
|---|---|---|
| gcc cct tgt ctt gcg gtt att tta gtt ggt gac gac gcc gcc tca gcc<br>Ala Pro Cys Leu Ala Val Ile Leu Val Gly Asp Asp Ala Ala Ser Ala<br>35 40 45 | | 144 |
| att tat gta cgc aac aaa cgg cta gcc tgc gaa aag gtc ggg att atc<br>Ile Tyr Val Arg Asn Lys Arg Leu Ala Cys Glu Lys Val Gly Ile Ile<br>50 55 60 | | 192 |
| tct gtc gca cac aat tta ccg agc agc act tca caa gaa gaa ttg ttt<br>Ser Val Ala His Asn Leu Pro Ser Ser Thr Ser Gln Glu Glu Leu Phe<br>65 70 75 80 | | 240 |
| gcc ttg att aga caa ttg aat gct gac gat gaa acc gat ggc att ctg<br>Ala Leu Ile Arg Gln Leu Asn Ala Asp Asp Glu Thr Asp Gly Ile Leu<br>85 90 95 | | 288 |
| gtg caa tcg cct ttg ccg cac cat att gat gaa aca gaa att ctt gcc<br>Val Gln Ser Pro Leu Pro His His Ile Asp Glu Thr Glu Ile Leu Ala<br>100 105 110 | | 336 |
| ctg att gac cca gcc aag gat gtg gat ggc ttt cac cca tac aat att<br>Leu Ile Asp Pro Ala Lys Asp Val Asp Gly Phe His Pro Tyr Asn Ile<br>115 120 125 | | 384 |
| ggt cgc ctg gca gtg cgt cag ccg ctg ctg cgt tcc tgc aca cct tat<br>Gly Arg Leu Ala Val Arg Gln Pro Leu Leu Arg Ser Cys Thr Pro Tyr<br>130 135 140 | | 432 |
| ggt gtg att aaa atg ctg caa gcc agc ggc atc tcc ctc aaa gga ctg<br>Gly Val Ile Lys Met Leu Gln Ala Ser Gly Ile Ser Leu Lys Gly Leu<br>145 150 155 160 | | 480 |
| gat gcg gtc gtt gtg ggc gtt tcg aac cac gtc ggg cgc cct atg ggc<br>Asp Ala Val Val Val Gly Val Ser Asn His Val Gly Arg Pro Met Gly<br>165 170 175 | | 528 |
| ctg gaa tta ctg ctg gca ggc tgc acc gtc acc agt tgc cat aga cat<br>Leu Glu Leu Leu Leu Ala Gly Cys Thr Val Thr Ser Cys His Arg His<br>180 185 190 | | 576 |
| acc aaa gat ctc gct gga cac att ggc agg gca gac ctg gtt gtg gct<br>Thr Lys Asp Leu Ala Gly His Ile Gly Arg Ala Asp Leu Val Val Ala<br>195 200 205 | | 624 |
| gcg gca ggt aaa gca ggc ctg att aaa ggt gaa tgg atc aaa cct ggc<br>Ala Ala Gly Lys Ala Gly Leu Ile Lys Gly Glu Trp Ile Lys Pro Gly<br>210 215 220 | | 672 |
| gcg att gtc gtt gat atc ggc atc aat cgc ttg ccg gat gga aaa att<br>Ala Ile Val Val Asp Ile Gly Ile Asn Arg Leu Pro Asp Gly Lys Ile<br>225 230 235 240 | | 720 |
| acc ggt gac gtg gat ttt gca gtg gcc agc caa cgt gcg agc cat atc<br>Thr Gly Asp Val Asp Phe Ala Val Ala Ser Gln Arg Ala Ser His Ile<br>245 250 255 | | 768 |
| aca ccc gtc cct ggc ggc gta ggg ccg atg act gtt gcc acg ctc atg<br>Thr Pro Val Pro Gly Gly Val Gly Pro Met Thr Val Ala Thr Leu Met<br>260 265 270 | | 816 |
| gaa aac act tta aaa gcg cta gaa gtt agg gag cag gct taa<br>Glu Asn Thr Leu Lys Ala Leu Glu Val Arg Glu Gln Ala<br>275 280 285 | | 858 |

<210> SEQ ID NO 22
<211> LENGTH: 285
<212> TYPE: PRT
<213> ORGANISM: Methylophilus methylotrophus

<400> SEQUENCE: 22

Met Ser Ala Gln Ile Ile Asp Gly Lys Gln Ile Ala Asn Gln Leu Leu
1               5                   10                  15

Glu Glu Ile Lys Val Lys Ile Asp Gln Arg Leu Gln Ala Gly Lys Arg

-continued

```
                20                  25                  30
Ala Pro Cys Leu Ala Val Ile Leu Val Gly Asp Asp Ala Ser Ala
             35                  40                  45
Ile Tyr Val Arg Asn Lys Arg Leu Ala Cys Glu Lys Val Gly Ile Ile
 50                  55                  60
Ser Val Ala His Asn Leu Pro Ser Ser Thr Ser Gln Glu Glu Leu Phe
 65                  70                  75                  80
Ala Leu Ile Arg Gln Leu Asn Ala Asp Asp Glu Thr Asp Gly Ile Leu
                 85                  90                  95
Val Gln Ser Pro Leu Pro His His Ile Asp Glu Thr Glu Ile Leu Ala
            100                 105                 110
Leu Ile Asp Pro Ala Lys Asp Val Asp Gly Phe His Pro Tyr Asn Ile
            115                 120                 125
Gly Arg Leu Ala Val Arg Gln Pro Leu Leu Arg Ser Cys Thr Pro Tyr
            130                 135                 140
Gly Val Ile Lys Met Leu Gln Ala Ser Gly Ile Ser Leu Lys Gly Leu
145                 150                 155                 160
Asp Ala Val Val Val Gly Val Ser Asn His Val Gly Arg Pro Met Gly
                165                 170                 175
Leu Glu Leu Leu Leu Ala Gly Cys Thr Val Thr Ser Cys His Arg His
            180                 185                 190
Thr Lys Asp Leu Ala Gly His Ile Gly Arg Ala Asp Leu Val Val Ala
            195                 200                 205
Ala Ala Gly Lys Ala Gly Leu Ile Lys Gly Glu Trp Ile Lys Pro Gly
            210                 215                 220
Ala Ile Val Val Asp Ile Gly Ile Asn Arg Leu Pro Asp Gly Lys Ile
225                 230                 235                 240
Thr Gly Asp Val Asp Phe Ala Val Ala Ser Gln Arg Ala Ser His Ile
                245                 250                 255
Thr Pro Val Pro Gly Gly Val Gly Pro Met Thr Val Ala Thr Leu Met
            260                 265                 270
Glu Asn Thr Leu Lys Ala Leu Glu Val Arg Glu Gln Ala
            275                 280                 285
```

<210> SEQ ID NO 23
<211> LENGTH: 1650
<212> TYPE: DNA
<213> ORGANISM: Methylophilus methylotrophus
<220> FEATURE:
<221> NAME/KEY: CDS
<222> LOCATION: (1)..(1650)
<223> OTHER INFORMATION:

<400> SEQUENCE: 23

```
atg ctt agc gat atc gag ata gct cag gcc gca acg cta aag ccc atc        48
Met Leu Ser Asp Ile Glu Ile Ala Gln Ala Ala Thr Leu Lys Pro Ile
 1               5                  10                  15 gtg gac atc gct ggc aaa atc ggg ctt tct gca ggc gat ttg cat gcc        96
Val Asp Ile Ala Gly Lys Ile Gly Leu Ser Ala Gly Asp Leu His Ala
                20                  25                  30 ttt ggc cca cat atg gcc aaa ttg aac cag gcg acc atc aat cgc ttg       144
Phe Gly Pro His Met Ala Lys Leu Asn Gln Ala Thr Ile Asn Arg Leu
             35                  40                  45 tac gac cag ccc gcc aaa gcc aaa ttg atc ctg gtc acc gcc att aac       192
Tyr Asp Gln Pro Ala Lys Ala Lys Leu Ile Leu Val Thr Ala Ile Asn
 50                  55                  60 ccc acg ccg gca ggc gaa ggc aaa acc act aca acc ata ggc ctc acg       240
```

```
Pro Thr Pro Ala Gly Glu Gly Lys Thr Thr Thr Thr Ile Gly Leu Thr
 65                  70                  75                  80 gac gct tta aat cgt gca ggg tat cat gcg atg gca tgc ctg cgc gag      288
Asp Ala Leu Asn Arg Ala Gly Tyr His Ala Met Ala Cys Leu Arg Glu
                     85                  90                  95 cct tct ctg ggg ccg gta ttt ggc atg aaa ggc ggc gcc act ggc ggc      336
Pro Ser Leu Gly Pro Val Phe Gly Met Lys Gly Gly Ala Thr Gly Gly
            100                 105                 110 ggc tac gca cag gtg gtc ccc atg gaa aac atc aac ttg cat ttt acc      384
Gly Tyr Ala Gln Val Val Pro Met Glu Asn Ile Asn Leu His Phe Thr
        115                 120                 125 ggt gac ttt cat gcc atc agt gcc gcc aat aac ctg ctg gca gcc ctg      432
Gly Asp Phe His Ala Ile Ser Ala Ala Asn Asn Leu Leu Ala Ala Leu
130                 135                 140 att gat aat cat att tac cat ggc aat acg tta cag ttt gat acc gtg      480
Ile Asp Asn His Ile Tyr His Gly Asn Thr Leu Gln Phe Asp Thr Val
145                 150                 155                 160 agc tgg cgg cgt tgc atg gat atg aat gac cgg gct ttg cgc cgg att      528
Ser Trp Arg Arg Cys Met Asp Met Asn Asp Arg Ala Leu Arg Arg Ile
                    165                 170                 175 acc atc aac cag ccc acc tcg tat gac act ggt ttt gat atc aca gtc      576
Thr Ile Asn Gln Pro Thr Ser Tyr Asp Thr Gly Phe Asp Ile Thr Val
                180                 185                 190 gcc agt gag gtc atg gcg att ttt tgc ctg gcg acc gat cta gca gat      624
Ala Ser Glu Val Met Ala Ile Phe Cys Leu Ala Thr Asp Leu Ala Asp
            195                 200                 205 tta acg cgc agg ctg gga cgt atc cag gta ggg gtg tcg gta cag ggg      672
Leu Thr Arg Arg Leu Gly Arg Ile Gln Val Gly Val Ser Val Gln Gly
210                 215                 220 cag cct ata ttg gcc agc gac ctg caa gcc gaa ggc gcg atg acg gct      720
Gln Pro Ile Leu Ala Ser Asp Leu Gln Ala Glu Gly Ala Met Thr Ala
225                 230                 235                 240 ttg cta aaa gat gca ttt cag ccc aac ctg gta cag acg ctg gaa ggc      768
Leu Leu Lys Asp Ala Phe Gln Pro Asn Leu Val Gln Thr Leu Glu Gly
                    245                 250                 255 tcg ccg gct ttg gtg cat ggt ggc cca ttc gcc aat atc gcg cat ggt      816
Ser Pro Ala Leu Val His Gly Gly Pro Phe Ala Asn Ile Ala His Gly
                260                 265                 270 tgt aat tcg ctg gtt gcc acc caa acc gcc tta cgc ctg acg gat tat      864
Cys Asn Ser Leu Val Ala Thr Gln Thr Ala Leu Arg Leu Thr Asp Tyr
            275                 280                 285 gtg gtc act gaa gca ggg ttt ggt gca gat ttg ggc gcc gag aag ttt      912
Val Val Thr Glu Ala Gly Phe Gly Ala Asp Leu Gly Ala Glu Lys Phe
290                 295                 300 atg gat atc aaa tgc cgt cag tct ggc ttg cga cca gat gtt gct gtg      960
Met Asp Ile Lys Cys Arg Gln Ser Gly Leu Arg Pro Asp Val Ala Val
305                 310                 315                 320 att gta gcg act gta cgt gct ttg aaa tat aac ggt ggc gtg gag gtg     1008
Ile Val Ala Thr Val Arg Ala Leu Lys Tyr Asn Gly Gly Val Glu Val
                    325                 330                 335 gct gac ctc aat acc gaa aac ctg gtg gct ctt tct att ggt gtc gcc     1056
Ala Asp Leu Asn Thr Glu Asn Leu Val Ala Leu Ser Ile Gly Val Ala
                340                 345                 350 aat cta aaa aaa cat gtg gtc aat ctg cga cag cac ttt ggt ttg ccc     1104
Asn Leu Lys Lys His Val Val Asn Leu Arg Gln His Phe Gly Leu Pro
            355                 360                 365 gtg gtg gtg gca ttg aat cat ttc act gcg gat acc gag act gaa att     1152
Val Val Val Ala Leu Asn His Phe Thr Ala Asp Thr Glu Thr Glu Ile
370                 375                 380
```

| | | |
|---|---|---|
| gcc ctg gtt caa gcg gcg gtg gcg tct ctg ggt gcc agc ctg cat gtg<br>Ala Leu Val Gln Ala Ala Val Ala Ser Leu Gly Ala Ser Leu His Val<br>385                                390                          395                         400 | 1200 |
| tgc agg cat tgg gcg caa ggt gga gcg ggt gct ttg tcg ctg gca cag<br>Cys Arg His Trp Ala Gln Gly Gly Ala Gly Ala Leu Ser Leu Ala Gln<br>                                  405                              410                         415 | 1248 |
| gct gtt gcc acg caa gca caa cag tca gcc aaa cca acg tta ctt tat<br>Ala Val Ala Thr Gln Ala Gln Gln Ser Ala Lys Pro Thr Leu Leu Tyr<br>                  420                              425                              430 | 1296 |
| gca gat gac ttg cca ttg aca gaa aaa ctc aac acg ctg gct aaa aat<br>Ala Asp Asp Leu Pro Leu Thr Glu Lys Leu Asn Thr Leu Ala Lys Asn<br>                                  435                              440                         445 | 1344 |
| atc tat ggt gcc agt gcc gtc act ttt agt gag cgg gcc caa cag caa<br>Ile Tyr Gly Ala Ser Ala Val Thr Phe Ser Glu Arg Ala Gln Gln Gln<br>450                              455                          460 | 1392 |
| tta gtg aat atg gct gaa gcc agc ctg ggc ttg ccg gtc tgt gtg gcc<br>Leu Val Asn Met Ala Glu Ala Ser Leu Gly Leu Pro Val Cys Val Ala<br>465                              470                            475                         480 | 1440 |
| aag act cag tat tcg tta tcc tgt gat gcc agc ttg cgt aat gta cca<br>Lys Thr Gln Tyr Ser Leu Ser Cys Asp Ala Ser Leu Arg Asn Val Pro<br>                  485                              490                         495 | 1488 |
| gag cat cat gtc ctg cat gtg cgc gaa ttg cgt ttg tcg cgc ggg gct<br>Glu His His Val Leu His Val Arg Glu Leu Arg Leu Ser Arg Gly Ala<br>                                  500                              505                         510 | 1536 |
| ggc ttt gtc gtg gcc att tgc ggc gat atc atg acc atg ccc ggt ttg<br>Gly Phe Val Val Ala Ile Cys Gly Asp Ile Met Thr Met Pro Gly Leu<br>                  515                              520                         525 | 1584 |
| cca aaa cag cct gcc agt ggt cgc atc agc gta gat gcc agt ggt aaa<br>Pro Lys Gln Pro Ala Ser Gly Arg Ile Ser Val Asp Ala Ser Gly Lys<br>530                              535                          540 | 1632 |
| ata aag gga ctt tcc tga<br>Ile Lys Gly Leu Ser<br>545 | 1650 |

<210> SEQ ID NO 24
<211> LENGTH: 549
<212> TYPE: PRT
<213> ORGANISM: Methylophilus methylotrophus

<400> SEQUENCE: 24

Met Leu Ser Asp Ile Glu Ile Ala Gln Ala Ala Thr Leu Lys Pro Ile
1                 5                   10                 15

Val Asp Ile Ala Gly Lys Ile Gly Leu Ser Ala Gly Asp Leu His Ala
                 20                   25                 30

Phe Gly Pro His Met Ala Lys Leu Asn Gln Ala Thr Ile Asn Arg Leu
                 35                   40                 45

Tyr Asp Gln Pro Ala Lys Ala Lys Leu Ile Leu Val Thr Ala Ile Asn
    50                   55                   60

Pro Thr Pro Ala Gly Glu Gly Lys Thr Thr Thr Ile Gly Leu Thr
65                  70                   75                   80

Asp Ala Leu Asn Arg Ala Gly Tyr His Ala Met Ala Cys Leu Arg Glu
                 85                   90                 95

Pro Ser Leu Gly Pro Val Phe Gly Met Lys Gly Gly Ala Thr Gly Gly
                 100                 105                110

Gly Tyr Ala Gln Val Val Pro Met Glu Asn Ile Asn Leu His Phe Thr
            115                 120                125

Gly Asp Phe His Ala Ile Ser Ala Ala Asn Asn Leu Leu Ala Ala Leu
     130                 135                 140

```
Ile Asp Asn His Ile Tyr His Gly Asn Thr Leu Gln Phe Asp Thr Val
145                 150                 155                 160

Ser Trp Arg Arg Cys Met Asp Met Asn Asp Arg Ala Leu Arg Arg Ile
                165                 170                 175

Thr Ile Asn Gln Pro Thr Ser Tyr Asp Thr Gly Phe Asp Ile Thr Val
            180                 185                 190

Ala Ser Glu Val Met Ala Ile Phe Cys Leu Ala Thr Asp Leu Ala Asp
        195                 200                 205

Leu Thr Arg Arg Leu Gly Arg Ile Gln Val Gly Val Ser Val Gln Gly
    210                 215                 220

Gln Pro Ile Leu Ala Ser Asp Leu Gln Ala Glu Gly Ala Met Thr Ala
225                 230                 235                 240

Leu Leu Lys Asp Ala Phe Gln Pro Asn Leu Val Gln Thr Leu Glu Gly
                245                 250                 255

Ser Pro Ala Leu Val His Gly Gly Pro Phe Ala Asn Ile Ala His Gly
            260                 265                 270

Cys Asn Ser Leu Val Ala Thr Gln Thr Ala Leu Arg Leu Thr Asp Tyr
        275                 280                 285

Val Val Thr Glu Ala Gly Phe Gly Ala Asp Leu Gly Ala Glu Lys Phe
    290                 295                 300

Met Asp Ile Lys Cys Arg Gln Ser Gly Leu Arg Pro Asp Val Ala Val
305                 310                 315                 320

Ile Val Ala Thr Val Arg Ala Leu Lys Tyr Asn Gly Gly Val Glu Val
                325                 330                 335

Ala Asp Leu Asn Thr Glu Asn Leu Val Ala Leu Ser Ile Gly Val Ala
            340                 345                 350

Asn Leu Lys Lys His Val Val Asn Leu Arg Gln His Phe Gly Leu Pro
        355                 360                 365

Val Val Val Ala Leu Asn His Phe Thr Ala Asp Thr Glu Thr Glu Ile
    370                 375                 380

Ala Leu Val Gln Ala Ala Val Ala Ser Leu Gly Ala Ser Leu His Val
385                 390                 395                 400

Cys Arg His Trp Ala Gln Gly Gly Ala Gly Ala Leu Ser Leu Ala Gln
                405                 410                 415

Ala Val Ala Thr Gln Ala Gln Gln Ser Ala Lys Pro Thr Leu Leu Tyr
            420                 425                 430

Ala Asp Asp Leu Pro Leu Thr Glu Lys Leu Asn Thr Leu Ala Lys Asn
        435                 440                 445

Ile Tyr Gly Ala Ser Ala Val Thr Phe Ser Glu Arg Ala Gln Gln Gln
    450                 455                 460

Leu Val Asn Met Ala Glu Ala Ser Leu Gly Leu Pro Val Cys Val Ala
465                 470                 475                 480

Lys Thr Gln Tyr Ser Leu Ser Cys Asp Ala Ser Leu Arg Asn Val Pro
                485                 490                 495

Glu His His Val Leu His Val Arg Glu Leu Arg Leu Ser Arg Gly Ala
            500                 505                 510

Gly Phe Val Val Ala Ile Cys Gly Asp Ile Met Thr Met Pro Gly Leu
        515                 520                 525

Pro Lys Gln Pro Ala Ser Gly Arg Ile Ser Val Asp Ala Ser Gly Lys
    530                 535                 540

Ile Lys Gly Leu Ser
545
```

-continued

```
<210> SEQ ID NO 25
<211> LENGTH: 927
<212> TYPE: DNA
<213> ORGANISM: Methylophilus methylotrophus
<220> FEATURE:
<221> NAME/KEY: CDS
<222> LOCATION: (1)..(927)
<223> OTHER INFORMATION:

<400> SEQUENCE: 25 atg att att aat gga gta gag atc gat gat acc ttt gcc gaa gca ttc         48
Met Ile Ile Asn Gly Val Glu Ile Asp Asp Thr Phe Ala Glu Ala Phe
1               5                   10                  15 aat atg cgc ggc aca cgt atc ctg att acc gcg caa aac ctg cgc tgg         96
Asn Met Arg Gly Thr Arg Ile Leu Ile Thr Ala Gln Asn Leu Arg Trp
            20                  25                  30 gcg tat aac gcc gcc aat gcc atg act ggc ttt gcc acc agc gta att        144
Ala Tyr Asn Ala Ala Asn Ala Met Thr Gly Phe Ala Thr Ser Val Ile
        35                  40                  45 ggc tgt ggg gta gag gct ggc ata gaa cgt gag ttg agc gag gac gaa        192
Gly Cys Gly Val Glu Ala Gly Ile Glu Arg Glu Leu Ser Glu Asp Glu
    50                  55                  60 acc ccc gat ggc cgt cca ggc gtc agt gtg ctg atg ttt gcc atg ggc        240
Thr Pro Asp Gly Arg Pro Gly Val Ser Val Leu Met Phe Ala Met Gly
65                  70                  75                  80 agc aag gtg ctg atg cag cag ctt gaa aca cgc atg ggc caa tgc att        288
Ser Lys Val Leu Met Gln Gln Leu Glu Thr Arg Met Gly Gln Cys Ile
                85                  90                  95 ttg acg tgc ccc acc gcg gct gcg ttt gcg ggt atc gag tct gaa gac        336
Leu Thr Cys Pro Thr Ala Ala Ala Phe Ala Gly Ile Glu Ser Glu Asp
            100                 105                 110 atg att agc ctc ggc aag cat ttg cga ttt ttt ggc gat ggc tac cag        384
Met Ile Ser Leu Gly Lys His Leu Arg Phe Phe Gly Asp Gly Tyr Gln
        115                 120                 125 gtg tcc aag caa att ccg gat gcc aac ggc aaa ctc aaa cgc tac tgg        432
Val Ser Lys Gln Ile Pro Asp Ala Asn Gly Lys Leu Lys Arg Tyr Trp
    130                 135                 140 cgt atc ccg gtg atg gat ggt gaa ttt tta act gaa gaa acc act ggg        480
Arg Ile Pro Val Met Asp Gly Glu Phe Leu Thr Glu Glu Thr Thr Gly
145                 150                 155                 160 atg gtg cgc gcc att ggt ggc ggt aac ttc ctg gtg ctg ggg gcc agc        528
Met Val Arg Ala Ile Gly Gly Gly Asn Phe Leu Val Leu Gly Ala Ser
                165                 170                 175 cag gcg caa gtg ctc acc gcc tgt gaa gcg gcg atc gac gcc atg cgc        576
Gln Ala Gln Val Leu Thr Ala Cys Glu Ala Ala Ile Asp Ala Met Arg
            180                 185                 190 aaa ttg ccc aat gtg att atg cct ttc ccg ggc ggg gtg gtg cgt tcc        624
Lys Leu Pro Asn Val Ile Met Pro Phe Pro Gly Gly Val Val Arg Ser
        195                 200                 205 ggc tcc aag gtt ggc agc aag tac cct aaa atg ttt gcc agt acc aat        672
Gly Ser Lys Val Gly Ser Lys Tyr Pro Lys Met Phe Ala Ser Thr Asn
    210                 215                 220 gat gcg ttc tgc ccg acc cta aaa ggg gtc gtg aaa agc gaa ctg gat        720
Asp Ala Phe Cys Pro Thr Leu Lys Gly Val Val Lys Ser Glu Leu Asp
225                 230                 235                 240 cca cgc gtg gaa agc gtg atg gaa att gtc gtc aac gga ctg acg ttt        768
Pro Arg Val Glu Ser Val Met Glu Ile Val Val Asn Gly Leu Thr Phe
                245                 250                 255 gaa gat att gcg gtt tct atg aag gca ggc atc gaa gcg gct tgt agc        816
Glu Asp Ile Ala Val Ser Met Lys Ala Gly Ile Glu Ala Ala Cys Ser
            260                 265                 270
```

```
ctg ggt aaa gac aat ggc atc ctg cgc att tct gct ggt aac tac ggc     864
Leu Gly Lys Asp Asn Gly Ile Leu Arg Ile Ser Ala Gly Asn Tyr Gly
        275                 280                 285 ggc aag ctg ggc cag cat cat ttt aaa tta cgc cca att tta agc ggg     912
Gly Lys Leu Gly Gln His His Phe Lys Leu Arg Pro Ile Leu Ser Gly
        290                 295                 300 gag gtg acc gca tga                                                 927
Glu Val Thr Ala
305
```

<210> SEQ ID NO 26
<211> LENGTH: 308
<212> TYPE: PRT
<213> ORGANISM: Methylophilus methylotrophus

<400> SEQUENCE: 26

```
Met Ile Ile Asn Gly Val Glu Ile Asp Asp Thr Phe Ala Glu Ala Phe
1               5                   10                  15

Asn Met Arg Gly Thr Arg Ile Leu Ile Thr Ala Gln Asn Leu Arg Trp
            20                  25                  30

Ala Tyr Asn Ala Ala Asn Ala Met Thr Gly Phe Ala Thr Ser Val Ile
        35                  40                  45

Gly Cys Gly Val Glu Ala Gly Ile Glu Arg Glu Leu Ser Glu Asp Glu
    50                  55                  60

Thr Pro Asp Gly Arg Pro Gly Val Ser Val Leu Met Phe Ala Met Gly
65                  70                  75                  80

Ser Lys Val Leu Met Gln Gln Leu Glu Thr Arg Met Gly Gln Cys Ile
                85                  90                  95

Leu Thr Cys Pro Thr Ala Ala Ala Phe Ala Gly Ile Glu Ser Glu Asp
            100                 105                 110

Met Ile Ser Leu Gly Lys His Leu Arg Phe Phe Gly Asp Gly Tyr Gln
        115                 120                 125

Val Ser Lys Gln Ile Pro Asp Ala Asn Gly Lys Leu Lys Arg Tyr Trp
    130                 135                 140

Arg Ile Pro Val Met Asp Gly Glu Phe Leu Thr Glu Thr Thr Gly
145                 150                 155                 160

Met Val Arg Ala Ile Gly Gly Asn Phe Leu Val Leu Gly Ala Ser
                165                 170                 175

Gln Ala Gln Val Leu Thr Ala Cys Glu Ala Ala Ile Asp Ala Met Arg
            180                 185                 190

Lys Leu Pro Asn Val Ile Met Pro Phe Pro Gly Gly Val Val Arg Ser
        195                 200                 205

Gly Ser Lys Val Gly Ser Lys Tyr Pro Lys Met Phe Ala Ser Thr Asn
    210                 215                 220

Asp Ala Phe Cys Pro Thr Leu Lys Gly Val Val Lys Ser Glu Leu Asp
225                 230                 235                 240

Pro Arg Val Glu Ser Val Met Glu Ile Val Val Asn Gly Leu Thr Phe
                245                 250                 255

Glu Asp Ile Ala Val Ser Met Lys Ala Gly Ile Glu Ala Ala Cys Ser
            260                 265                 270

Leu Gly Lys Asp Asn Gly Ile Leu Arg Ile Ser Ala Gly Asn Tyr Gly
        275                 280                 285

Gly Lys Leu Gly Gln His His Phe Lys Leu Arg Pro Ile Leu Ser Gly
    290                 295                 300

Glu Val Thr Ala
305
```

<210> SEQ ID NO 27
<211> LENGTH: 501
<212> TYPE: DNA
<213> ORGANISM: Methylophilus methylotrophus
<220> FEATURE:
<221> NAME/KEY: CDS
<222> LOCATION: (1)..(501)
<223> OTHER INFORMATION:

<400> SEQUENCE: 27

```
atg gtt gga tgt gag gtc ggt ttg gat aac aca tta agc aat gag caa      48
Met Val Gly Cys Glu Val Gly Leu Asp Asn Thr Leu Ser Asn Glu Gln
1               5                   10                  15 cac gcg caa ata caa gcg cat att caa gca cac cag cat gtg cca ggc      96
His Ala Gln Ile Gln Ala His Ile Gln Ala His Gln His Val Pro Gly
            20                  25                  30 ggg tta atg cct ttg tta cat gcg att cag gac gat att ggc tat gtc     144
Gly Leu Met Pro Leu Leu His Ala Ile Gln Asp Asp Ile Gly Tyr Val
        35                  40                  45 cct gag ctg gtg tat ccc gag att gcc aaa gcg ctg gcc ctg tca gtg     192
Pro Glu Leu Val Tyr Pro Glu Ile Ala Lys Ala Leu Ala Leu Ser Val
50                  55                  60 gca gag gtc cat ggc gtc gtc act ttt tac cat cat ttc cgt acc cac     240
Ala Glu Val His Gly Val Val Thr Phe Tyr His His Phe Arg Thr His
65                  70                  75                  80 ccc atc ggt aaa cat gtt ttg cag gtt tgc cgt gcg gag tcc tgc cag     288
Pro Ile Gly Lys His Val Leu Gln Val Cys Arg Ala Glu Ser Cys Gln
                85                  90                  95 tcc atg ggt tcc gaa aaa atg gag gct gaa ctc aaa gca aaa ctc ggt     336
Ser Met Gly Ser Glu Lys Met Glu Ala Glu Leu Lys Ala Lys Leu Gly
            100                 105                 110 gtg gat tac cat cag acc act gct gac ggt agt gtg act cta tta cct     384
Val Asp Tyr His Gln Thr Thr Ala Asp Gly Ser Val Thr Leu Leu Pro
        115                 120                 125 gtc tat tgc ctg ggg aac tgt ggc tgt tcg cca gcc gtg atg ctc gac     432
Val Tyr Cys Leu Gly Asn Cys Gly Cys Ser Pro Ala Val Met Leu Asp
130                 135                 140 gat gaa gtc tat ggg cgc atg aat aca gaa aaa gtg acc gag ttg att     480
Asp Glu Val Tyr Gly Arg Met Asn Thr Glu Lys Val Thr Glu Leu Ile
145                 150                 155                 160 gca gag gtg tgc cat ggt taa                                         501
Ala Glu Val Cys His Gly
                165
```

<210> SEQ ID NO 28
<211> LENGTH: 166
<212> TYPE: PRT
<213> ORGANISM: Methylophilus methylotrophus

<400> SEQUENCE: 28

```
Met Val Gly Cys Glu Val Gly Leu Asp Asn Thr Leu Ser Asn Glu Gln
1               5                   10                  15

His Ala Gln Ile Gln Ala His Ile Gln Ala His Gln His Val Pro Gly
            20                  25                  30

Gly Leu Met Pro Leu Leu His Ala Ile Gln Asp Asp Ile Gly Tyr Val
        35                  40                  45

Pro Glu Leu Val Tyr Pro Glu Ile Ala Lys Ala Leu Ala Leu Ser Val
    50                  55                  60

Ala Glu Val His Gly Val Val Thr Phe Tyr His His Phe Arg Thr His
65                  70                  75                  80
```

```
Pro Ile Gly Lys His Val Leu Gln Val Cys Arg Ala Glu Ser Cys Gln
                85                  90                  95

Ser Met Gly Ser Glu Lys Met Glu Ala Glu Leu Lys Ala Lys Leu Gly
            100                 105                 110

Val Asp Tyr His Gln Thr Thr Ala Asp Gly Ser Val Thr Leu Leu Pro
        115                 120                 125

Val Tyr Cys Leu Gly Asn Cys Gly Cys Ser Pro Ala Val Met Leu Asp
    130                 135                 140

Asp Glu Val Tyr Gly Arg Met Asn Thr Glu Lys Val Thr Glu Leu Ile
145                 150                 155                 160

Ala Glu Val Cys His Gly
                165

<210> SEQ ID NO 29
<211> LENGTH: 219
<212> TYPE: DNA
<213> ORGANISM: Methylophilus methylotrophus
<220> FEATURE:
<221> NAME/KEY: CDS
<222> LOCATION: (1)..(219)
<223> OTHER INFORMATION:

<400> SEQUENCE: 29 atg gaa gtg gaa aag tta atc aaa atg gcc aac cag att ggc gat ttt     48
Met Glu Val Glu Lys Leu Ile Lys Met Ala Asn Gln Ile Gly Asp Phe
1               5                   10                  15 ttt gag gca aat cca gat gtt gaa gag gca aag cgg gaa att gcc agt     96
Phe Glu Ala Asn Pro Asp Val Glu Glu Ala Lys Arg Glu Ile Ala Ser
                20                  25                  30 cac ctg aag aag ttt tgg aat tcg atc atg att aaa act ctg gtg gcg    144
His Leu Lys Lys Phe Trp Asn Ser Ile Met Ile Lys Thr Leu Val Ala
            35                  40                  45 cat gtg cag caa cag cag ggg cag ggt ttg cat ccc aaa gtg att gct    192
His Val Gln Gln Gln Gln Gly Gln Gly Leu His Pro Lys Val Ile Ala
        50                  55                  60 gcg att cag caa cat ttg cat ctc tga                                219
Ala Ile Gln Gln His Leu His Leu
65                  70

<210> SEQ ID NO 30
<211> LENGTH: 72
<212> TYPE: PRT
<213> ORGANISM: Methylophilus methylotrophus

<400> SEQUENCE: 30

Met Glu Val Glu Lys Leu Ile Lys Met Ala Asn Gln Ile Gly Asp Phe
1               5                   10                  15

Phe Glu Ala Asn Pro Asp Val Glu Glu Ala Lys Arg Glu Ile Ala Ser
                20                  25                  30

His Leu Lys Lys Phe Trp Asn Ser Ile Met Ile Lys Thr Leu Val Ala
            35                  40                  45

His Val Gln Gln Gln Gln Gly Gln Gly Leu His Pro Lys Val Ile Ala
        50                  55                  60

Ala Ile Gln Gln His Leu His Leu
65                  70

<210> SEQ ID NO 31
<211> LENGTH: 900
<212> TYPE: DNA
<213> ORGANISM: Methylophilus methylotrophus
```

<220> FEATURE:
<221> NAME/KEY: CDS
<222> LOCATION: (1)..(900)
<223> OTHER INFORMATION:

<400> SEQUENCE: 31

| | | | | | | | | | | | | | | | | |
|---|---|---|---|---|---|---|---|---|---|---|---|---|---|---|---|---|
| gtg | gaa | gtc | tta | aac | gag | cag | gat | tgt | gcg | ctg | cct | gac | agt | caa | gaa | 48 |
| Val | Glu | Val | Leu | Asn | Glu | Gln | Asp | Cys | Ala | Leu | Pro | Asp | Ser | Gln | Glu | |
| 1 | | | | 5 | | | | | 10 | | | | | 15 | | |
| tgg | cag | cct | att | ctt | gca | gag | cag | gca | gcg | gct | acg | gtg | atc | gtc | acg | 96 |
| Trp | Gln | Pro | Ile | Leu | Ala | Glu | Gln | Ala | Ala | Ala | Thr | Val | Ile | Val | Thr | |
| | | | 20 | | | | | 25 | | | | | 30 | | | |
| cga | tgg | cgt | gaa | gat | caa | tcc | acc | act | gtg | gca | gat | gcg | ttg | gcg | cag | 144 |
| Arg | Trp | Arg | Glu | Asp | Gln | Ser | Thr | Thr | Val | Ala | Asp | Ala | Leu | Ala | Gln | |
| | | 35 | | | | | 40 | | | | | 45 | | | | |
| gaa | gta | cct | gtt | gcg | ctg | ata | tat | aac | ggt | att | tcg | tat | gta | gtg | atg | 192 |
| Glu | Val | Pro | Val | Ala | Leu | Ile | Tyr | Asn | Gly | Ile | Ser | Tyr | Val | Val | Met | |
| | 50 | | | | | 55 | | | | | 60 | | | | | |
| ctg | gca | aca | ccg | gcg | gat | ctt | gag | gat | ttt | gct | tat | ggt | ttt | tca | ttt | 240 |
| Leu | Ala | Thr | Pro | Ala | Asp | Leu | Glu | Asp | Phe | Ala | Tyr | Gly | Phe | Ser | Phe | |
| 65 | | | | | 70 | | | | | 75 | | | | | 80 | |
| act | gaa | ggc | att | atc | act | gaa | cgc | ggc | caa | atc | tat | ggc | gta | gaa | gcc | 288 |
| Thr | Glu | Gly | Ile | Ile | Thr | Glu | Arg | Gly | Gln | Ile | Tyr | Gly | Val | Glu | Ala | |
| | | | | 85 | | | | | 90 | | | | | 95 | | |
| aga | gca | ttg | acg | cag | gca | gat | ggt | caa | ttg | caa | gga | ata | gaa | ctg | cat | 336 |
| Arg | Ala | Leu | Thr | Gln | Ala | Asp | Gly | Gln | Leu | Gln | Gly | Ile | Glu | Leu | His | |
| | | | 100 | | | | | 105 | | | | | 110 | | | |
| att | gac | ctg | gcg | aca | gag | caa | ttt | gtc | gcg | ctc | aag | gca | cag | cgg | cgc | 384 |
| Ile | Asp | Leu | Ala | Thr | Glu | Gln | Phe | Val | Ala | Leu | Lys | Ala | Gln | Arg | Arg | |
| | | 115 | | | | | 120 | | | | | 125 | | | | |
| aat | tta | acc | ggt | cgc | acc | gga | tgt | ggg | ttg | tgt | ggt | gcc | gag | agt | ttg | 432 |
| Asn | Leu | Thr | Gly | Arg | Thr | Gly | Cys | Gly | Leu | Cys | Gly | Ala | Glu | Ser | Leu | |
| | 130 | | | | | 135 | | | | | 140 | | | | | |
| cag | cag | gtt | ttt | aaa | caa | ccc | atg | cca | gcc | agt | ggc | cct | ctg | gtg | tca | 480 |
| Gln | Gln | Val | Phe | Lys | Gln | Pro | Met | Pro | Ala | Ser | Gly | Pro | Leu | Val | Ser | |
| 145 | | | | | 150 | | | | | 155 | | | | | 160 | |
| ctg | tca | tta | acc | gcg | cta | gag | gcc | gca | ttg | gat | gga | ttg | aag | acc | cgt | 528 |
| Leu | Ser | Leu | Thr | Ala | Leu | Glu | Ala | Ala | Leu | Asp | Gly | Leu | Lys | Thr | Arg | |
| | | | | 165 | | | | | 170 | | | | | 175 | | |
| cag | ccg | cta | cag | ctg | ctg | acg | ggt | gct | acg | cat | gcg | agc | gct | atc | gca | 576 |
| Gln | Pro | Leu | Gln | Leu | Leu | Thr | Gly | Ala | Thr | His | Ala | Ser | Ala | Ile | Ala | |
| | | | 180 | | | | | 185 | | | | | 190 | | | |
| gat | gca | cac | ggg | caa | gtg | gta | tgc | gtg | cgg | gaa | gat | gtt | ggc | cgc | cac | 624 |
| Asp | Ala | His | Gly | Gln | Val | Val | Cys | Val | Arg | Glu | Asp | Val | Gly | Arg | His | |
| | | 195 | | | | | 200 | | | | | 205 | | | | |
| aat | gcg | ctt | gat | aaa | ctg | ata | ggt | ggc | ttg | ttg | cgt | caa | ggc | cat | gat | 672 |
| Asn | Ala | Leu | Asp | Lys | Leu | Ile | Gly | Gly | Leu | Leu | Arg | Gln | Gly | His | Asp | |
| | 210 | | | | | 215 | | | | | 220 | | | | | |
| ttt | tcc | gta | ttc | tgg | gcg | acg | cat | tgg | gta | tta | acc | acc | agc | cgt | gca | 720 |
| Phe | Ser | Val | Phe | Trp | Ala | Thr | His | Trp | Val | Leu | Thr | Thr | Ser | Arg | Ala | |
| 225 | | | | | 230 | | | | | 235 | | | | | 240 | |
| agt | tac | gaa | atg | gtt | cag | aaa | gtg | gct | gtc | tgt | ggc | gga | agg | gca | ttg | 768 |
| Ser | Tyr | Glu | Met | Val | Gln | Lys | Val | Ala | Val | Cys | Gly | Gly | Arg | Ala | Leu | |
| | | | | 245 | | | | | 250 | | | | | 255 | | |
| gtt | gca | ttg | tca | gcc | ccg | aca | gcg | ctt | gct | gtc | agt | ttg | gca | aat | gaa | 816 |
| Val | Ala | Leu | Ser | Ala | Pro | Thr | Ala | Leu | Ala | Val | Ser | Leu | Ala | Asn | Glu | |
| | | | 260 | | | | | 265 | | | | | 270 | | | |
| tat | gat | ttt | ttg | ctg | gtt | gga | ttt | gct | aga | gcc | acg | caa | tgt | gtc | gtg | 864 |
| Tyr | Asp | Phe | Leu | Leu | Val | Gly | Phe | Ala | Arg | Ala | Thr | Gln | Cys | Val | Val | |
| | | 275 | | | | | 280 | | | | | 285 | | | | |

```
tat agc ggg gaa ttg cgt gac cat cgt aag cgt tga                    900
Tyr Ser Gly Glu Leu Arg Asp His Arg Lys Arg
    290                 295
```

<210> SEQ ID NO 32
<211> LENGTH: 299
<212> TYPE: PRT
<213> ORGANISM: Methylophilus methylotrophus

<400> SEQUENCE: 32

```
Val Glu Val Leu Asn Glu Gln Asp Cys Ala Leu Pro Asp Ser Gln Glu
1               5                   10                  15

Trp Gln Pro Ile Leu Ala Glu Gln Ala Ala Thr Val Ile Val Thr
            20                  25                  30

Arg Trp Arg Glu Asp Gln Ser Thr Thr Val Ala Asp Ala Leu Ala Gln
        35                  40                  45

Glu Val Pro Val Ala Leu Ile Tyr Asn Gly Ile Ser Tyr Val Val Met
    50                  55                  60

Leu Ala Thr Pro Ala Asp Leu Glu Asp Phe Ala Tyr Gly Phe Ser Phe
65                  70                  75                  80

Thr Glu Gly Ile Ile Thr Glu Arg Gly Gln Ile Tyr Gly Val Glu Ala
                85                  90                  95

Arg Ala Leu Thr Gln Ala Asp Gly Gln Leu Gln Gly Ile Glu Leu His
            100                 105                 110

Ile Asp Leu Ala Thr Glu Gln Phe Val Ala Leu Lys Ala Gln Arg Arg
        115                 120                 125

Asn Leu Thr Gly Arg Thr Gly Cys Gly Leu Cys Gly Ala Glu Ser Leu
    130                 135                 140

Gln Gln Val Phe Lys Gln Pro Met Pro Ala Ser Gly Pro Leu Val Ser
145                 150                 155                 160

Leu Ser Leu Thr Ala Leu Glu Ala Ala Leu Asp Gly Leu Lys Thr Arg
                165                 170                 175

Gln Pro Leu Gln Leu Leu Thr Gly Ala Thr His Ala Ser Ala Ile Ala
            180                 185                 190

Asp Ala His Gly Gln Val Val Cys Val Arg Glu Asp Val Gly Arg His
        195                 200                 205

Asn Ala Leu Asp Lys Leu Ile Gly Gly Leu Leu Arg Gln Gly His Asp
    210                 215                 220

Phe Ser Val Phe Trp Ala Thr His Trp Val Leu Thr Thr Ser Arg Ala
225                 230                 235                 240

Ser Tyr Glu Met Val Gln Lys Val Ala Val Cys Gly Gly Arg Ala Leu
                245                 250                 255

Val Ala Leu Ser Ala Pro Thr Ala Leu Ala Val Ser Leu Ala Asn Glu
            260                 265                 270

Tyr Asp Phe Leu Leu Val Gly Phe Ala Arg Ala Thr Gln Cys Val Val
        275                 280                 285

Tyr Ser Gly Glu Leu Arg Asp His Arg Lys Arg
    290                 295
```

<210> SEQ ID NO 33
<211> LENGTH: 1566
<212> TYPE: DNA
<213> ORGANISM: Methylophilus methylotrophus
<220> FEATURE:
<221> NAME/KEY: CDS
<222> LOCATION: (1)..(1566)
<223> OTHER INFORMATION:

<400> SEQUENCE: 33

```
atg gtt aag gtc tat gtg ccc att gat tcg gcg gcg ctt tct ttg ggt      48
Met Val Lys Val Tyr Val Pro Ile Asp Ser Ala Ala Leu Ser Leu Gly
1               5                   10                  15 gct gag cgc act gca aaa aga atc gtt cag gaa gcg caa acg cgt gga      96
Ala Glu Arg Thr Ala Lys Arg Ile Val Gln Glu Ala Gln Thr Arg Gly
            20                  25                  30 ata cag gtt gaa ttg gtt cgc aac ggt tcg cga ggc ttg ttc tgg ctc     144
Ile Gln Val Glu Leu Val Arg Asn Gly Ser Arg Gly Leu Phe Trp Leu
        35                  40                  45 gag ccg ctg gtt gaa gta gag act gca caa ggt cga gtg gct ttc ggt     192
Glu Pro Leu Val Glu Val Glu Thr Ala Gln Gly Arg Val Ala Phe Gly
    50                  55                  60 ccg gtg caa ccc aaa gat gtg gcc agc ttg ttc gtt gcc gct ttc act     240
Pro Val Gln Pro Lys Asp Val Ala Ser Leu Phe Val Ala Ala Phe Thr
65                  70                  75                  80 gac gcg ttg tct gat agt gcc agg gcg cat cct tta tat ttg ggt ctg     288
Asp Ala Leu Ser Asp Ser Ala Arg Ala His Pro Leu Tyr Leu Gly Leu
                85                  90                  95 aca gat gaa ata gcc tgg ctc aaa aag caa cag cgt ttg acc ttt gcg     336
Thr Asp Glu Ile Ala Trp Leu Lys Lys Gln Gln Arg Leu Thr Phe Ala
            100                 105                 110 cgt gtg ggt att atc gat ccg tta tcc ctg gaa gac tat ctt gcg cat     384
Arg Val Gly Ile Ile Asp Pro Leu Ser Leu Glu Asp Tyr Leu Ala His
        115                 120                 125 gat ggc tat caa ggc ctt aaa aat gcg ctt gcc atg acg ggt gcc gac     432
Asp Gly Tyr Gln Gly Leu Lys Asn Ala Leu Ala Met Thr Gly Ala Asp
    130                 135                 140 att gtt aaa gcg gtg aca gat tca ggc ttg cgc ggc cgt ggc ggc gca     480
Ile Val Lys Ala Val Thr Asp Ser Gly Leu Arg Gly Arg Gly Gly Ala
145                 150                 155                 160 gct ttc ccg aca ggg atc aaa tgg aat act gtg ctc aat gcg cca gca     528
Ala Phe Pro Thr Gly Ile Lys Trp Asn Thr Val Leu Asn Ala Pro Ala
                165                 170                 175 gag caa aag tat gtg gtc tgt aat gcc gac gag ggt gat tca ggg act     576
Glu Gln Lys Tyr Val Val Cys Asn Ala Asp Glu Gly Asp Ser Gly Thr
            180                 185                 190 tat tca gac cgc atg atc atg gaa gac gat cct ttt gtc ttg att gaa     624
Tyr Ser Asp Arg Met Ile Met Glu Asp Asp Pro Phe Val Leu Ile Glu
        195                 200                 205 ggc atg act att gcc ggt att gca gtg ggt gcc aca caa ggc tat atc     672
Gly Met Thr Ile Ala Gly Ile Ala Val Gly Ala Thr Gln Gly Tyr Ile
    210                 215                 220 tat ctg cgc agc gaa tat ccg cat gcg ctg aaa acg ctc aat gaa gcc     720
Tyr Leu Arg Ser Glu Tyr Pro His Ala Leu Lys Thr Leu Asn Glu Ala
225                 230                 235                 240 atc cgc aaa gcc aat ctg caa ggg tat tta ggc gaa aat att ctc ggt     768
Ile Arg Lys Ala Asn Leu Gln Gly Tyr Leu Gly Glu Asn Ile Leu Gly
                245                 250                 255 tct ggc cat agt ttc cat ctt gag gtg cgt agg gcg gct ggt gcc tat     816
Ser Gly His Ser Phe His Leu Glu Val Arg Arg Ala Ala Gly Ala Tyr
            260                 265                 270 gtc tgt ggc gaa gaa acc tcc ttg ctc gaa agc ctg gaa ggt aag cgt     864
Val Cys Gly Glu Glu Thr Ser Leu Leu Glu Ser Leu Glu Gly Lys Arg
        275                 280                 285 ggc ctg gtg cgt ttc aaa cca ccg ctc cct gcg ata gaa ggt ttg ttt     912
Gly Leu Val Arg Phe Lys Pro Pro Leu Pro Ala Ile Glu Gly Leu Phe
    290                 295                 300 ggt aag ccc acc att gtc aat aat gtg att tca ctg gct acg gtg ccg     960
```

-continued

```
Gly Lys Pro Thr Ile Val Asn Asn Val Ile Ser Leu Ala Thr Val Pro
305                 310                 315                 320 att att tta gat aag ggc gcg caa tat tat gcc gat tat ggc atg ggc    1008
Ile Ile Leu Asp Lys Gly Ala Gln Tyr Tyr Ala Asp Tyr Gly Met Gly
                325                 330                 335 cgt tcg cgc ggt acc ttg cct atc cag ttg gca ggc aat ctc aag caa    1056
Arg Ser Arg Gly Thr Leu Pro Ile Gln Leu Ala Gly Asn Leu Lys Gln
            340                 345                 350 act ggc ctg gtt gag ctg gct ttt ggt gct acc ttg cgc gag ttg ctg    1104
Thr Gly Leu Val Glu Leu Ala Phe Gly Ala Thr Leu Arg Glu Leu Leu
        355                 360                 365 tat gaa ttt ggc ggt ggt tcc gcc tcc ggt cgg cct atc cga gca gta    1152
Tyr Glu Phe Gly Gly Gly Ser Ala Ser Gly Arg Pro Ile Arg Ala Val
    370                 375                 380 caa gtc ggt ggg cca tta ggt gct tac ttg cct gag agc cag ttt gat    1200
Gln Val Gly Gly Pro Leu Gly Ala Tyr Leu Pro Glu Ser Gln Phe Asp
385                 390                 395                 400 acg ccg ctg gac tac gaa gag ttt acc aag ata tgg gcg gtg ctg ggc    1248
Thr Pro Leu Asp Tyr Glu Glu Phe Thr Lys Ile Trp Ala Val Leu Gly
                405                 410                 415 cat ggc ggt att gtc gcc ttt gat gat agc gtg gat atg gcc aaa atg    1296
His Gly Gly Ile Val Ala Phe Asp Asp Ser Val Asp Met Ala Lys Met
            420                 425                 430 gcg cgc tat gcc ttc gag ttt tgt gct gaa gaa agt tgt ggc aaa tgt    1344
Ala Arg Tyr Ala Phe Glu Phe Cys Ala Glu Glu Ser Cys Gly Lys Cys
        435                 440                 445 acg ccg tgc cgc ata ggt tct acg cgc ggc gtt gaa gtc atg gac aag    1392
Thr Pro Cys Arg Ile Gly Ser Thr Arg Gly Val Glu Val Met Asp Lys
    450                 455                 460 ata gtg ctt ggc aaa aac cat ccg caa aat gtg caa ttg ctg cgc gat    1440
Ile Val Leu Gly Lys Asn His Pro Gln Asn Val Gln Leu Leu Arg Asp
465                 470                 475                 480 ttg tcc gat acc atg ctc aat ggt tcg ttg tgt gca cta ggt ggc atg    1488
Leu Ser Asp Thr Met Leu Asn Gly Ser Leu Cys Ala Leu Gly Gly Met
                485                 490                 495 acg ccg tat ccg gtg ctg agt gcc ttg aat cat ttc cct gaa gat ttt    1536
Thr Pro Tyr Pro Val Leu Ser Ala Leu Asn His Phe Pro Glu Asp Phe
            500                 505                 510 ggt cta agc aat aaa gaa gct gct gcc tga                            1566
Gly Leu Ser Asn Lys Glu Ala Ala Ala
        515                 520

<210> SEQ ID NO 34
<211> LENGTH: 521
<212> TYPE: PRT
<213> ORGANISM: Methylophilus methylotrophus

<400> SEQUENCE: 34

Met Val Lys Val Tyr Val Pro Ile Asp Ser Ala Ala Leu Ser Leu Gly
1               5                   10                  15

Ala Glu Arg Thr Ala Lys Arg Ile Val Gln Glu Ala Gln Thr Arg Gly
            20                  25                  30

Ile Gln Val Glu Leu Val Arg Asn Gly Ser Arg Gly Leu Phe Trp Leu
        35                  40                  45

Glu Pro Leu Val Glu Val Glu Thr Ala Gln Gly Arg Val Ala Phe Gly
    50                  55                  60

Pro Val Gln Pro Lys Asp Val Ala Ser Leu Phe Val Ala Ala Phe Thr
65                  70                  75                  80

Asp Ala Leu Ser Asp Ser Ala Arg Ala His Pro Leu Tyr Leu Gly Leu
```

-continued

```
                 85                  90                  95
Thr Asp Glu Ile Ala Trp Leu Lys Lys Gln Gln Arg Leu Thr Phe Ala
            100                 105                 110
Arg Val Gly Ile Ile Asp Pro Leu Ser Leu Glu Asp Tyr Leu Ala His
            115                 120                 125
Asp Gly Tyr Gln Gly Leu Lys Asn Ala Leu Ala Met Thr Gly Ala Asp
            130                 135                 140
Ile Val Lys Ala Val Thr Asp Ser Gly Leu Arg Gly Arg Gly Gly Ala
145                 150                 155                 160
Ala Phe Pro Thr Gly Ile Lys Trp Asn Thr Val Leu Asn Ala Pro Ala
            165                 170                 175
Glu Gln Lys Tyr Val Val Cys Asn Ala Asp Glu Gly Asp Ser Gly Thr
            180                 185                 190
Tyr Ser Asp Arg Met Ile Met Glu Asp Asp Pro Phe Val Leu Ile Glu
            195                 200                 205
Gly Met Thr Ile Ala Gly Ile Ala Val Gly Ala Thr Gln Gly Tyr Ile
            210                 215                 220
Tyr Leu Arg Ser Glu Tyr Pro His Ala Leu Lys Thr Leu Asn Glu Ala
225                 230                 235                 240
Ile Arg Lys Ala Asn Leu Gln Gly Tyr Leu Gly Glu Asn Ile Leu Gly
            245                 250                 255
Ser Gly His Ser Phe His Leu Glu Val Arg Arg Ala Ala Gly Ala Tyr
            260                 265                 270
Val Cys Gly Glu Glu Thr Ser Leu Leu Glu Ser Leu Glu Gly Lys Arg
            275                 280                 285
Gly Leu Val Arg Phe Lys Pro Pro Leu Pro Ala Ile Glu Gly Leu Phe
            290                 295                 300
Gly Lys Pro Thr Ile Val Asn Asn Val Ile Ser Leu Ala Thr Val Pro
305                 310                 315                 320
Ile Ile Leu Asp Lys Gly Ala Gln Tyr Tyr Ala Asp Tyr Gly Met Gly
            325                 330                 335
Arg Ser Arg Gly Thr Leu Pro Ile Gln Leu Ala Gly Asn Leu Lys Gln
            340                 345                 350
Thr Gly Leu Val Glu Leu Ala Phe Gly Ala Thr Leu Arg Glu Leu Leu
            355                 360                 365
Tyr Glu Phe Gly Gly Gly Ser Ala Ser Gly Arg Pro Ile Arg Ala Val
            370                 375                 380
Gln Val Gly Gly Pro Leu Gly Ala Tyr Leu Pro Glu Ser Gln Phe Asp
385                 390                 395                 400
Thr Pro Leu Asp Tyr Glu Glu Phe Thr Lys Ile Trp Ala Val Leu Gly
            405                 410                 415
His Gly Gly Ile Val Ala Phe Asp Asp Ser Val Asp Met Ala Lys Met
            420                 425                 430
Ala Arg Tyr Ala Phe Glu Phe Cys Ala Glu Glu Ser Cys Gly Lys Cys
            435                 440                 445
Thr Pro Cys Arg Ile Gly Ser Thr Arg Gly Val Glu Val Met Asp Lys
            450                 455                 460
Ile Val Leu Gly Lys Asn His Pro Gln Asn Val Gln Leu Leu Arg Asp
465                 470                 475                 480
Leu Ser Asp Thr Met Leu Asn Gly Ser Leu Cys Ala Leu Gly Gly Met
            485                 490                 495
Thr Pro Tyr Pro Val Leu Ser Ala Leu Asn His Phe Pro Glu Asp Phe
            500                 505                 510
```

-continued

```
Gly Leu Ser Asn Lys Glu Ala Ala Ala
        515                 520

<210> SEQ ID NO 35
<211> LENGTH: 2892
<212> TYPE: DNA
<213> ORGANISM: Methylophilus methylotrophus
<220> FEATURE:
<221> NAME/KEY: CDS
<222> LOCATION: (1)..(2892)
<223> OTHER INFORMATION:

<400> SEQUENCE: 35 atg gac gac atc aaa tac tca tct tcc cag cca cag atg ccg aag tat        48
Met Asp Asp Ile Lys Tyr Ser Ser Ser Gln Pro Gln Met Pro Lys Tyr
1               5                   10                  15 gat cct gat aag gat tac ggc aca ccg aag tct gac agt gcc acc atg        96
Asp Pro Asp Lys Asp Tyr Gly Thr Pro Lys Ser Asp Ser Ala Thr Met
            20                  25                  30 gtg acc ctg aac att gac ggc gtg gat gtg aca gtg cca gac ggg act       144
Val Thr Leu Asn Ile Asp Gly Val Asp Val Thr Val Pro Asp Gly Thr
        35                  40                  45 tcc atc atg cac gca gcc caa ctg gga ggt gtc acc gtt ccc aag ttg       192
Ser Ile Met His Ala Ala Gln Leu Gly Gly Val Thr Val Pro Lys Leu
    50                  55                  60 tgt gcc act gac tct tta gag cct ttc ggt tcc tgc cgt tta tgc ctg       240
Cys Ala Thr Asp Ser Leu Glu Pro Phe Gly Ser Cys Arg Leu Cys Leu
65                  70                  75                  80 gtc gag atc gaa ggc cgg cgc ggc tac ccg gct tct tgt acc acg cct       288
Val Glu Ile Glu Gly Arg Arg Gly Tyr Pro Ala Ser Cys Thr Thr Pro
                85                  90                  95 gtt gcc ccc ggg ctt aaa gtc aaa acc cag acg ccc aaa ctg gca gat       336
Val Ala Pro Gly Leu Lys Val Lys Thr Gln Thr Pro Lys Leu Ala Asp
            100                 105                 110 gtt cgt cgc ggc gtc atg gaa ttg tat atc tct gac cat ccg ctg gac       384
Val Arg Arg Gly Val Met Glu Leu Tyr Ile Ser Asp His Pro Leu Asp
        115                 120                 125 tgt ctg acc tgc gct gcc aat ggc gac tgc gaa ttg cag gac atg gct       432
Cys Leu Thr Cys Ala Ala Asn Gly Asp Cys Glu Leu Gln Asp Met Ala
    130                 135                 140 ggc gct gtc ggt ttg cgc gaa gtg cgt tat ggc tat gaa ggt gaa aat       480
Gly Ala Val Gly Leu Arg Glu Val Arg Tyr Gly Tyr Glu Gly Glu Asn
145                 150                 155                 160 cac att ggc cag gcc aag gat gag tcc aat cct tat ttc acg ttt gac       528
His Ile Gly Gln Ala Lys Asp Glu Ser Asn Pro Tyr Phe Thr Phe Asp
                165                 170                 175 ccc tct aaa tgt atc gtc tgc tca cgc tgt gtg cgt gcc tgt gaa gaa       576
Pro Ser Lys Cys Ile Val Cys Ser Arg Cys Val Arg Ala Cys Glu Glu
            180                 185                 190 act cag ggg act ttt gcg ctc acg atc cag ggg cgc ggt ttt gaa agc       624
Thr Gln Gly Thr Phe Ala Leu Thr Ile Gln Gly Arg Gly Phe Glu Ser
        195                 200                 205 aag gtc tct gcc ggt aat aag gat ttc ctc gac tcg gaa tgt gtc tct       672
Lys Val Ser Ala Gly Asn Lys Asp Phe Leu Asp Ser Glu Cys Val Ser
    210                 215                 220 tgc ggt gcc tgc gta cag gca tgc cct acg gcc acc ctg atg gaa aaa       720
Cys Gly Ala Cys Val Gln Ala Cys Pro Thr Ala Thr Leu Met Glu Lys
225                 230                 235                 240 acc gtg att gag gcc ggt acg cca gaa cac aaa atc acc acc acc tgt       768
Thr Val Ile Glu Ala Gly Thr Pro Glu His Lys Ile Thr Thr Thr Cys
                245                 250                 255
```

```
gct tat tgc ggc gtt ggt tgc agc ttt gat gcc gaa atg aaa ggt gag      816
Ala Tyr Cys Gly Val Gly Cys Ser Phe Asp Ala Glu Met Lys Gly Glu
        260                 265                 270 cag gtc gtg cgc atg acg cct agc aaa gag ggt ggt gcc aac cat ggt      864
Gln Val Val Arg Met Thr Pro Ser Lys Glu Gly Gly Ala Asn His Gly
            275                 280                 285 cat agc tgt gta aaa ggc cgt ttt gct tgg ggc tat gcg acc cac gct      912
His Ser Cys Val Lys Gly Arg Phe Ala Trp Gly Tyr Ala Thr His Ala
290                 295                 300 gac cgc att acc acg cct atg ata cgc aaa agc att cat gac ccc tgg      960
Asp Arg Ile Thr Thr Pro Met Ile Arg Lys Ser Ile His Asp Pro Trp
305                 310                 315                 320 caa aaa gtc ggt tgg gat gag gca att aat tac gct gcc agc gaa atc     1008
Gln Lys Val Gly Trp Asp Glu Ala Ile Asn Tyr Ala Ala Ser Glu Ile
                325                 330                 335 aag cgc att cag gct caa tat ggc aag gag gcc gtc ggt ggg atc act     1056
Lys Arg Ile Gln Ala Gln Tyr Gly Lys Glu Ala Val Gly Gly Ile Thr
            340                 345                 350 tcc agc cgt tgc acc aat gaa gaa gtg tat gtg aca caa aag ctg atc     1104
Ser Ser Arg Cys Thr Asn Glu Glu Val Tyr Val Thr Gln Lys Leu Ile
        355                 360                 365 cgt gcc gtg ttt ggg gtg aat aat gtg gat acc tgt gcg cgt gtt tgc     1152
Arg Ala Val Phe Gly Val Asn Asn Val Asp Thr Cys Ala Arg Val Cys
370                 375                 380 cat agc ccg act ggc tat ggc ctc aag cag acc ctg ggc gaa tca gcc     1200
His Ser Pro Thr Gly Tyr Gly Leu Lys Gln Thr Leu Gly Glu Ser Ala
385                 390                 395                 400 ggg aca caa acg ttt gat tct gtc atg aag tct gac gtg att ttt gtc     1248
Gly Thr Gln Thr Phe Asp Ser Val Met Lys Ser Asp Val Ile Phe Val
                405                 410                 415 atg ggc gcc aac ccc act gat ggc cac ccg gta ttt gct tct atc atg     1296
Met Gly Ala Asn Pro Thr Asp Gly His Pro Val Phe Ala Ser Ile Met
            420                 425                 430 aag cgc cgc ttg cgt gaa ggg gcc aag ctg att gtg gtt gat cca cgt     1344
Lys Arg Arg Leu Arg Glu Gly Ala Lys Leu Ile Val Val Asp Pro Arg
        435                 440                 445 gaa att gac ctg gtg gat aat tcc ccg cat gtg cgt gct gat tat cac     1392
Glu Ile Asp Leu Val Asp Asn Ser Pro His Val Arg Ala Asp Tyr His
450                 455                 460 ctc aaa ttg cgt cct ggc acc aac gtg gcc atg att tct gcg att tca     1440
Leu Lys Leu Arg Pro Gly Thr Asn Val Ala Met Ile Ser Ala Ile Ser
465                 470                 475                 480 cat gtg att gtg act gaa ggc ctg gta cag gaa gag ttt gtg aaa gcc     1488
His Val Ile Val Thr Glu Gly Leu Val Gln Glu Glu Phe Val Lys Ala
                485                 490                 495 cgt tgc gag tgg gac tct tac gtt gcc tgg cgt gac ttt gct gcc aag     1536
Arg Cys Glu Trp Asp Ser Tyr Val Ala Trp Arg Asp Phe Ala Ala Lys
            500                 505                 510 ccg gaa aac tcc ccg gaa gcg ctg gaa aaa gaa tta ggc gtg cca gca     1584
Pro Glu Asn Ser Pro Glu Ala Leu Glu Lys Glu Leu Gly Val Pro Ala
        515                 520                 525 aat gat gta cgc gaa gcg gca cgt tta tat gca aca ggc ggt aat gct     1632
Asn Asp Val Arg Glu Ala Ala Arg Leu Tyr Ala Thr Gly Gly Asn Ala
530                 535                 540 gcc att tat tat ggc ctg ggt gtc acc gaa cat agc cag ggc tcc acc     1680
Ala Ile Tyr Tyr Gly Leu Gly Val Thr Glu His Ser Gln Gly Ser Thr
545                 550                 555                 560 act gtg atg ggg att gcc aac ttg gcg atg gca acc gcg aat att ggc     1728
Thr Val Met Gly Ile Ala Asn Leu Ala Met Ala Thr Ala Asn Ile Gly
```

-continued

|  |  |  |  |  |  |  |
|---|---|---|---|---|---|---|
|  | 565 |  | 570 |  | 575 |  |

```
cgc gaa ggc gta ggg gtg aat cca ttg cgt ggt caa aac aat gta caa    1776
Arg Glu Gly Val Gly Val Asn Pro Leu Arg Gly Gln Asn Asn Val Gln
        580                 585                 590 ggg tct tgt gac atg ggc tcc atg ccg cat gag ttt cct ggc tac cgt    1824
Gly Ser Cys Asp Met Gly Ser Met Pro His Glu Phe Pro Gly Tyr Arg
    595                 600                 605 cat gtt tct gac gat gca aca cgc gcc cag ttt gaa caa gcg tgg ggc    1872
His Val Ser Asp Asp Ala Thr Arg Ala Gln Phe Glu Gln Ala Trp Gly
610                 615                 620 gtg aca ctg agt gct gac cct ggt ttg cgt atc ccc aat atg ctg gac    1920
Val Thr Leu Ser Ala Asp Pro Gly Leu Arg Ile Pro Asn Met Leu Asp
625                 630                 635                 640 ctg gct gtg gaa ggt agc ttt aaa gcg gtt tat tgt gta ggc gaa gat    1968
Leu Ala Val Glu Gly Ser Phe Lys Ala Val Tyr Cys Val Gly Glu Asp
                645                 650                 655 att gca caa tct gat cct gat acc cag cac gtg aca cat gcg ctg gaa    2016
Ile Ala Gln Ser Asp Pro Asp Thr Gln His Val Thr His Ala Leu Glu
            660                 665                 670 aac atg gag tgc gtc att gtg cag gat ttg ttc ctg aac gaa act gcc    2064
Asn Met Glu Cys Val Ile Val Gln Asp Leu Phe Leu Asn Glu Thr Ala
        675                 680                 685 aag ttc gcc cac gtt ttt ttc cca ggc gcc tct ttc ctt gag aaa aac    2112
Lys Phe Ala His Val Phe Phe Pro Gly Ala Ser Phe Leu Glu Lys Asn
    690                 695                 700 ggc aca ttc acc aat gcc gag cgc cgt att tca cct gtg cgc aaa gtg    2160
Gly Thr Phe Thr Asn Ala Glu Arg Arg Ile Ser Pro Val Arg Lys Val
705                 710                 715                 720 atg acg cca aaa aat ggc atg gaa gac tgg gag att act gct aaa ttc    2208
Met Thr Pro Lys Asn Gly Met Glu Asp Trp Glu Ile Thr Ala Lys Phe
                725                 730                 735 tca gag gcc ttg ggt tac ccc atg cat tac gca cat gcc agt gaa atc    2256
Ser Glu Ala Leu Gly Tyr Pro Met His Tyr Ala His Ala Ser Glu Ile
            740                 745                 750 atg gat gag att gcc gct ctg acg ccg acc ttt acc ggt gtc agc ttc    2304
Met Asp Glu Ile Ala Ala Leu Thr Pro Thr Phe Thr Gly Val Ser Phe
        755                 760                 765 aaa aaa ctg gat gaa ctg ggc agt atc cag tgg cca tgt aat gac gaa    2352
Lys Lys Leu Asp Glu Leu Gly Ser Ile Gln Trp Pro Cys Asn Asp Glu
    770                 775                 780 gcc cct acg ggg acg cca acc atg cat gtg gat gag ttt gta cgt ggt    2400
Ala Pro Thr Gly Thr Pro Thr Met His Val Asp Glu Phe Val Arg Gly
785                 790                 795                 800 aaa ggc aag ttc ttt att acc cag tat gtg ccc acc act gag cgc gtc    2448
Lys Gly Lys Phe Phe Ile Thr Gln Tyr Val Pro Thr Thr Glu Arg Val
                805                 810                 815 aac cag aaa tac ccc ctg atc ctg acc acc ggc cgt atc ctg tcg caa    2496
Asn Gln Lys Tyr Pro Leu Ile Leu Thr Thr Gly Arg Ile Leu Ser Gln
            820                 825                 830 tat aac gtg ggt gcg caa acc cgc cgt acg cat aac gtg gca tgg cac    2544
Tyr Asn Val Gly Ala Gln Thr Arg Arg Thr His Asn Val Ala Trp His
        835                 840                 845 cat gag gat ttg att gaa att cat ccg cat gac gcc gaa gac cgg ggc    2592
His Glu Asp Leu Ile Glu Ile His Pro His Asp Ala Glu Asp Arg Gly
    850                 855                 860 att gct gaa ggc gat tgg gtg ggc att acc agc cgt gcc ggg cag acg    2640
Ile Ala Glu Gly Asp Trp Val Gly Ile Thr Ser Arg Ala Gly Gln Thr
865                 870                 875                 880 gta tta cgg gcc aag att acc gat cgc gtg cag cca ggc gtg gtg tat    2688
```

-continued

```
                Val Leu Arg Ala Lys Ile Thr Asp Arg Val Gln Pro Gly Val Val Tyr
                                885                 890                 895 acc act ttc cac cat cct gag tct ggt gcc aat gta att act aca gac      2736
Thr Thr Phe His His Pro Glu Ser Gly Ala Asn Val Ile Thr Thr Asp
                900                 905                 910 aac tcc gac tgg gcg acc aat tgc cct gaa tac aaa gtg act gcc gtg      2784
Asn Ser Asp Trp Ala Thr Asn Cys Pro Glu Tyr Lys Val Thr Ala Val
            915                 920                 925 cag gtg tcc aaa gtc aac cag ctg tct gat tgg cag aag cag tac cgt      2832
Gln Val Ser Lys Val Asn Gln Leu Ser Asp Trp Gln Lys Gln Tyr Arg
        930                 935                 940 tcg ttt agt gat aca caa att gaa ctg tca ggg atg gat ccg caa acg      2880
Ser Phe Ser Asp Thr Gln Ile Glu Leu Ser Gly Met Asp Pro Gln Thr
945                 950                 955                 960 gtt gtt tct tga                                                       2892
Val Val Ser <210> SEQ ID NO 36
<211> LENGTH: 963
<212> TYPE: PRT
<213> ORGANISM: Methylophilus methylotrophus

<400> SEQUENCE: 36

Met Asp Asp Ile Lys Tyr Ser Ser Gln Pro Gln Met Pro Lys Tyr
1               5                   10                  15

Asp Pro Asp Lys Asp Tyr Gly Thr Pro Lys Ser Asp Ser Ala Thr Met
                20                  25                  30

Val Thr Leu Asn Ile Asp Gly Val Asp Val Thr Val Pro Asp Gly Thr
            35                  40                  45

Ser Ile Met His Ala Ala Gln Leu Gly Gly Val Thr Val Pro Lys Leu
        50                  55                  60

Cys Ala Thr Asp Ser Leu Glu Pro Phe Gly Ser Cys Arg Leu Cys Leu
65                  70                  75                  80

Val Glu Ile Glu Gly Arg Arg Gly Tyr Pro Ala Ser Cys Thr Thr Pro
                85                  90                  95

Val Ala Pro Gly Leu Lys Val Lys Thr Gln Thr Pro Lys Leu Ala Asp
                100                 105                 110

Val Arg Arg Gly Val Met Glu Leu Tyr Ile Ser Asp His Pro Leu Asp
            115                 120                 125

Cys Leu Thr Cys Ala Ala Asn Gly Asp Cys Glu Leu Gln Asp Met Ala
        130                 135                 140

Gly Ala Val Gly Leu Arg Glu Val Arg Tyr Gly Tyr Glu Gly Glu Asn
145                 150                 155                 160

His Ile Gly Gln Ala Lys Asp Glu Ser Asn Pro Tyr Phe Thr Phe Asp
                165                 170                 175

Pro Ser Lys Cys Ile Val Cys Ser Arg Cys Val Arg Ala Cys Glu Glu
                180                 185                 190

Thr Gln Gly Thr Phe Ala Leu Thr Ile Gln Gly Arg Gly Phe Glu Ser
            195                 200                 205

Lys Val Ser Ala Gly Asn Lys Asp Phe Leu Asp Ser Glu Cys Val Ser
        210                 215                 220

Cys Gly Ala Cys Val Gln Ala Cys Pro Thr Ala Thr Leu Met Glu Lys
225                 230                 235                 240

Thr Val Ile Glu Ala Gly Thr Pro Glu His Lys Ile Thr Thr Cys
                245                 250                 255

Ala Tyr Cys Gly Val Gly Cys Ser Phe Asp Ala Glu Met Lys Gly Glu
```

-continued

```
                260                 265                 270
Gln Val Val Arg Met Thr Pro Ser Lys Glu Gly Gly Ala Asn His Gly
            275                 280                 285
His Ser Cys Val Lys Gly Arg Phe Ala Trp Gly Tyr Ala Thr His Ala
        290                 295                 300
Asp Arg Ile Thr Thr Pro Met Ile Arg Lys Ser Ile His Asp Pro Trp
305                 310                 315                 320
Gln Lys Val Gly Trp Asp Glu Ala Ile Asn Tyr Ala Ala Ser Glu Ile
                325                 330                 335
Lys Arg Ile Gln Ala Gln Tyr Gly Lys Glu Ala Val Gly Gly Ile Thr
            340                 345                 350
Ser Ser Arg Cys Thr Asn Glu Glu Val Tyr Val Thr Gln Lys Leu Ile
        355                 360                 365
Arg Ala Val Phe Gly Val Asn Asn Val Asp Thr Cys Ala Arg Val Cys
        370                 375                 380
His Ser Pro Thr Gly Tyr Gly Leu Lys Gln Thr Leu Gly Glu Ser Ala
385                 390                 395                 400
Gly Thr Gln Thr Phe Asp Ser Val Met Lys Ser Asp Val Ile Phe Val
                405                 410                 415
Met Gly Ala Asn Pro Thr Asp Gly His Pro Val Phe Ala Ser Ile Met
            420                 425                 430
Lys Arg Arg Leu Arg Glu Gly Ala Lys Leu Ile Val Val Asp Pro Arg
        435                 440                 445
Glu Ile Asp Leu Val Asp Asn Ser Pro His Val Arg Ala Asp Tyr His
        450                 455                 460
Leu Lys Leu Arg Pro Gly Thr Asn Val Ala Met Ile Ser Ala Ile Ser
465                 470                 475                 480
His Val Ile Val Thr Glu Gly Leu Val Gln Glu Phe Val Lys Ala
                485                 490                 495
Arg Cys Glu Trp Asp Ser Tyr Val Ala Trp Arg Asp Phe Ala Ala Lys
            500                 505                 510
Pro Glu Asn Ser Pro Glu Ala Leu Glu Lys Glu Leu Gly Val Pro Ala
        515                 520                 525
Asn Asp Val Arg Glu Ala Ala Arg Leu Tyr Ala Thr Gly Gly Asn Ala
530                 535                 540
Ala Ile Tyr Tyr Gly Leu Gly Val Thr Glu His Ser Gln Gly Ser Thr
545                 550                 555                 560
Thr Val Met Gly Ile Ala Asn Leu Ala Met Ala Thr Ala Asn Ile Gly
                565                 570                 575
Arg Glu Gly Val Gly Val Asn Pro Leu Arg Gly Gln Asn Asn Val Gln
            580                 585                 590
Gly Ser Cys Asp Met Gly Ser Met Pro His Glu Phe Pro Gly Tyr Arg
        595                 600                 605
His Val Ser Asp Asp Ala Thr Arg Ala Gln Phe Glu Gln Ala Trp Gly
        610                 615                 620
Val Thr Leu Ser Ala Asp Pro Gly Leu Arg Ile Pro Asn Met Leu Asp
625                 630                 635                 640
Leu Ala Val Glu Gly Ser Phe Lys Ala Val Tyr Cys Val Gly Glu Asp
                645                 650                 655
Ile Ala Gln Ser Asp Pro Asp Thr Gln His Val Thr His Ala Leu Glu
            660                 665                 670
Asn Met Glu Cys Val Ile Val Gln Asp Leu Phe Leu Asn Glu Thr Ala
        675                 680                 685
```

```
Lys Phe Ala His Val Phe Phe Pro Gly Ala Ser Phe Leu Glu Lys Asn
    690                 695                 700
Gly Thr Phe Thr Asn Ala Glu Arg Arg Ile Ser Pro Val Arg Lys Val
705                 710                 715                 720
Met Thr Pro Lys Asn Gly Met Glu Asp Trp Glu Ile Thr Ala Lys Phe
                725                 730                 735
Ser Glu Ala Leu Gly Tyr Pro Met His Tyr Ala His Ala Ser Glu Ile
                740                 745                 750
Met Asp Glu Ile Ala Ala Leu Thr Pro Thr Phe Thr Gly Val Ser Phe
            755                 760                 765
Lys Lys Leu Asp Glu Leu Gly Ser Ile Gln Trp Pro Cys Asn Asp Glu
    770                 775                 780
Ala Pro Thr Gly Thr Pro Thr Met His Val Asp Glu Phe Val Arg Gly
785                 790                 795                 800
Lys Gly Lys Phe Phe Ile Thr Gln Tyr Val Pro Thr Thr Glu Arg Val
                805                 810                 815
Asn Gln Lys Tyr Pro Leu Ile Leu Thr Thr Gly Arg Ile Leu Ser Gln
                820                 825                 830
Tyr Asn Val Gly Ala Gln Thr Arg Arg Thr His Asn Val Ala Trp His
            835                 840                 845
His Glu Asp Leu Ile Glu Ile His Pro His Asp Ala Glu Asp Arg Gly
    850                 855                 860
Ile Ala Glu Gly Asp Trp Val Gly Ile Thr Ser Arg Ala Gly Gln Thr
865                 870                 875                 880
Val Leu Arg Ala Lys Ile Thr Asp Arg Val Gln Pro Gly Val Val Tyr
                885                 890                 895
Thr Thr Phe His His Pro Glu Ser Gly Ala Asn Val Ile Thr Thr Asp
                900                 905                 910
Asn Ser Asp Trp Ala Thr Asn Cys Pro Glu Tyr Lys Val Thr Ala Val
            915                 920                 925
Gln Val Ser Lys Val Asn Gln Leu Ser Asp Trp Gln Lys Gln Tyr Arg
    930                 935                 940
Ser Phe Ser Asp Thr Gln Ile Glu Leu Ser Gly Met Asp Pro Gln Thr
945                 950                 955                 960
Val Val Ser
```

<210> SEQ ID NO 37
<211> LENGTH: 708
<212> TYPE: DNA
<213> ORGANISM: Methylophilus methylotrophus
<220> FEATURE:
<221> NAME/KEY: CDS
<222> LOCATION: (1)..(708)
<223> OTHER INFORMATION:

<400> SEQUENCE: 37

```
atg gca gtg att gat cga gta ttg att ggt gaa ggt ttg gtc atc gaa    48
Met Ala Val Ile Asp Arg Val Leu Ile Gly Glu Gly Leu Val Ile Glu
1               5                   10                  15 gaa cgt cca gaa ggt ggc ctg gat ttg aaa aat gtg gct cac att gac    96
Glu Arg Pro Glu Gly Gly Leu Asp Leu Lys Asn Val Ala His Ile Asp
            20                  25                  30 tta att atg ggc cca cgc ggt agc gct gca gaa gac gca ttt tgt cgt   144
Leu Ile Met Gly Pro Arg Gly Ser Ala Ala Glu Asp Ala Phe Cys Arg
        35                  40                  45 acg ctc acc gac caa aaa caa ggg gta aac ggt tta ttg gcg att gca   192
```

```
gcg cca aac atg atg gta aaa cca aat act gtg atg ttt aac aaa gtg      240
Ala Pro Asn Met Met Val Lys Pro Asn Thr Val Met Phe Asn Lys Val
 65              70                  75                  80 acg atc aaa gat ggt cgc cag gca aca caa atg ttt ggt ccg gca caa      288
Thr Ile Lys Asp Gly Arg Gln Ala Thr Gln Met Phe Gly Pro Ala Gln
                 85                  90                  95 cgt ggc gta gcc atg gct gtg atg gat tgc gtc gct gat ggc acc atc      336
Arg Gly Val Ala Met Ala Val Met Asp Cys Val Ala Asp Gly Thr Ile
            100                 105                 110 cca ttg gaa gaa gca gat gac gta ttt atc tgt gtg ggc gta ttt atc      384
Pro Leu Glu Glu Ala Asp Asp Val Phe Ile Cys Val Gly Val Phe Ile
        115                 120                 125 gac agc aag gct gat atg gat gac cgt att cag gac tgg aac tac cgt      432
Asp Ser Lys Ala Asp Met Asp Asp Arg Ile Gln Asp Trp Asn Tyr Arg
    130                 135                 140 gca acc aaa ata gcg att aaa gcc gca gtt gcc cgt gag cct aaa gct      480
Ala Thr Lys Ile Ala Ile Lys Ala Ala Val Ala Arg Glu Pro Lys Ala
145                 150                 155                 160 gct gat gtt gtg aaa cag tac aaa gaa gca ttg cac cca ttt gca gca      528
Ala Asp Val Val Lys Gln Tyr Lys Glu Ala Leu His Pro Phe Ala Ala
                165                 170                 175 caa aca cca gaa gca caa aac cgc cgt gcg gat gac cag gca gct gct      576
Gln Thr Pro Glu Ala Gln Asn Arg Arg Ala Asp Asp Gln Ala Ala Ala
            180                 185                 190 ctg gcg att tcg caa atg aaa gag cgt agc cat tat gta cgc aag agt      624
Leu Ala Ile Ser Gln Met Lys Glu Arg Ser His Tyr Val Arg Lys Ser
        195                 200                 205 gca gaa gcc aag gcc aga gaa gaa aaa cag ctt gaa ttg gca gtc gca      672
Ala Glu Ala Lys Ala Arg Glu Glu Lys Gln Leu Glu Leu Ala Val Ala
    210                 215                 220 caa atg aaa gaa cgt gtc gat acc act aaa gct taa                      708
Gln Met Lys Glu Arg Val Asp Thr Thr Lys Ala
225                 230                 235

<210> SEQ ID NO 38
<211> LENGTH: 235
<212> TYPE: PRT
<213> ORGANISM: Methylophilus methylotrophus

<400> SEQUENCE: 38

Met Ala Val Ile Asp Arg Val Leu Ile Gly Glu Gly Leu Val Ile Glu
1               5                   10                  15

Glu Arg Pro Glu Gly Gly Leu Asp Leu Lys Asn Val Ala His Ile Asp
            20                  25                  30

Leu Ile Met Gly Pro Arg Gly Ser Ala Ala Glu Asp Ala Phe Cys Arg
        35                  40                  45

Thr Leu Thr Asp Gln Lys Gln Gly Val Asn Gly Leu Leu Ala Ile Ala
    50                  55                  60

Ala Pro Asn Met Met Val Lys Pro Asn Thr Val Met Phe Asn Lys Val
65              70                  75                  80

Thr Ile Lys Asp Gly Arg Gln Ala Thr Gln Met Phe Gly Pro Ala Gln
                85                  90                  95

Arg Gly Val Ala Met Ala Val Met Asp Cys Val Ala Asp Gly Thr Ile
            100                 105                 110

Pro Leu Glu Glu Ala Asp Asp Val Phe Ile Cys Val Gly Val Phe Ile
        115                 120                 125
```

```
Asp Ser Lys Ala Asp Met Asp Asp Arg Ile Gln Asp Trp Asn Tyr Arg
    130                 135                 140

Ala Thr Lys Ile Ala Ile Lys Ala Ala Val Ala Arg Glu Pro Lys Ala
145                 150                 155                 160

Ala Asp Val Val Lys Gln Tyr Lys Glu Ala Leu His Pro Phe Ala Ala
                165                 170                 175

Gln Thr Pro Glu Ala Gln Asn Arg Arg Ala Asp Asp Gln Ala Ala Ala
            180                 185                 190

Leu Ala Ile Ser Gln Met Lys Glu Arg Ser His Tyr Val Arg Lys Ser
        195                 200                 205

Ala Glu Ala Lys Ala Arg Glu Glu Lys Gln Leu Glu Leu Ala Val Ala
    210                 215                 220

Gln Met Lys Glu Arg Val Asp Thr Thr Lys Ala
225                 230                 235

<210> SEQ ID NO 39
<211> LENGTH: 1194
<212> TYPE: DNA
<213> ORGANISM: Methylophilus methylotrophus
<220> FEATURE:
<221> NAME/KEY: CDS
<222> LOCATION: (1)..(1194)
<223> OTHER INFORMATION:

<400> SEQUENCE: 39 atg cgc gca ctt acc tat cat ggt agt aaa gat gtc cgg gtc gag act      48
Met Arg Ala Leu Thr Tyr His Gly Ser Lys Asp Val Arg Val Glu Thr
1               5                   10                  15 gtg cct gac cca gtg atc caa tat gcc gac gat gtg att ctc agg gta      96
Val Pro Asp Pro Val Ile Gln Tyr Ala Asp Asp Val Ile Leu Arg Val
            20                  25                  30 acg gca acg gcc atc tgt ggc tca gac ctg cat ctg tat cgt ggc aaa     144
Thr Ala Thr Ala Ile Cys Gly Ser Asp Leu His Leu Tyr Arg Gly Lys
        35                  40                  45 att cca atg gtc aag gat ggc gat att ctt ggc cat gaa ttt atg ggt     192
Ile Pro Met Val Lys Asp Gly Asp Ile Leu Gly His Glu Phe Met Gly
    50                  55                  60 gtt atc gaa gaa gtc ggt tct gct gtg gat caa gtc caa aaa gga gac     240
Val Ile Glu Glu Val Gly Ser Ala Val Asp Gln Val Gln Lys Gly Asp
65                  70                  75                  80 cgt gtc att atc ccg ttt gtg att gcc tgt gga cac tgc ttt ttt tgc     288
Arg Val Ile Ile Pro Phe Val Ile Ala Cys Gly His Cys Phe Phe Cys
                85                  90                  95 gaa aaa agc ctg tac gcc gcc tgc gag aac acc aat cct ggc cgt ggt     336
Glu Lys Ser Leu Tyr Ala Ala Cys Glu Asn Thr Asn Pro Gly Arg Gly
            100                 105                 110 gcc agc ctc aac aaa aaa tcc gtc aaa ccg cca gcg gcc ttg ttt ggt     384
Ala Ser Leu Asn Lys Lys Ser Val Lys Pro Pro Ala Ala Leu Phe Gly
        115                 120                 125 tac agc cat tta tat ggc ggc gtg cca ggg gga cag gct gag ctg gta     432
Tyr Ser His Leu Tyr Gly Gly Val Pro Gly Gly Gln Ala Glu Leu Val
    130                 135                 140 cgc gtg cca cgt ggc aat gcc ggg cca ttt aaa gtg cca gga tcg cta     480
Arg Val Pro Arg Gly Asn Ala Gly Pro Phe Lys Val Pro Gly Ser Leu
145                 150                 155                 160 gcg gat gaa cag gta ttg ttc ctg aca gat atc ttg cct acc ggt tac     528
Ala Asp Glu Gln Val Leu Phe Leu Thr Asp Ile Leu Pro Thr Gly Tyr
                165                 170                 175 cag gcc gtt tta aat gct gac gtc gtg cca ggc tcc acc att gcg att     576
Gln Ala Val Leu Asn Ala Asp Val Val Pro Gly Ser Thr Ile Ala Ile
```

```
                180                185                190
ttt ggc gcc ggg ccg gta ggc ctg atg gca gcc gcc tgt gcc cgc atg      624
Phe Gly Ala Gly Pro Val Gly Leu Met Ala Ala Ala Cys Ala Arg Met
            195                200                205 ctg ggt gcc gaa acc att ttc atg ata gat cac cat caa tac cgc ctg      672
Leu Gly Ala Glu Thr Ile Phe Met Ile Asp His His Gln Tyr Arg Leu
    210                215                220 gat tat gcc tca cag gta tac gac act atc ggc att aat ttt gac gag      720
Asp Tyr Ala Ser Gln Val Tyr Asp Thr Ile Gly Ile Asn Phe Asp Glu
225                230                235                240 gtg gaa gac ccg gcg gag ttc att ctc cag cac acc cag cat cgc ggc      768
Val Glu Asp Pro Ala Glu Phe Ile Leu Gln His Thr Gln His Arg Gly
                245                250                255 gtg gat gcc agc att gat gct gtc ggt ttt gaa gcc aag ggg agc atg      816
Val Asp Ala Ser Ile Asp Ala Val Gly Phe Glu Ala Lys Gly Ser Met
            260                265                270 gtt gaa acg gcg ctc acc acc ttg aaa ctc gaa acc agc agt ggc gag      864
Val Glu Thr Ala Leu Thr Thr Leu Lys Leu Glu Thr Ser Ser Gly Glu
    275                280                285 acc ctg cgc cag tgt att gcc gcc acc cgt cgc ggc gga att atc agc      912
Thr Leu Arg Gln Cys Ile Ala Ala Thr Arg Arg Gly Gly Ile Ile Ser
290                295                300 att cca ggc gtt tat gcc ggt ttt atc cat gct ttc ctg cta ggt gat      960
Ile Pro Gly Val Tyr Ala Gly Phe Ile His Ala Phe Leu Leu Gly Asp
305                310                315                320 gcc ttt gac aag ggc ctc act ttc aaa atg ggg caa act cat gtg cat     1008
Ala Phe Asp Lys Gly Leu Thr Phe Lys Met Gly Gln Thr His Val His
                325                330                335 ggt tat ctc tca gaa tta ctg cgc tat att gag gag gat aaa ttg cgt     1056
Gly Tyr Leu Ser Glu Leu Leu Arg Tyr Ile Glu Glu Asp Lys Leu Arg
            340                345                350 cct gcg gat att atc act cac cgc atg tca ctc gaa gat gct gca aaa     1104
Pro Ala Asp Ile Ile Thr His Arg Met Ser Leu Glu Asp Ala Ala Lys
    355                360                365 ggc tat gaa att ttc aat aat aaa gag gaa gat tgc cgc aaa gtg gtc     1152
Gly Tyr Glu Ile Phe Asn Asn Lys Glu Glu Asp Cys Arg Lys Val Val
370                375                380 ctg acg cca ggc ata gac gtt tcc gct gcc ccc aga cat taa             1194
Leu Thr Pro Gly Ile Asp Val Ser Ala Ala Pro Arg His
385                390                395

<210> SEQ ID NO 40
<211> LENGTH: 397
<212> TYPE: PRT
<213> ORGANISM: Methylophilus methylotrophus

<400> SEQUENCE: 40

Met Arg Ala Leu Thr Tyr His Gly Ser Lys Asp Val Arg Val Glu Thr
1               5                   10                  15

Val Pro Asp Pro Val Ile Gln Tyr Ala Asp Val Ile Leu Arg Val
                20                  25                  30

Thr Ala Thr Ala Ile Cys Gly Ser Asp Leu His Leu Tyr Arg Gly Lys
            35                  40                  45

Ile Pro Met Val Lys Asp Gly Asp Ile Leu Gly His Glu Phe Met Gly
        50                  55                  60

Val Ile Glu Glu Val Gly Ser Ala Val Asp Gln Val Gln Lys Gly Asp
65                  70                  75                  80

Arg Val Ile Ile Pro Phe Val Ile Ala Cys Gly His Cys Phe Phe Cys
                85                  90                  95
```

-continued

```
Glu Lys Ser Leu Tyr Ala Ala Cys Glu Asn Thr Asn Pro Gly Arg Gly
            100                 105                 110

Ala Ser Leu Asn Lys Lys Ser Val Lys Pro Pro Ala Ala Leu Phe Gly
            115                 120                 125

Tyr Ser His Leu Tyr Gly Gly Val Pro Gly Gly Gln Ala Glu Leu Val
            130                 135                 140

Arg Val Pro Arg Gly Asn Ala Gly Pro Phe Lys Val Pro Gly Ser Leu
145                 150                 155                 160

Ala Asp Glu Gln Val Leu Phe Leu Thr Asp Ile Leu Pro Thr Gly Tyr
                165                 170                 175

Gln Ala Val Leu Asn Ala Asp Val Val Pro Gly Ser Thr Ile Ala Ile
                180                 185                 190

Phe Gly Ala Gly Pro Val Gly Leu Met Ala Ala Ala Cys Ala Arg Met
            195                 200                 205

Leu Gly Ala Glu Thr Ile Phe Met Ile Asp His His Gln Tyr Arg Leu
            210                 215                 220

Asp Tyr Ala Ser Gln Val Tyr Asp Thr Ile Gly Ile Asn Phe Asp Glu
225                 230                 235                 240

Val Glu Asp Pro Ala Glu Phe Ile Leu Gln His Thr Gln His Arg Gly
                245                 250                 255

Val Asp Ala Ser Ile Asp Ala Val Gly Phe Glu Ala Lys Gly Ser Met
                260                 265                 270

Val Glu Thr Ala Leu Thr Thr Leu Lys Leu Glu Thr Ser Ser Gly Glu
            275                 280                 285

Thr Leu Arg Gln Cys Ile Ala Ala Thr Arg Arg Gly Gly Ile Ile Ser
            290                 295                 300

Ile Pro Gly Val Tyr Ala Gly Phe Ile His Ala Phe Leu Leu Gly Asp
305                 310                 315                 320

Ala Phe Asp Lys Gly Leu Thr Phe Lys Met Gly Gln Thr His Val His
                325                 330                 335

Gly Tyr Leu Ser Glu Leu Leu Arg Tyr Ile Glu Glu Asp Lys Leu Arg
            340                 345                 350

Pro Ala Asp Ile Ile Thr His Arg Met Ser Leu Glu Asp Ala Ala Lys
            355                 360                 365

Gly Tyr Glu Ile Phe Asn Asn Lys Glu Glu Asp Cys Arg Lys Val Val
            370                 375                 380

Leu Thr Pro Gly Ile Asp Val Ser Ala Ala Pro Arg His
385                 390                 395
```